US012636082B2

(12) United States Patent
Perler et al.

(10) Patent No.: US 12,636,082 B2
(45) Date of Patent: May 26, 2026

(54) PATIENT-SPECIFIC OSTEOTOMY INSTRUMENTATION

(71) Applicant: Treace Medical Concepts, Inc., Ponte Vedra, FL (US)

(72) Inventors: Adam D. Perler, St. Petersburg, FL (US); Samuel Adams, Chapel Hill, NC (US); Adam Schiff, Highland Park, IL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/412,197

(22) Filed: Jan. 12, 2024

(65) Prior Publication Data

US 2024/0189031 A1     Jun. 13, 2024

Related U.S. Application Data

(63) Continuation of application No. 17/832,594, filed on Jun. 4, 2022, now Pat. No. 11,986,251, which is a
(Continued)

(51) Int. Cl.
*A61B 17/15* (2006.01)
*A61B 17/17* (2006.01)
(Continued)

(52) U.S. Cl.
CPC ............ *A61B 34/10* (2016.02); *A61B 17/151* (2013.01); *A61B 17/1775* (2016.11);
(Continued)

(58) Field of Classification Search
CPC .......... A61B 2017/565; A61B 17/1775; A61B 2034/102; A61B 2034/105; A61B 2017/568
See application file for complete search history.

(56) References Cited

U.S. PATENT DOCUMENTS 3,664,022 A     5/1972  Small
4,069,824 A     1/1978  Weinstock
(Continued)

FOREIGN PATENT DOCUMENTS

AU     2009227957 B2     7/2014
AU     2009222469 B2     2/2015
(Continued)

OTHER PUBLICATIONS

Wendl et al., "Navigation in der Knieendoprothetik," OP-Journal, vol. 17, 2002, pp. 22-27, including English Abstract.
(Continued)

*Primary Examiner* — Samuel S Hanna
(74) *Attorney, Agent, or Firm* — Fredrikson & Byron, P.A.

(57)          ABSTRACT

A patient-specific instrument is disclosed for performing an osteotomy. The patient-specific instrument includes a body that includes a proximal side, a distal side, a medial side, a lateral side, and an inferior side having a bone engagement surface shaped to match at least one of a first surface of a first bone, a second surface of a second bone, a third surface of a third bone, and a fourth surface of a fourth bone of adjacent joints. The instrument also includes a superior side having one or more guide features that are positioned to guide resection of at least one of the first bone, the second bone, the third bone, and the fourth bone. The body is configured to seat transverse to the adjacent joints with the bone engagement surface engaging at least one of the first surface, the second surface, the third surface, and the fourth surface.

10 Claims, 29 Drawing Sheets

Related U.S. Application Data continuation-in-part of application No. 17/681,674, filed on Feb. 25, 2022, now Pat. No. 12,490,992, and a continuation-in-part of application No. 17/020,630, filed on Sep. 14, 2020, now Pat. No. 11,931,106.

(60) Provisional application No. 63/224,344, filed on Jul. 21, 2021, provisional application No. 62/900,294, filed on Sep. 13, 2019.

(51) Int. Cl.

| *A61B 34/10* | (2016.01) |
| *A61B 17/00* | (2006.01) |
| *A61B 17/56* | (2006.01) |

(52) U.S. Cl.
CPC .............. *A61B 2017/00526* (2013.01); *A61B 2017/568* (2013.01); *A61B 2034/108* (2016.02)

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,436,684 A | 3/1984 | White |
| 4,440,168 A | 4/1984 | Warren |
| 4,509,511 A | 4/1985 | Neufeld |
| 4,565,191 A | 1/1986 | Slocum |
| 4,570,624 A | 2/1986 | Wu |
| 4,628,919 A | 12/1986 | Clyburn |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,839,822 A | 6/1989 | Dormond et al. |
| 4,895,141 A | 1/1990 | Koeneman et al. |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,049,149 A | 9/1991 | Schmidt |
| 5,053,039 A | 10/1991 | Hofmann et al. |
| 5,112,334 A | 5/1992 | Alchermes et al. |
| 5,147,364 A | 9/1992 | Comparetto |
| 5,171,244 A | 12/1992 | Caspari et al. |
| 5,176,685 A | 1/1993 | Rayhack |
| 5,207,676 A | 5/1993 | Canadell et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,643,270 A | 7/1997 | Combs |
| 5,662,656 A | 9/1997 | White |
| 5,667,510 A | 9/1997 | Combs |
| H1706 H | 1/1998 | Mason |
| 5,722,978 A | 3/1998 | Jenkins, Jr. |
| 5,749,875 A | 5/1998 | Puddu |
| 5,779,709 A | 7/1998 | Harris, Jr. et al. |
| 5,788,695 A | 8/1998 | Richardson |
| 5,803,924 A | 9/1998 | Oni et al. |
| 5,810,822 A | 9/1998 | Mortier |
| 5,836,950 A | 11/1998 | Hansson |
| 5,839,438 A | 11/1998 | Graettinger et al. |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,957,927 A | 9/1999 | Magee et al. |
| 5,980,526 A | 11/1999 | Johnson et al. |
| 5,984,931 A | 11/1999 | Greenfield |
| 6,007,535 A | 12/1999 | Rayhack et al. |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,676,662 B1 | 1/2004 | Bagga et al. |
| 6,712,824 B2 | 3/2004 | Millard et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,780,190 B2 | 8/2004 | Maroney |
| 6,796,986 B2 | 9/2004 | Duffner |
| 6,859,661 B2 | 2/2005 | Tuke |
| 6,944,518 B2 | 9/2005 | Roose |
| 6,964,645 B1 | 11/2005 | Smits |
| 7,033,361 B2 | 4/2006 | Collazo |
| 7,097,647 B2 | 8/2006 | Segler |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,351,203 B2 | 4/2008 | Jelliffe et al. |
| 7,377,924 B2 | 5/2008 | Raistrick et al. |
| 7,465,303 B2 | 12/2008 | Riccione et al. |
| 7,473,255 B2 | 1/2009 | Mcgarity et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,670,345 B2 | 3/2010 | Plassky et al. |
| 7,686,811 B2 | 3/2010 | Byrd et al. |
| 7,691,108 B2 | 4/2010 | Lavallee |
| 7,763,026 B2 | 7/2010 | Egger et al. |
| 7,789,885 B2 | 9/2010 | Metzger |
| D629,900 S | 12/2010 | Fisher |
| 7,875,058 B2 | 1/2011 | Holmes, Jr. |
| 7,972,338 B2 | 7/2011 | O'Brien |
| 7,983,777 B2 | 7/2011 | Melton et al. |
| D646,389 S | 10/2011 | Claypool et al. |
| 8,057,473 B2 | 11/2011 | Orsak et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton |
| 8,114,087 B2 | 2/2012 | Long et al. |
| 8,123,753 B2 | 2/2012 | Poncet |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,187,280 B2 | 5/2012 | May et al. |
| 8,192,441 B2 | 6/2012 | Collazo |
| 8,197,487 B2 | 6/2012 | Poncet et al. |
| 8,206,153 B2 | 6/2012 | Suttin et al. |
| 8,231,623 B1 | 7/2012 | Jordan |
| 8,231,663 B2 | 7/2012 | Kay et al. |
| 8,246,561 B1 | 8/2012 | Agee et al. |
| 8,246,680 B2 | 8/2012 | Betz et al. |
| D666,721 S | 9/2012 | Wright et al. |
| 8,262,664 B2 | 9/2012 | Justin et al. |
| 8,262,665 B2 | 9/2012 | Massoud |

(56) References Cited

U.S. PATENT DOCUMENTS

| | | | |
|---|---|---|---|
| 8,277,455 | B2 | 10/2012 | Couture et al. |
| 8,282,644 | B2 | 10/2012 | Edwards |
| 8,282,645 | B2 | 10/2012 | Lawrence et al. |
| 8,287,541 | B2 | 10/2012 | Nelson et al. |
| 8,292,966 | B2 | 10/2012 | Morton |
| 8,303,596 | B2 | 11/2012 | Plaky et al. |
| 8,323,281 | B2 | 12/2012 | Hotchkiss et al. |
| 8,323,289 | B2 | 12/2012 | Re |
| 8,357,111 | B2 | 1/2013 | Caillouette et al. |
| 8,377,105 | B2 | 2/2013 | Bscher |
| 8,388,690 | B2 | 3/2013 | Singhatat et al. |
| D679,395 | S | 4/2013 | Wright et al. |
| 8,435,246 | B2 | 5/2013 | Fisher et al. |
| 8,475,462 | B2 | 7/2013 | Thomas et al. |
| 8,484,001 | B2 | 7/2013 | Glozman et al. |
| 8,518,045 | B2 | 8/2013 | Szanto |
| 8,523,870 | B2 | 9/2013 | Green, II et al. |
| 8,529,568 | B2 | 9/2013 | Bouadi |
| 8,532,807 | B2 | 9/2013 | Metzger |
| 8,551,106 | B2 | 10/2013 | Harrold |
| D694,884 | S | 12/2013 | Mooradian et al. |
| D695,402 | S | 12/2013 | Dacosta et al. |
| 8,641,721 | B2 | 2/2014 | Aram et al. |
| 8,652,142 | B2 | 2/2014 | Geissler |
| 8,657,820 | B2 | 2/2014 | Kubiak et al. |
| D701,303 | S | 3/2014 | Cook |
| 8,663,234 | B2 | 3/2014 | Grimm et al. |
| 8,668,700 | B2 | 3/2014 | Catanzarite et al. |
| 8,685,030 | B2 | 4/2014 | Gtte et al. |
| 8,696,719 | B2 | 4/2014 | Lofthouse et al. |
| 8,702,686 | B2 | 4/2014 | Geebelen et al. |
| 8,702,712 | B2 | 4/2014 | Jordan et al. |
| 8,715,289 | B2 | 5/2014 | Smith |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,777,948 | B2 | 7/2014 | Bernsteiner |
| 8,784,457 | B2 | 7/2014 | Graham |
| 8,795,286 | B2 | 8/2014 | Sand et al. |
| 8,808,298 | B2 | 8/2014 | Raub et al. |
| 8,808,301 | B1 | 8/2014 | Nofsinger |
| 8,808,302 | B2 | 8/2014 | Roose et al. |
| 8,828,012 | B2 | 9/2014 | May et al. |
| 8,838,263 | B2 | 9/2014 | Sivak et al. |
| 8,858,602 | B2 | 10/2014 | Weiner et al. |
| 8,864,773 | B2 | 10/2014 | Paul et al. |
| 8,882,778 | B2 | 11/2014 | Ranft |
| 8,882,816 | B2 | 11/2014 | Kartalian et al. |
| 8,892,235 | B2 | 11/2014 | Choi et al. |
| 8,898,043 | B2 | 11/2014 | Ashby et al. |
| D720,456 | S | 12/2014 | Dacosta et al. |
| 8,900,247 | B2 | 12/2014 | Tseng et al. |
| 8,911,444 | B2 | 12/2014 | Bailey |
| 8,920,428 | B2 | 12/2014 | Zakaria et al. |
| 8,926,612 | B2 | 1/2015 | Graham |
| 8,932,299 | B2 | 1/2015 | Bono et al. |
| 8,939,982 | B2 | 1/2015 | Chellaoui |
| 8,939,984 | B2 | 1/2015 | Budoff |
| 8,945,132 | B2 | 2/2015 | Play et al. |
| 8,965,075 | B2 | 2/2015 | Arnaud et al. |
| 8,974,460 | B2 | 3/2015 | De La Fuente et al. |
| 8,979,856 | B2 | 3/2015 | Catanzarite et al. |
| 8,992,531 | B2 | 3/2015 | Chow et al. |
| 8,992,532 | B2 | 3/2015 | Wong |
| 8,998,903 | B2 | 4/2015 | Price et al. |
| 8,998,904 | B2 | 4/2015 | Zeetser et al. |
| 8,998,907 | B2 | 4/2015 | Myers |
| 8,998,909 | B2 | 4/2015 | Gillman et al. |
| 9,005,207 | B2 | 4/2015 | Dodds et al. |
| 9,011,451 | B2 | 4/2015 | Long et al. |
| 9,011,452 | B2 | 4/2015 | Iannotti et al. |
| 9,011,456 | B2 | 4/2015 | Ranawat et al. |
| 9,014,835 | B2 | 4/2015 | Azernikov et al. |
| 9,017,329 | B2 | 4/2015 | Tyber et al. |
| 9,017,336 | B2 | 4/2015 | Park et al. |
| 9,023,052 | B2 | 5/2015 | Lietz et al. |
| 9,044,250 | B2 | 6/2015 | Olsen et al. |
| 9,060,788 | B2 | 6/2015 | Bollinger |
| 9,060,822 | B2 | 6/2015 | Wright et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,915 | B2 | 8/2015 | Thomas et al. |
| 9,113,957 | B2 | 8/2015 | Axelson, Jr. et al. |
| 9,138,237 | B2 | 9/2015 | Meade et al. |
| 9,138,332 | B2 | 9/2015 | Harris et al. |
| D740,424 | S | 10/2015 | Dacosta et al. |
| 9,173,665 | B2 | 11/2015 | Couture |
| 9,173,691 | B2 | 11/2015 | Orbay et al. |
| 9,186,154 | B2 | 11/2015 | Li |
| 9,186,160 | B1 | 11/2015 | Song |
| 9,198,678 | B2 | 12/2015 | Frey et al. |
| 9,204,897 | B2 | 12/2015 | Jones et al. |
| 9,211,128 | B2 | 12/2015 | Gillman et al. |
| 9,220,509 | B2 | 12/2015 | Boyer et al. |
| 9,220,518 | B2 | 12/2015 | Neal et al. |
| 9,220,519 | B2 | 12/2015 | Kaneyama et al. |
| 9,220,551 | B2 | 12/2015 | Waizenegger |
| 9,232,951 | B2 | 1/2016 | Johannaber |
| 9,232,955 | B2 | 1/2016 | Bonin, Jr. et al. |
| 9,254,155 | B2 | 2/2016 | Iannotti et al. |
| 9,295,497 | B2 | 3/2016 | Schoenefeld et al. |
| 9,301,768 | B2 | 4/2016 | Buza et al. |
| 9,301,783 | B2 | 4/2016 | Gerold et al. |
| 9,308,006 | B2 | 4/2016 | Martin et al. |
| 9,308,037 | B2 | 4/2016 | Richter et al. |
| 9,320,609 | B2 | 4/2016 | Schon et al. |
| 9,345,497 | B2 | 5/2016 | Gonzalvez et al. |
| 9,351,738 | B2 | 5/2016 | Aram et al. |
| 9,351,743 | B2 | 5/2016 | Kehres et al. |
| 9,370,380 | B2 | 6/2016 | Riccione |
| 9,375,220 | B2 | 6/2016 | Horan et al. |
| 9,402,636 | B2 | 8/2016 | Collazo |
| 9,402,640 | B2 | 8/2016 | Reynolds et al. |
| 9,408,641 | B2 | 8/2016 | Zhang et al. |
| 9,414,846 | B2 | 8/2016 | Gillman et al. |
| 9,414,847 | B2 | 8/2016 | Kurtz |
| 9,414,877 | B2 | 8/2016 | Helenbolt et al. |
| 9,421,021 | B2 | 8/2016 | Keppler |
| 9,427,240 | B2 | 8/2016 | Von Zabern et al. |
| D765,844 | S | 9/2016 | Dacosta |
| D766,434 | S | 9/2016 | Dacosta |
| D766,437 | S | 9/2016 | Dacosta |
| D766,438 | S | 9/2016 | Dacosta |
| D766,439 | S | 9/2016 | Dacosta |
| 9,433,452 | B2 | 9/2016 | Weiner et al. |
| 9,445,823 | B2 | 9/2016 | Harris et al. |
| 9,452,050 | B2 | 9/2016 | Miles et al. |
| 9,456,902 | B2 | 10/2016 | Hacking et al. |
| 9,463,034 | B2 | 10/2016 | Wong et al. |
| 9,492,182 | B2 | 11/2016 | Keefer |
| 9,517,145 | B2 | 12/2016 | Meridew et al. |
| 9,522,023 | B2 | 12/2016 | Haddad et al. |
| 9,526,514 | B2 | 12/2016 | Kelley et al. |
| 9,545,276 | B2 | 1/2017 | Buchanan et al. |
| 9,561,041 | B2 | 2/2017 | Snider et al. |
| 9,566,103 | B2 | 2/2017 | Mayer |
| 9,579,106 | B2 | 2/2017 | Lo et al. |
| 9,579,107 | B2 | 2/2017 | Schoenefeld |
| 9,579,112 | B2 | 2/2017 | Catanzarite et al. |
| 9,592,084 | B2 | 3/2017 | Grant |
| 9,603,605 | B2 | 3/2017 | Collazo |
| 9,603,640 | B2 | 3/2017 | Palmer et al. |
| 9,622,820 | B2 | 4/2017 | Baloch et al. |
| 9,629,726 | B2 | 4/2017 | Reiley et al. |
| 9,652,889 | B2 | 5/2017 | Young et al. |
| 9,662,220 | B2 | 5/2017 | Warburton |
| 9,668,746 | B2 | 6/2017 | Lee et al. |
| 9,675,471 | B2 | 6/2017 | Bojarski et al. |
| 9,687,261 | B2 | 6/2017 | Serbousek et al. |
| 9,693,787 | B2 | 7/2017 | Ammann et al. |
| 9,693,878 | B2 | 7/2017 | Kunz et al. |
| 9,700,433 | B2 | 7/2017 | Myers |
| 9,713,484 | B2 | 7/2017 | Sammarco |

(56)        References Cited

U.S. PATENT DOCUMENTS

| | | | |
|---|---|---|---|
| 9,737,311 B2 | 8/2017 | Lavallee et al. |
| 9,737,367 B2 | 8/2017 | Steines et al. |
| 9,750,538 B2 | 9/2017 | Soffiatti et al. |
| 9,785,747 B2 | 10/2017 | Geebelen |
| 9,788,958 B2 | 10/2017 | Melamed et al. |
| 9,788,975 B2 | 10/2017 | Li |
| 9,795,392 B2 | 10/2017 | Zajac |
| 9,795,394 B2 | 10/2017 | Bonutti |
| 9,814,474 B2 | 11/2017 | Montoya et al. |
| 9,820,868 B2 | 11/2017 | Witt et al. |
| 9,826,981 B2 | 11/2017 | Schoenefeld et al. |
| 9,839,438 B2 | 12/2017 | Eash |
| 9,848,929 B2 | 12/2017 | Dacosta et al. |
| 9,849,019 B2 | 12/2017 | Miller et al. |
| 9,877,754 B2 | 1/2018 | Patel et al. |
| 9,883,954 B1 | 2/2018 | Murphy |
| 9,888,931 B2 | 2/2018 | Bake |
| 9,888,950 B2 | 2/2018 | Perez et al. |
| 9,918,658 B2 | 3/2018 | Mccaulley et al. |
| 9,918,769 B2 | 3/2018 | Provencher et al. |
| 9,925,049 B2 | 3/2018 | Goldstein et al. |
| 9,925,068 B2 | 3/2018 | Bays et al. |
| 9,956,089 B2 | 5/2018 | Kelman et al. |
| 9,968,456 B2 | 5/2018 | Song |
| 9,980,760 B2 | 5/2018 | Dacosta et al. |
| 9,987,092 B2 | 6/2018 | Hladio et al. |
| 9,990,765 B2 | 6/2018 | Ju et al. |
| 9,993,256 B2 | 6/2018 | Lipman et al. |
| 10,002,227 B2 | 6/2018 | Netravali et al. |
| 10,004,516 B2 | 6/2018 | Johannaber |
| 10,010,431 B2 | 7/2018 | Eraly et al. |
| 10,016,177 B2 | 7/2018 | Aram et al. |
| 10,022,170 B2 | 7/2018 | Leemrijse et al. |
| 10,028,756 B2 | 7/2018 | Liu |
| 10,034,753 B2 | 7/2018 | Dressler et al. |
| 10,052,114 B2 | 8/2018 | Keppler et al. |
| 10,055,536 B2 | 8/2018 | Maes et al. |
| 10,058,335 B2 | 8/2018 | Lee et al. |
| 10,089,413 B2 | 10/2018 | Wirx-Speetjens et al. |
| 10,098,761 B2 | 10/2018 | Sherman et al. |
| 10,105,145 B2 | 10/2018 | Lavallee |
| 10,123,807 B2 | 11/2018 | Geebelen |
| 10,130,378 B2 | 11/2018 | Bryan |
| 10,149,722 B2 | 12/2018 | Aram et al. |
| 10,159,480 B2 | 12/2018 | Tuten |
| 10,159,499 B2 | 12/2018 | Dacosta et al. |
| 10,159,512 B2 | 12/2018 | Robinson |
| 10,201,357 B2 | 2/2019 | Aram et al. |
| 10,206,692 B2 | 2/2019 | Sanders |
| 10,217,530 B2 | 2/2019 | Couture et al. |
| 10,219,812 B2 | 3/2019 | Torrie et al. |
| 10,226,292 B2 | 3/2019 | Lundquist et al. |
| 10,231,745 B2 | 3/2019 | Geebelen et al. |
| 10,238,382 B2 | 3/2019 | Terrill et al. |
| 10,251,654 B2 | 4/2019 | Fritzinger |
| 10,251,690 B2 | 4/2019 | Katrana et al. |
| 10,262,084 B2 | 4/2019 | Lavallee et al. |
| 10,265,080 B2 | 4/2019 | Hughes et al. |
| 10,271,886 B2 | 4/2019 | Abiven |
| 10,278,713 B2 | 5/2019 | Richter et al. |
| 10,282,488 B2 | 5/2019 | Eash |
| 10,286,197 B2 | 5/2019 | Pouliot et al. |
| 10,325,065 B2 | 6/2019 | Li et al. |
| 10,327,829 B2 | 6/2019 | Dacosta et al. |
| 10,342,529 B2 | 7/2019 | Fallin et al. |
| 10,350,022 B2 | 7/2019 | Jansen et al. |
| 10,357,261 B2 | 7/2019 | Kugler et al. |
| 10,357,299 B2 | 7/2019 | Weiner et al. |
| 10,363,052 B2 | 7/2019 | Park et al. |
| 10,398,510 B2 | 9/2019 | Goto |
| 10,420,613 B2 | 9/2019 | Azevedo Da Silva et al. |
| 10,456,205 B2 | 10/2019 | Meridew et al. |
| 10,512,470 B1 | 12/2019 | Bays et al. |
| 10,524,808 B1 | 1/2020 | Hissong et al. |
| 10,524,845 B2 | 1/2020 | Orsak et al. |
| 10,537,392 B2 | 1/2020 | Millahn et al. |
| 10,543,100 B2 | 1/2020 | Couture et al. |
| 10,548,667 B2 | 2/2020 | Flett et al. |
| 10,548,668 B2 | 2/2020 | Furrer et al. |
| 10,582,969 B2 | 3/2020 | Couture et al. |
| 10,610,241 B2 | 4/2020 | Wagner et al. |
| 10,631,878 B2 | 4/2020 | Fritzinger |
| 10,631,902 B2 | 4/2020 | Weiner et al. |
| 10,653,432 B2 | 5/2020 | Luttrell et al. |
| 10,653,464 B2 | 5/2020 | Hill et al. |
| 10,653,467 B2 | 5/2020 | Brumfield et al. |
| 10,675,096 B2 | 6/2020 | Utz et al. |
| 10,682,147 B2 | 6/2020 | Grant et al. |
| 10,709,567 B2 | 7/2020 | Welker et al. |
| 10,716,581 B2 | 7/2020 | Fritzinger et al. |
| 10,722,309 B2 | 7/2020 | Gillman |
| 10,722,310 B2 | 7/2020 | Luby |
| 10,779,867 B2 | 9/2020 | Penzimer et al. |
| 10,779,890 B2 | 9/2020 | Weir |
| 10,786,291 B2 | 9/2020 | Weiner et al. |
| 10,792,081 B2 | 10/2020 | Weiner et al. |
| 10,806,469 B2 | 10/2020 | Fiechter et al. |
| 10,849,665 B2 | 12/2020 | Singh et al. |
| 10,849,670 B2 | 12/2020 | Santrock et al. |
| 10,856,891 B2 | 12/2020 | Rhodes et al. |
| 10,856,925 B1 | 12/2020 | Pontell |
| 10,869,722 B2 | 12/2020 | Caldwell et al. |
| 10,874,408 B2 | 12/2020 | Couture |
| 10,881,416 B2 | 1/2021 | Couture et al. |
| 10,881,417 B2 | 1/2021 | Mahfouz |
| 10,888,340 B2 | 1/2021 | Awtrey et al. |
| 10,905,444 B2 | 2/2021 | Siccardi et al. |
| 10,912,574 B2 | 2/2021 | Kim et al. |
| 10,925,622 B2 | 2/2021 | Kehres et al. |
| 10,939,926 B2 | 3/2021 | Kam et al. |
| 10,939,939 B1 | 3/2021 | Gil et al. |
| 10,973,529 B2 | 4/2021 | Lavallee et al. |
| 11,000,327 B2 | 5/2021 | Schlotterback et al. |
| 11,020,128 B2 | 6/2021 | Guilloux et al. |
| 11,033,336 B2 | 6/2021 | Bohl |
| 11,065,011 B2 | 7/2021 | Bake et al. |
| 11,074,688 B2 | 7/2021 | Chabin et al. |
| 11,090,069 B2 | 8/2021 | Park |
| 11,090,161 B2 | 8/2021 | Hodorek |
| 11,112,770 B2 | 9/2021 | Roh et al. |
| 11,116,518 B2 | 9/2021 | Hafez |
| 11,129,625 B2 | 9/2021 | Song et al. |
| 11,129,678 B2 | 9/2021 | Park |
| 11,154,362 B2 | 10/2021 | Kim et al. |
| 11,158,047 B2 | 10/2021 | Shah |
| 11,160,567 B2 | 11/2021 | Fallin et al. |
| 11,160,568 B1 | 11/2021 | Park |
| 11,166,732 B2 | 11/2021 | Maxson et al. |
| 11,172,945 B1 | 11/2021 | Lian |
| 11,179,165 B2 | 11/2021 | Schoenefeld |
| 11,179,168 B2 | 11/2021 | Dacosta et al. |
| 11,207,134 B2 | 12/2021 | Hafez |
| 11,213,305 B2 | 1/2022 | Tannotti et al. |
| 11,213,406 B2 | 1/2022 | Rodriguez et al. |
| 11,219,526 B2 | 1/2022 | Mahfouz |
| 11,224,448 B2 | 1/2022 | Bailey |
| 11,259,817 B2 | 3/2022 | Fallin et al. |
| 11,284,909 B2 | 3/2022 | Castricini et al. |
| 11,304,705 B2 | 4/2022 | Fallin et al. |
| 11,304,735 B2 | 4/2022 | Sayger et al. |
| 11,324,522 B2 | 5/2022 | Metzger et al. |
| 11,324,607 B2 | 5/2022 | Mauldin et al. |
| 11,331,148 B2 | 5/2022 | Fritzinger |
| 11,331,205 B2 | 5/2022 | Parr |
| 11,344,347 B2 | 5/2022 | Treace et al. |
| 11,389,221 B2 | 7/2022 | Tyber et al. |
| 11,399,849 B2 | 8/2022 | Larche et al. |
| 11,419,726 B2 | 8/2022 | Miller et al. |
| 11,426,184 B2 | 8/2022 | Rivet-Sabourin et al. |
| 11,432,931 B2 | 9/2022 | Lang |
| 11,436,801 B2 | 9/2022 | Haslam et al. |
| 11,439,412 B2 | 9/2022 | Woodard et al. |
| 11,457,980 B2 | 10/2022 | Bonny et al. |
| 11,484,354 B2 | 11/2022 | Singh et al. |

(56) References Cited

U.S. PATENT DOCUMENTS

| | | |
|---|---|---|
| 11,497,557 B2 | 11/2022 | Haslam et al. |
| 11,508,102 B2 | 11/2022 | Su et al. |
| 11,510,738 B2 | 11/2022 | Stifter et al. |
| 11,532,402 B2 | 12/2022 | Farley et al. |
| 11,557,036 B2 | 1/2023 | Mansi et al. |
| 11,571,312 B1 | 2/2023 | Parekh et al. |
| 11,583,298 B2 | 2/2023 | Robichaud et al. |
| 11,596,421 B2 | 3/2023 | Saltzman et al. |
| 11,596,443 B2 | 3/2023 | Treace et al. |
| 11,602,386 B2 | 3/2023 | Smith et al. |
| 11,607,250 B2 | 3/2023 | Treace et al. |
| 11,627,954 B2 | 4/2023 | May et al. |
| 11,628,003 B2 | 4/2023 | Nachtrab et al. |
| 11,633,195 B2 | 4/2023 | Dhillon |
| 11,648,019 B2 | 5/2023 | Bays et al. |
| 11,653,938 B2 | 5/2023 | Siegler |
| 11,684,423 B2 | 6/2023 | Jaramaz et al. |
| 11,690,725 B2 | 7/2023 | Gemon et al. |
| 11,717,359 B2 | 8/2023 | Chi |
| 11,741,277 B2 | 8/2023 | Dayal et al. |
| 11,751,892 B2 | 9/2023 | Woodard et al. |
| 11,756,051 B2 | 9/2023 | Indani et al. |
| 11,766,268 B2 | 9/2023 | Iannotti et al. |
| 11,779,467 B2 | 10/2023 | Mimnaugh et al. |
| 11,786,257 B2 | 10/2023 | Dayton et al. |
| 11,793,549 B2 | 10/2023 | Rhodes et al. |
| 11,812,978 B2 | 11/2023 | Trabish et al. |
| 11,819,223 B2 | 11/2023 | Lee |
| 11,819,224 B2 | 11/2023 | Allard et al. |
| 11,849,933 B2 | 12/2023 | Denham et al. |
| 11,849,957 B2 | 12/2023 | Couture et al. |
| 11,849,961 B2 | 12/2023 | Khatibi et al. |
| 11,849,962 B2 | 12/2023 | Singh et al. |
| 11,854,683 B2 | 12/2023 | Casey et al. |
| D1,011,524 S | 1/2024 | Santrock et al. |
| 11,857,206 B2 | 1/2024 | Robichaud et al. |
| 11,864,778 B2 | 1/2024 | Mcginley et al. |
| 11,864,959 B2 | 1/2024 | Basta |
| 11,911,046 B2 | 2/2024 | Carroll et al. |
| 11,925,417 B2 | 3/2024 | Mosnier et al. |
| 11,931,106 B2 | 3/2024 | Perler et al. |
| 11,944,546 B2 | 4/2024 | Puncreobutr et al. |
| 11,950,786 B2 | 4/2024 | Courtis et al. |
| 11,963,687 B2 | 4/2024 | Langhorn et al. |
| 11,963,703 B2 | 4/2024 | Dayton et al. |
| 11,963,729 B2 | 4/2024 | Aljuri et al. |
| 11,980,377 B2 | 5/2024 | Mauldin et al. |
| 12,004,789 B2 | 6/2024 | Mcaleer et al. |
| 12,004,814 B2 | 6/2024 | Ryan et al. |
| D1,034,985 S | 7/2024 | Hartson et al. |
| 12,035,929 B2 | 7/2024 | Athwal et al. |
| 12,045,943 B2 | 7/2024 | Chaoui et al. |
| 12,048,600 B2 | 7/2024 | Azernikov et al. |
| 12,050,999 B2 | 7/2024 | Poltaretskyi et al. |
| 12,053,242 B2 | 8/2024 | Landon et al. |
| 12,062,183 B2 | 8/2024 | Chaoui et al. |
| 12,097,129 B2 | 9/2024 | Deransart et al. |
| 12,115,083 B2 | 10/2024 | Mullen et al. |
| 12,121,272 B2 | 10/2024 | Marien et al. |
| 2002/0107519 A1 | 8/2002 | Dixon et al. |
| 2003/0236522 A1 | 12/2003 | Long et al. |
| 2004/0010259 A1 | 1/2004 | Keller et al. |
| 2004/0039394 A1 | 2/2004 | Conti et al. |
| 2004/0039396 A1 | 2/2004 | Couture et al. |
| 2004/0097946 A1 | 5/2004 | Dietzel et al. |
| 2004/0138669 A1 | 7/2004 | Horn |
| 2005/0059978 A1 | 3/2005 | Sherry et al. |
| 2005/0080424 A1 | 4/2005 | Cuckler et al. |
| 2005/0267482 A1 | 12/2005 | Hyde |
| 2005/0273112 A1 | 12/2005 | Mcnamara |
| 2006/0129163 A1 | 6/2006 | Mcguire |
| 2006/0206044 A1 | 9/2006 | Simon |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0161815 A1 | 7/2008 | Schoenefeld et al. |
| 2008/0172054 A1 | 7/2008 | Claypool et al. |
| 2008/0288004 A1 | 11/2008 | Schendel |
| 2009/0036931 A1 | 2/2009 | Pech et al. |
| 2009/0089081 A1 | 4/2009 | Haddad |
| 2009/0093849 A1 | 4/2009 | Grabowski |
| 2009/0099567 A1 | 4/2009 | Zajac |
| 2009/0105767 A1 | 4/2009 | Reiley |
| 2009/0198244 A1 | 8/2009 | Leibel |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0265012 A1 | 10/2009 | Engh et al. |
| 2009/0287309 A1 | 11/2009 | Walch et al. |
| 2010/0069910 A1 | 3/2010 | Hasselman |
| 2010/0130981 A1 | 5/2010 | Richards |
| 2010/0168799 A1 | 7/2010 | Schumer |
| 2010/0185202 A1 | 7/2010 | Lester et al. |
| 2010/0217270 A1 | 8/2010 | Polinski et al. |
| 2010/0256687 A1 | 10/2010 | Neufeld et al. |
| 2010/0274253 A1 | 10/2010 | Ure |
| 2010/0318088 A1 | 12/2010 | Warne et al. |
| 2011/0009865 A1 | 1/2011 | Orfaly |
| 2012/0065689 A1 | 3/2012 | Prasad et al. |
| 2012/0116203 A1 | 5/2012 | Vancraen et al. |
| 2012/0123420 A1 | 5/2012 | Honiball |
| 2012/0130434 A1 | 5/2012 | Stemniski |
| 2012/0150242 A1 | 6/2012 | Mannion |
| 2012/0191199 A1 | 7/2012 | Raemisch |
| 2012/0234329 A1 | 9/2012 | Vancraen et al. |
| 2012/0253350 A1 | 10/2012 | Anthony et al. |
| 2012/0265301 A1 | 10/2012 | Demers et al. |
| 2012/0277745 A1 | 11/2012 | Lizee |
| 2013/0211410 A1 | 8/2013 | Landes et al. |
| 2013/0236874 A1 | 9/2013 | Tannotti et al. |
| 2013/0237989 A1 | 9/2013 | Bonutti |
| 2013/0274778 A1 | 10/2013 | Mercier et al. |
| 2013/0289570 A1 | 10/2013 | Chao |
| 2013/0292870 A1 | 11/2013 | Roger |
| 2014/0005672 A1 | 1/2014 | Edwards et al. |
| 2014/0039501 A1 | 2/2014 | Schickendantz et al. |
| 2014/0074099 A1 | 3/2014 | Vigneron et al. |
| 2014/0094861 A1 | 4/2014 | Fallin |
| 2014/0163568 A1 | 6/2014 | Wong et al. |
| 2014/0257402 A1 | 9/2014 | Barsoum |
| 2014/0259629 A1 | 9/2014 | Dion et al. |
| 2014/0263674 A1 | 9/2014 | Cerveny |
| 2014/0343555 A1 | 11/2014 | Russi et al. |
| 2014/0371866 A1 | 12/2014 | Chao et al. |
| 2014/0371897 A1 | 12/2014 | Lin et al. |
| 2015/0032215 A1 | 1/2015 | Slamin et al. |
| 2015/0045903 A1 | 2/2015 | Neal |
| 2015/0066094 A1 | 3/2015 | Anderson et al. |
| 2015/0081029 A1 | 3/2015 | Bojarski et al. |
| 2015/0088142 A1 | 3/2015 | Gibson |
| 2015/0093283 A1 | 4/2015 | Miller et al. |
| 2015/0112348 A1 | 4/2015 | Schoenefeld et al. |
| 2015/0142000 A1 | 5/2015 | Seedhom et al. |
| 2015/0182342 A1 | 7/2015 | Hafez |
| 2015/0227679 A1 | 8/2015 | Kamer et al. |
| 2015/0230843 A1 | 8/2015 | Palmer et al. |
| 2015/0305752 A1 | 10/2015 | Eash |
| 2015/0342616 A1 | 12/2015 | Fryman |
| 2015/0351780 A1 | 12/2015 | Anderson et al. |
| 2015/0351916 A1 | 12/2015 | Kosarek et al. |
| 2016/0015426 A1 | 1/2016 | Dayton |
| 2016/0038161 A1 | 2/2016 | Gibson |
| 2016/0100773 A1 | 4/2016 | Ching et al. |

(56) References Cited

U.S. PATENT DOCUMENTS

| | | |
|---|---|---|
| 2016/0100847 A1 | 4/2016 | Maxson |
| 2016/0151165 A1 | 6/2016 | Fallin et al. |
| 2016/0175089 A1 | 6/2016 | Fallin et al. |
| 2016/0192951 A1 | 7/2016 | Gelaude et al. |
| 2016/0199198 A1 | 7/2016 | Dietz et al. |
| 2016/0256176 A9 | 9/2016 | Lowery et al. |
| 2016/0270829 A1 | 9/2016 | Duggal et al. |
| 2016/0270855 A1 | 9/2016 | Kunz et al. |
| 2016/0287395 A1 | 10/2016 | Khalili et al. |
| 2016/0338715 A1 | 11/2016 | Bojarski et al. |
| 2016/0354128 A1 | 12/2016 | Jeng et al. |
| 2016/0367270 A1 | 12/2016 | Garlock et al. |
| 2017/0014169 A1 | 1/2017 | Dean et al. |
| 2017/0020537 A1 | 1/2017 | Tuten |
| 2017/0027593 A1 | 2/2017 | Bojarski et al. |
| 2017/0042599 A1 | 2/2017 | Bays et al. |
| 2017/0079803 A1 | 3/2017 | Lang |
| 2017/0143511 A1 | 5/2017 | Cachia |
| 2017/0209189 A9 | 7/2017 | Hatch et al. |
| 2017/0231645 A1 | 8/2017 | Metzger et al. |
| 2017/0245906 A1 | 8/2017 | Kugler et al. |
| 2017/0245935 A1 | 8/2017 | Kugler et al. |
| 2017/0249440 A1 | 8/2017 | Lang et al. |
| 2017/0281353 A1 | 10/2017 | Al Hares et al. |
| 2017/0360578 A1 | 12/2017 | Shin et al. |
| 2018/0021145 A1 | 1/2018 | Seavey et al. |
| 2018/0028325 A1 | 2/2018 | Bojarski et al. |
| 2018/0049758 A1 | 2/2018 | Amis et al. |
| 2018/0116804 A1 | 5/2018 | Hafez et al. |
| 2018/0221071 A1 | 8/2018 | Isch |
| 2018/0235706 A1 | 8/2018 | Asseln et al. |
| 2018/0242987 A1 | 8/2018 | Lintula et al. |
| 2018/0289423 A1 | 10/2018 | Singh et al. |
| 2018/0317986 A1 | 11/2018 | Jackman et al. |
| 2018/0344326 A1 | 12/2018 | Chan et al. |
| 2019/0000629 A1 | 1/2019 | Winslow |
| 2019/0008532 A1 | 1/2019 | Fitz et al. |
| 2019/0117239 A1 | 4/2019 | Verma |
| 2019/0175277 A1 | 6/2019 | Chav et al. |
| 2019/0175351 A1 | 6/2019 | Bojarski et al. |
| 2019/0307495 A1 | 10/2019 | Geldwert |
| 2019/0365543 A1 | 12/2019 | Slamin et al. |
| 2020/0008813 A1 | 1/2020 | Bonny et al. |
| 2020/0046425 A1 | 2/2020 | Lopes et al. |
| 2020/0100909 A1 | 4/2020 | Lang et al. |
| 2020/0155323 A1 | 5/2020 | Lang et al. |
| 2020/0163721 A1 | 5/2020 | Aghazadeh |
| 2020/0214719 A1 | 7/2020 | Fraone et al. |
| 2020/0337714 A1 | 10/2020 | Hafez et al. |
| 2020/0356073 A1 | 11/2020 | Tokushima |
| 2020/0405322 A1 | 12/2020 | Brailovski et al. |
| 2021/0007760 A1 | 1/2021 | Reisin |
| 2021/0022781 A1 | 1/2021 | Dacosta et al. |
| 2021/0030429 A1 | 2/2021 | Rose et al. |
| 2021/0045756 A1 | 2/2021 | Zakhary et al. |
| 2021/0059691 A1 | 3/2021 | Zille |
| 2021/0059837 A1 | 3/2021 | Rhodes |
| 2021/0077120 A1 | 3/2021 | Hatch et al. |
| 2021/0077192 A1 | 3/2021 | Perler et al. |
| 2021/0085338 A1 | 3/2021 | Dacosta et al. |
| 2021/0090248 A1 | 3/2021 | Choi et al. |
| 2021/0106427 A1 | 4/2021 | Mahfouz |
| 2021/0113223 A1 | 4/2021 | Schaumann et al. |
| 2021/0121297 A1 | 4/2021 | Cavanagh et al. |
| 2021/0137537 A1 | 5/2021 | Zille |
| 2021/0161543 A1 | 6/2021 | Mcauliffe et al. |
| 2021/0186704 A1 | 6/2021 | Fitz et al. |
| 2021/0192759 A1 | 6/2021 | Lang |
| 2021/0196290 A1 | 7/2021 | Iannotti et al. |
| 2021/0212705 A1 | 7/2021 | Reynolds et al. |
| 2021/0219989 A1 | 7/2021 | Chao |
| 2021/0244477 A1 | 8/2021 | Singh et al. |
| 2021/0256171 A1 | 8/2021 | Hosseini |
| 2021/0275196 A1 | 9/2021 | Wodajo |
| 2021/0282790 A1 | 9/2021 | Sellman et al. |
| 2021/0282823 A1 | 9/2021 | Day et al. |
| 2021/0290250 A1 | 9/2021 | Denham et al. |
| 2021/0298766 A1 | 9/2021 | Loring et al. |
| 2021/0307833 A1 | 10/2021 | Farley et al. |
| 2021/0307834 A1 | 10/2021 | Gillman et al. |
| 2021/0346038 A1 | 11/2021 | Fiechter et al. |
| 2021/0361330 A1* | 11/2021 | McAleer ........... A61B 17/8061 |
| 2021/0378752 A1 | 12/2021 | Paul et al. |
| 2021/0386437 A1 | 12/2021 | Dacosta et al. |
| 2021/0391058 A1 | 12/2021 | Kostrzewski et al. |
| 2021/0393304 A1 | 12/2021 | Geldwert |
| 2022/0039965 A1 | 2/2022 | Casey et al. |
| 2022/0087822 A1 | 3/2022 | Radermacher et al. |
| 2022/0096157 A1 | 3/2022 | Pollock et al. |
| 2022/0133484 A1 | 5/2022 | Lang |
| 2022/0160405 A1 | 5/2022 | Casey et al. |
| 2022/0167998 A1 | 6/2022 | Siccardi et al. |
| 2022/0192685 A1 | 6/2022 | Gazonnet et al. |
| 2022/0202495 A1 | 6/2022 | Pack |
| 2022/0211387 A1 | 7/2022 | Perler et al. |
| 2022/0233203 A1 | 7/2022 | Rhodes et al. |
| 2022/0249106 A1 | 8/2022 | Akallal et al. |
| 2022/0249143 A1 | 8/2022 | Hollis et al. |
| 2022/0270762 A1 | 8/2022 | Crawford et al. |
| 2022/0273450 A1 | 9/2022 | Steines et al. |
| 2022/0296285 A1 | 9/2022 | Besque et al. |
| 2022/0313284 A1 | 10/2022 | Korman |
| 2022/0323086 A1 | 10/2022 | Stemniski et al. |
| 2022/0338934 A1 | 10/2022 | Perler et al. |
| 2022/0346806 A1 | 11/2022 | Leemrijse et al. |
| 2022/0370211 A1 | 11/2022 | Campbell et al. |
| 2023/0013727 A1 | 1/2023 | Korman et al. |
| 2023/0014384 A1 | 1/2023 | Cordonnier et al. |
| 2023/0077222 A1 | 3/2023 | Awtrey |
| 2023/0157705 A1 | 5/2023 | Reynolds |
| 2023/0190306 A1 | 6/2023 | Kowalczyk et al. |
| 2023/0281842 A1 | 9/2023 | Ribeiro et al. |
| 2023/0310013 A1 | 10/2023 | Perler et al. |
| 2023/0310051 A1 | 10/2023 | Hafez et al. |
| 2023/0363773 A1 | 11/2023 | Perler et al. |
| 2023/0371966 A1 | 11/2023 | Spitler |
| 2023/0389937 A1 | 12/2023 | Penner et al. |
| 2023/0404673 A1 | 12/2023 | Spitler et al. |
| 2024/0005504 A1 | 1/2024 | Ribeiro et al. |
| 2024/0008880 A1 | 1/2024 | Spitler et al. |
| 2024/0099778 A1 | 3/2024 | Hlad et al. |
| 2024/0108414 A1 | 4/2024 | Dreyer et al. |

FOREIGN PATENT DOCUMENTS

| | | |
|---|---|---|
| AU | 2015203808 B2 | 9/2017 |
| AU | 2020220169 A1 | 9/2020 |
| AU | 2021286392 A1 | 1/2022 |
| CA | 2491824 A1 | 9/2005 |
| CA | 2608464 C | 7/2012 |
| CA | 2854997 A1 | 5/2013 |
| CA | 2713309 C | 7/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |

(56)          References Cited

FOREIGN PATENT DOCUMENTS

| | | | |
|---|---|---|---|
| CN | 204446081 | U | 7/2015 |
| CN | 106236185 | A | 12/2016 |
| CN | 205924106 | U | 2/2017 |
| CN | 206151532 | U | 5/2017 |
| CN | 105105853 | B | 7/2017 |
| CN | 108030532 | A | 5/2018 |
| CN | 207721902 | U | 8/2018 |
| CN | 112914724 | B | 2/2022 |
| CN | 117297772 | B | 2/2024 |
| CN | 117322951 | B | 2/2024 |
| CN | 109223098 | B | 5/2024 |
| DE | 2910627 | A1 | 9/1980 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124832 | B1 | 8/2012 |
| EP | 2750617 | A1 | 7/2014 |
| EP | 2856951 | A1 | 4/2015 |
| EP | 2624764 | B1 | 12/2015 |
| EP | 3000443 | A3 | 7/2016 |
| EP | 2083758 | B1 | 11/2017 |
| EP | 2632349 | B1 | 3/2018 |
| EP | 3013256 | B1 | 11/2018 |
| EP | 3171795 | B1 | 11/2018 |
| EP | 3672535 | A1 | 7/2020 |
| EP | 2558010 | B1 | 5/2021 |
| EP | 3948895 | A1 | 2/2022 |
| EP | 3740141 | B1 | 4/2022 |
| EP | 2844162 | B1 | 7/2022 |
| FR | 2362616 | A1 | 3/1978 |
| FR | 2764183 | A1 | 12/1998 |
| FR | 2953120 | B1 | 1/2012 |
| FR | 3030221 | A1 | 6/2016 |
| FR | 3117328 | B1 | 3/2023 |
| GB | 2154143 | A | 9/1985 |
| GB | 2154144 | A | 9/1985 |
| GB | 2334214 | B | 1/2003 |
| GB | 2589960 | A | 6/2021 |
| JP | S635739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| KR | 1020160090006 | A | 7/2016 |
| KR | 1020180118476 | A | 10/2018 |
| KR | 101952368 | B1 | 2/2019 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| RU | 2789960 | C2 | 2/2023 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009001083 | A1 | 12/2008 |
| WO | 2009029798 | A1 | 3/2009 |
| WO | 2009032101 | A2 | 3/2009 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012176077 | A1 | 12/2012 |
| WO | 2013026786 | A1 | 2/2013 |
| WO | 2013041618 | A1 | 3/2013 |
| WO | 2013134387 | A1 | 9/2013 |
| WO | 2013156816 | A2 | 10/2013 |
| WO | 2014020561 | A1 | 2/2014 |
| WO | 2014020562 | A1 | 2/2014 |
| WO | 2014022055 | A1 | 2/2014 |
| WO | 2014085882 | A1 | 6/2014 |
| WO | 2014147099 | A1 | 9/2014 |
| WO | 2014152219 | A2 | 9/2014 |
| WO | 2014200017 | A1 | 12/2014 |
| WO | 2015003284 | A2 | 1/2015 |
| WO | 2015094409 | A1 | 6/2015 |
| WO | 2015127515 | A2 | 9/2015 |
| WO | 2016012731 | A1 | 1/2016 |
| WO | 2016102025 | A1 | 6/2016 |
| WO | 2017031000 | A1 | 2/2017 |
| WO | 2017122076 | A2 | 7/2017 |
| WO | 2017151833 | A1 | 9/2017 |
| WO | 2018167369 | A1 | 9/2018 |
| WO | 2019060780 | A2 | 3/2019 |
| WO | 2019052622 | A4 | 5/2019 |
| WO | 2019180747 | A1 | 9/2019 |
| WO | 2020060349 | A1 | 3/2020 |
| WO | 2021054518 | A1 | 3/2021 |
| WO | 2021091071 | A1 | 5/2021 |
| WO | 2021118733 | A1 | 6/2021 |
| WO | 2021127625 | A1 | 6/2021 |
| WO | 2021240290 | A1 | 12/2021 |
| WO | 2022155208 | A1 | 7/2022 |
| WO | 2022182312 | A1 | 9/2022 |
| WO | 2023096516 | A1 | 6/2023 |
| WO | 2024025840 | A1 | 2/2024 |

OTHER PUBLICATIONS

Whipple et al., "Zimmer Herbert Whipple Bone Screw System: Surgical Techniques for Fixation of Scaphoid and Other Small Bone Fractures," Zimmer, 2003, 59 pages.

Weber et al., "A Simple System for Navigation of Bone Alignment Osteotomies of the Tibia," International Congress Series, vol. 1268, Jan. 2004, pp. 608-613, (Abstract Only).

Wukich et al., "Hypermobility of the First Tarsometatarsal Joint," Foot and Ankle Clinics, vol. 10, No. 1, Mar. 2005, pp. 157-166.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fuchirurgie Das V-tek-System," ABW Wissenschaftsverlag GmbH, 2009, 11 pages, including English Abstract.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wienke et al., "Bone Stimulation For Nonunions: What the Evidence Reveals," Podiatry Today, vol. 24, No. 9, Sep. 2011, pp. 52-57.

Williams et al., "Metatarsus adductus: Development of a non-surgical treatment pathway," Journal of Paediatrics and Child Health, vol. 49, 2013, pp. E428-433.

Yasuda et al., "Proximal Supination Osteotomy of the First Metatarsal for Hallux Valgus," Foot and Ankle International, vol. 36, No. 6, Jun. 2015, pp. 696-704.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

(56)            References Cited

OTHER PUBLICATIONS

Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.

Wright Medical, "How BLUEPRINT Works—from CT to 3D [Caw -9389]", https://www.wrightmeded. com/videos/how-blueprint-works-from-ct-to-3d-caw-9389, video time Mar. 32 seconds to 48 seconds, Dated May 26, 2022.

European Patent Office, "Extended European Search Report and Written Opinion", From Application No. 20862480.9, Dated Sep. 4, 2023, pp. 8.

International Searching Authority, "International Preliminary Report on Patentability and Written Opinion", From Application No. PCT/US2020/050764, Mailed Dec. 17, 2020, pp. 9.

"Foot and Ankle Instrument Set," Smith & Nephew, 2013, 2 pages.

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

ACUMED "Acumed Osteotomy System" with partial English Translation, 2014, pp. 19.

Additive Orthopaedics, "The First and Only FDA Approved Patient Specific Talus Spacer" , https://totaltalusreplacement.com, Downloaded: Mar. 4, 2022, pp. 11.

Aiyer et al. "Prevalence of Metatarsus Adductus in Patients Undergoing Hallux Valgus Surgery" Foot & Ankle International 2014, vol. 35(12), pp. 1292-1297.

Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.

Alvine et al. "Peg and Dowel Fusion of the Proximal Interphalangeal Joint" Foot & Ankle vol. 1, No. 2, 1980 American Orthopaedic Foot Society, pp. 5.

ARTHREX "Chevron Osteotomy" https://www.arthrex.com/foot-ankle/chevron-osteotomy, Retrieved Nov. 30, 2022, pp. 7.

ARTHREX "Comprehensive Foot System" https://www.arthrex. com/resources/animation/8U3iaPvY6kO8bwFAwZF50Q/comprehensive-foot-system?referringTeam=foot_and_ankle, Published Aug. 27, 2013, pp. 3.

ARTHREX, "Distal Tibia Allograft Workstation for Glenoid Bone Loss, Surgical Technique" Arthrex.com, 2018, pp. 8.

Baravarian, "Why the Lapidus Procedure is Ideal for Bunions" Podiatry Today, https://www.hmpgloballearningnetwork.com/site/podiatry/article/5542, May 2006 pp. 8.

Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.

Bednarz et al. "Modified Lapidus Procedure for the Treatment of Hypermobile Hallux Valgus" Foot & Ankle, American Orthopaedic Foot & Ankle Society, 2000, pp. 6.

Bennett et al. "Intraosseous Sliding Plate Fixation Used in Double Osteotomy Bunionectomy" Foot & Ankle International, 2019, vol. 40(1), pp. 85-88.

BIOPRO "Accu-Cut Osteotomy Guide System Accurate and consistent hallux valgus correction" Document Dates Sep. 16, 2019, pp. 2.

Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.

Bouaicha et al. "Fixation of Maximal Shift Scarf Osteotomy with Inside-Out Plating: Technique Tip" Foot & Ankle International, vol. 32, No. 5, May 2011, pp. 567-569.

Buda et al. "Effect of Fixation Type and Bone Graft on Tarsometatarsal Fusion" Foot & Ankle International 2018, vol. 39(12), pp. 1394-1402.

Carr et al. "Correctional Osteotomy for Metatarsus Primus Varus and Hallux Valgus*" The Journal of Bone and Joint Surgery, vol. 50-A, No. 7, Oct. 1968, pp. 1353-1367.

Catanese et al. "Measuring Sesamoid Position in Hallux Valgus When Is the Sesamoid Axial View Necessary?" Foot & Ankle Specialist, Downloaded Aug. 15, 2016, pp. 1-3.

Chesser et al. "New Advances With The Tarsometatarsal" Podiatry Today, vol. 30, Issue 10, Oct. 2017, pp. 28-36.

Chomej et al. "Lateralising Dmmo (Mis) for simultaneous correction of a pes adductus during surgical treatment of a hallux valgus" Journal Pre-proof, The Foot, Accepted Jul. 16, 2020, pp. 33.

Cichero et al. "Different fixation constructs and the risk of nonunion following first metatarsophalangeal joint arthrodesis" Foot and Ankle Surgery, 27, 2021, Accepted Oct. 15, 2020, pp. 789-792.

Coetzee et al., "Revision Hallux Valgus Correction," Operative Techniques in Foot and Ankle Surgery, Section I, Chapter 15, 2011, pp. 84-96.

Collan et al., "The biomechanics of the first metatarsal bone in hallux valgus: A preliminary study utilizing a weight bearing extremity CT," Foot and Ankle Surgery, vol. 19, 2013, pp. 155-161.

"Futura Forefoot Implant Arthroplasty Products," Tornier, Inc., 2008, 14 pages.

"Hat-Trick Lesser Toe Repair System, Foot and Ankle Technique Guide, Metatarsal Shortening Osteotomy Surgical Technique," Smith & Nephew, 2014, 16 pages.

"Hat-Trick Lesser Toe Repair System," Smith & Nephew, Brochure, Aug. 2014, 12 pages.

"Hoffmann II Compact External Fixation System", Stryker, Brochure, Literature No. 5075-1-500, 2006, 12 pages.

"Hoffmann II Micro Lengthener", Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Patient to Patient Precision, Accu-Cut, Osteotomy Guide System, BioPro, Foot & Ankle International Journal, vol. 23, No. 8, Aug. 2002, 2 pages.

Blomer "Problems and complications of knee endoprostheses from a manufacturer's point of view Orthopade 200, 29, pp. 688-696, English Abstract."

"Prophecy Inbone Preoperative Navigation Guides", Wright Medical Technology, Inc., Nov. 2013, 6 pages.

"Rayhack Ulnar Shortening Generation II Low-Profile Locking System Surgical Technique," Wright Medical Technology, Inc., Dec. 2013, 20 pages.

Smith & Nephew scores a Hat-Trick with its entry into the high-growth hammer toe repair market, Smith & Nephew, Jul. 31, 2014, 2 pages.

"Lag Screw Target Bow," Stryker Leibinger GmbH & Co. KG, Germany 2004, 8 pages.

Anderson et al., "Uncemented STAR Total Ankle Protheses" Journal of Bone Joint Surgery America, Sep. 2004, Abstract of Article, pp. 6.

Coetzee et al., "The Lapidus Procedure: A Prospective Cohort Outcome Study," Foot & Ankle International, vol. 25, No. 8, Aug. 2004, pp. 526-531.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

(56)                    References Cited

OTHER PUBLICATIONS

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods, " issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
D'Amico et al., "Motion of the First Ray: Clarification Through Investigation," Journal of the American Podiatry Association, vol. 69, No. 1, Jan. 1979, pp. 17-23.
Dayton et al., "Biwinged Excision for Round Pedal Lesions," The Journal of Foot and Ankle Surgery, vol. 35, No. 3, 1996, pp. 244-249.
Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, pp. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane

(56)                    References Cited

OTHER PUBLICATIONS

Tarsal Metatarsal Joint Arthrodesis" The Journal of Foot & Ankle Surgery 56, 2017, pp. 1041-1046.

Dayton "Evidence-Based Bunion Surgery: A Critical Examination of Current and Emerging Concepts and Techniques" Springer International Publishing, 2017, pp. 254.

Dayton et al. "Biomechanical Characteristics of Biplane Multiplanar Tension-Side Fixation for Lapidus Fusion" The Journal of Foot & Ankle Surgery, 2018, pp. 1-5.

Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Conti et al., "Effect of the Modified Lapidus Procedure for Hallux Valgus on Foot Width," Foot & Ankle International, Feb. 1, 2020, published online: Oct. 30, 2019, 6 pages.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Dayton et al. "Comparison of Radiographic Measurements Before and After Triplane Tarsometatarsal Arthrodesis for Hallux Valgus" The Journal of Foot & Ankle Surgery 59, 2020, pp. 291-297.

Curran et al. "Functional Capabilities After First Metatarsal Phalangeal Joint Arthrodesis Using a Locking Plate and Compression Screw Construct" The Journal of Foot & Ankle Surgery, 2021, pp. 1-5.

De Carvalho, et al. "Automated Three-dimensional distance and coverage mapping of hallux valgus: a case- control study" Journal of Foot and Ankle, 2022; 16(1), pp. 5.

Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series And Critical Review of the Literature," The Journal of Foot and Ankle Surgery, vol. 52, No. 3, May/Jun. 2013, pp. 348-354.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

De Heer et al., "Procedure-Specific Hardware Removal After Evans Osteotomy" Journal of the American Podiatric Medical Association, vol. 110, No. 2, Mar./Apr. 2020, pp. 1-7.

DeCarbo et al., "Locking Plates: Do They Prevent Complications?," Podiatry Today, Apr. 2014, 7 pages.

DeCarbo et al., "Resurfacing Interpositional Arthroplasty for Degenerative Joint Disease of the First Metatarsalphalangeal Joint," Podiatry Management, Jan. 2013, pp. 137-142.

Decarbo et al., "The Weil Osteotomy: A Refresher," Techniques in Foot and Ankle Surgery, vol. 13, No. 4, Dec. 2014, pp. 191-198.

Defendant Fusion Orthopedics LLC's Invalidity Contentions, No. CV-22-00490-PHX-SRB, US District Court for the District of Arizona, Aug. 27, 2022, 41 pages.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.

Dinapoli et al., "Metatarsal Osteotomy for the Correction of Metatarsus Adductus," Reconstructive Surgery of the Foot and Leg, 1989, pp. 242-250.

Disior, "Bonelogic Foot & Ankle Module" , https://www.disior.com/foot--ankle.html, Downloaded Jun. 1, 2022, p. 6.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Easley et al., "What is the Best Treatment for Hallux Valgus?," Evidence-Based Orthopaedics—The Best Answers to Clinical Questions, Chapter 73, 2009, pp. 479-491.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Eustace et al., "Hallux valgus, first metatarsal pronation and collapse of the medial longitudinal arch—a radiological correlation," Skeletal Radiology, vol. 23, 1994, pp. 191-194.

Fallin et al., US Provisional Application Entitled Indexed Tri-Planar Osteotomy Guide and Method, U.S. Appl. No. 62/118,378, filed Feb. 19, 2015, 62 pages.

Fazal et al., "First metatarsophalangeal joint arthrodesis with two orthogonal two hole plates," Acta Orthopaedica et Traumatologica Turcica, vol. 52, 2018, pp. 363-366.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Ferrari et al., "A Radiographic Study of the Relationship Between Metatarsus Adductus and Hallux Valgus," The Journal of Foot and Ankle Surgery, vol. 42, No. 1, 2003, pp. 9-14.

Ferreyra et al., "Can we correct first metatarsal rotation and sesamoid position with the 3D Lapidus procedure?," Foot and Ankle Surgery, vol. 28, No. 3, Apr. 2022, pp. 313-318.

Fibretuff, "3D Printing, CNC Machining, Molding and Extruding Biocompatible material's with "bone like" Qualities for 3D Printing" https://fibretuff.us, Downloaded Feb. 24, 2023, pp. 22.

Fishco, "A Straightforward Guide to the Lapidus Bunionectomy, " Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

(56) References Cited

OTHER PUBLICATIONS

Flavin et al., "Arthrodesis of the First Metatarsophalangeal Joint Using a Dorsal Titanium Contoured Plate," Foot & Ankle International, vol. 25, No. 11, Nov. 2004, pp. 783-787.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fraissler et al., "Treatment of hallux valgus deformity," Efort Open Reviews, vol. 1, Aug. 2016, pp. 295-302.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Ghali et al., "The Management of Metatarsus Adductus et Supinatus," The Journal of Bone and Joint Surgery, vol. 66-B, No. 3, May 1984, pp. 376-380.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fr die Knieendoprothetik," Forschungsberichte, Technische Universitat Munchen, 165, 2002, 11 pages, including partial English Translation.

Gould et al., "A Prospective Evaluation of First Metatarsophalangeal Fusion Using an Innovative Dorsal Compression Plating System," The Journal of Foot & Ankle Surgery, vol. 60, 2021, pp. 891-896.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

Groves, "Operative Report," St. Tammany Parish Hospital, Date of Procedure, Mar. 26, 2014, 2 pages.

Gutteck et al., "Comparative study of Lapidus bunionectomy using different osteosynthesis methods," Foot and Ankle Surgery, vol. 19, 2013, pp. 218-221.

Gutteck et al., "Is it feasible to rely on intraoperative X ray in correcting hallux valgus?," Archives of Orthopaedic and Trauma Surgery, vol. 133, 2013, pp. 753-755.

Hardy et al., "Observations on Hallux Valgus," The Journal of Bone and Joint Surgery, vol. 33B, No. 3, Aug. 1951,pp. 376-391.

Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.

Hatch et al., "Triplane Hallux Abducto Valgus Classification," The Journal of Foot & Ankle Surgery, vol. 57, No. 5, September/Oct. 2018, published online: May 18, 2018, pp. 972-981.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Ho et al., "Hallux rigidus," Efort Open Reviews, vol. 2, Jan. 2017, pp. 13-20.

Tricot et al., "3D-corrective osteotomy using surgical guides for posttraumatic distal humeral deformity," Acta Orthopaedica Belgica, vol. 78, No. 4, 2012, pp. 538-542.

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D Med, "Anatomical Model: Calcaneus" , 2022, pp. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, " Cuboid Suspension in Charcot Reconstruction. Using 3D Imaging for Planning, Printing and Execution for Complex Deformity Correction" Downloaded Apr. 2021, pp. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Santrock et al., "Hallux Valgus Deformity and Treatment: A Three-Dimensional Approach: Lapiplasty," Foot & Ankle Clinics, vol. 23, No. 2, 2018, pp. 281-295.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

(56) References Cited

OTHER PUBLICATIONS

Schon et al., "Cuneiform-Metatarsal Arthrodesis for Hallux Valgus," The Foot and Ankle, Second Edition, Chapter 8, 2002, pp. 99-117.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Shima et al., "Operative Treatment for Hallux Valgus With Moderate to Severe Metatarsus Adductus," Foot & Ankle International, vol. 40, No. 6, 2019, pp. 641-647.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith et al., "Intraoperative Multiplanar Alignment System to Guide Triplanar Correction of Hallux Valgus Deformity," Techniques in Foot & Ankle Surgery, 2017, 8 pages.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Smith et al., "Understanding Frontal Plane Correction in Hallux Valgus Repair," Clinics in Podiatric Medicine and Surgery, vol. 35, 2018, pp. 27-36.

Sokoloff, "Lapidus Procedure," Textbook of Bunion Surgery, Chapter 15, 1981, pp. 277-287.

Stableloc External Fixation System, Acumed, Product Overview, Effective date Sep. 2015, 4 pages.

Stahl et al., "Derotation of Post-Traumatic Femoral Deformities by Closed Intramedullary Sawing," Injury, vol. 37, No. 2, Feb. 2006, pp. 145-151, (Abstract Only).

Stamatis et al., "Mini Locking Plate as Medial Buttress for Oblique Osteotomy for Hallux Valgus," Foot & Ankle International, vol. 31, No. 10, Oct. 2010, pp. 920-922.

Stryker, "PROstep Minimally Invasive Surgery" https://www.stryker.com/US/en/foot-and-ankle/products/prostep.html, Downloaded Jun. 23, 2023, pp. 10.

Synergy 3D Med, "Anatomical Model: Calcaneus" Downloaded Mar. 2, 2023, pp. 2.

Synopsys, "Medical Image Segmentation with Machine Learning—Simpleware Automated Solution Modules" , https://www.synopsys.com/simpleware/software/auto-segmenter-modules.html#simpleware-as-ortho, 2022, pp. 12.

Talbot et al., " Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tornier Technology, "Tornier Blueprint 3D Planning + PSI" , https://www.wrightemedia.com/ProductFiles/Files/PDFs/CAW-8609_EN_HR_LE.pdf, Feb. 2017, p. 12.

Total Ankle Institute, "Prophecy: Preoperative Navigation Guides" , https://www.totalankleinstitute.com/infinity-products/prophecy-preoperative-navigation-guides/, 2019, pp. 6.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Treace "FastGrafter Autograft Harvesting System" Downloaded from https://www.lapiplasty.com/surgeons/other-products/fastgrafter/, Dec. 4, 2024, pp. 8.

Treace Medical Concepts, "Adductoplasty Midfoot Correction System", https://www.lapiplasty.com/surgeons/other-products/adductoplasty-system/, Downloaded May 2, 2022, pp. 9.

Use for BME Speed Nitinol Staple Fixation for the Lapidus Procedure, "date unknown, 1 page."

Virzi et al. "Comprehensive Review of 3D Segmentation Software Tools for MRI Usable for Pelvic Surgery Planning", Journal of Digital Imaging (2020) 33, pp. 99-110.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

Hunt et al., "Locked Versus Nonlocked Plate Fixation for Hallux MTP Arthrodesis," Foot and Ankle International, vol. 32, No. 7, Jul. 2011, pp. 704-709.

Integra, "Integra Large Qwix Positioning and Fixation Screw, Surgical Technique," 2012, 16 pages.

Jackson III et al., "The Surgical Learning Curve for Modified Lapidus Procedure for Hallux Valgus Deformity," Foot & Ankle Specialist, Jul. 2021, 5 pages.

Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.

KLS Martin Group, "Individual Patient Solutions IPS Implants" , https://www.klsmartin.com/en-na/products/ individual-patient-solutions/ips-implants/, Downloaded: Jun. 1, 2022, pp. 8.

Kurup et al., "Midfoot arthritis—current concepts review," Journal of Clinical Orthopaedics and Trauma, vol. 11, 2020, pp. 399-405.

La Reaux et al., "Metatarsus adductus and hallux abducto valgus: their correlation," The Journal of Foot Surgery, vol. 26, No. 4, Jul. 1987, pp. 304-308, Abstract Only.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

Latif et al., "First metatarsophalangeal fusion using joint specific dorsal plate with interfragmentary screw augmentation: Clinical and radiological outcomes," Foot and Ankle Surgery, vol. 25, 2019, pp. 132-136.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

Little, "Joint Arthrodesis For Hallux Valgus," Clinics in Podiatric Medicine and Surgery, Hallux Abducto Valgus Surgery, updated

(56)          References Cited

OTHER PUBLICATIONS

Apr. 19, 2014, retrieved online from < https://www.footankleinstitute.
com/first-metatarsophalangeal-joint-arthrodesis-in-the-treatment-of-
hallux-valgus>, 7 pages.
Lopez et al., "Metatarsalgia: Assessment Algorithm and Decision
Making," Foot and Ankle Clinics, vol. 24, No. 4, Dec. 2019,
published online: Sep. 25, 2019, pp. 561-569.
MAC (Multi Axial Correction) Fixation System, Biomet Trauma,
retrieved Dec. 19, 2014, from the Internet: < http://footandanklefixation.
com/product/biomet-trauma-mac-multi-axial-correction-fixation-
system>, 7 pages.
Machacek Jr. et al., "Salvage of a Failed Keller Resection Arthroplasty,"
The Journal of Bone and Joint Surgery, vol. 86A, No. 6, Jun. 2004,
pp. 1131-1138.
Magin, "Computernavigierter Gelenkersatz am Knie mit dem
Orthopilot," Operative Orthopdie und Traumatologie, vol. 22, No.
1, 2010, pp. 63-80, including English Abstract on p. 64.
Magin, "Die belastungsstabile Lapidus-Arthrodese bei Hallux-
valgus-Deformitt mittels IVP-Plattenfixateur (V-TEK-System)," Opera-
tive Orthopdie und Traumatologie, vol. 26, No. 2, 2014, pp.
184-195, including English Abstract on p. 186.
Marshall et al., "The identification and appraisal of assessment tools
used to evaluate metatarsus adductus: a systematic review of their
measurement properties," Journal of Foot and Ankle Research, vol.
11, No. 25, 2018, 10 pages.
McAleer et al., "A systematic approach to the surgical correction of
combined hallux valgus and metatarsus adductus deformities," The
Journal of Foot & Ankle Surgery, May 21, 2021, 6 pages.
McAleer et al., "Radiographic Outcomes Following Triplanar Cor-
rection of Combined Hallux Valgus and Metatarsus Adductus
Deformities," ACFAS Scientific Conference, Poster, Feb. 2022, 1
page.
McCabe et al., "Anatomical reconstruction of first ray instability
hallux valgus with a medial anatomical TMTJ1 plate," Foot and
Ankle Surgery, vol. 27, No. 8, Dec. 2021, pp. 869-873.
Mehtar et al., "Outcomes of bilateral simultaneous hallux MTPJ
fusion," Foot and Ankle Surgery, vol. 27, 2021, pp. 213-216.
Michelangelo Bunion System, Surgical Technique ", Instratek Incor-
porated, publication date unknown, 4 pages."
Miller et al., "Variable Angle Locking Compression Plate as Alter-
native Fixation for Jones Fractures: A Case Series," Kansas Journal
of Medicine, vol. 12, No. 2, May 2019, pp. 28-32.
Mini Joint Distractor, Arthrex, retrieved Dec. 19, 2014, from the
Internet: <http://www.arthrex.com/foot-ankle/mini-joint-distractor/
products>, 2 pages.
MiniRail System, Small Bone Innovations, Surgical Technique,
2010, 24 pages.
Miyake et al., "Three-Dimensional Corrective Osteotomy for Malunited
Diaphyseal Forearm Fractures Using Custom-Made Surgical Guides Based on Computer Simulation," JBJS Essential Surgical Tech-
niques, vol. 2, No. 4, 2012, 11 pages.
Mizuno et al., "Detorsion Osteotomy of the First Metatarsal Bone
in Hallux Valgus," Japanese Orthopaedic Association, Tokyo, 1956;
30:813-819.
Modular Rail System: External Fixator, Smith & Nephew, Surgical
Technique, 2013, 44 pages.
Monnich et al., "A Hand Guided Robotic Planning System for Laser
Osteotomy in Surgery," World Congress on Medical Physics and
Biomedical Engineering vol. 25/6: Surgery, Nimimal Invasive Inter-
ventions, Endoscopy and Image Guided Therapy, Sep. 7-12, 2009,
pp. 59-62, (Abstract Only).
Moore et al., "Effect of Ankle Flexion Angle on Axial Alignment of
Total Ankle Replacement," Foot and Ankle International, vol. 31,
No. 12, Dec. 2010, pp. 1093-1098, (Abstract Only).
Mortier et al., "Axial Rotation of the First Metatarsal Head in a
Normal Population and Hallux Valgus Patients," Orthopaedics and
Traumatology: Surgery and Research, vol. 98, 2012, pp. 677-683.
Mote et al., "First Metatarsal-Cuneiform Arthrodesis for the Treat-
ment of First Ray Pathology: A Technical Guide," JFAS Techniques
Guide, vol. 48, No. 5, Sep./Oct. 2009, pp. 593-601.
Musculoskeletal Key "Arthrodesis of the Tarsmetatarsal Joint"
https://musculoskeletalkey.com/arthrodesis-of-the-tarsometatarsal-
joint/, Retrieved May 8, 2020, pp. 11.
Myerson, "Cuneiform-Metatarsal Arthrodesis," The Foot and Ankle,
Chapter 9, 1997, pp. 107-117.
Nagy et al., "The AO Ulnar Shortening Osteotomy System Indica-
tions and Surgical Technique," Journal of Wrist Surgery, vol. 3, No.
2, 2014, pp. 91-97.
NexFix from Nexa Orthopedics, MetaFix I from Merete Medical,
Inc. and The BioPro Lower Extremities from BioPro, found in Foot
& Ankle International Journal, vol. 28, No. 1, Jan. 2007, 4 pages.
Nix et al., "Prevalence of hallux valgus in the general population:
a systematic review and meta-analysis," Journal of Foot and Ankle
Research, vol. 3, No. 21, 2010, 9 pages.
Novastep, "Pecaplasty Percutaneous Bunion Correction" Down-
loaded Jun. 29, 2022, pp. 24.
Novastep, "Pecaplasty Percutaneous Bunion Correction- Brochure
Pecaplasty Targeting Guide" Downloaded Dec. 15, 2021, pp. 4.
Odenbring et al., "A guide instrument for high tibial osteotomy,"
Acta Orthopaedica Scandinavica, vol. 60, No. 4, 1989, pp. 449-451.
Okuda et al., "Proximal Metatarsal Osteotomy for Hallux Valgus:
Comparison of Outcome for Moderate and Severe Deformities,
Foot and Ankle International," vol. 29, No. 7, Jul. 2008, pp.
664-670.
Instratek, "Michelangelo Bunion System, Surgical Technique", Instratek
Incorporated, publication date unknown, 4 pages.
Marc-Olivier Gauci, "Patient-specific guides in orthopedic surgery,"
Orthopaedics & Traumatology: Surgery & Research 108, 2021, 10
pages.

\* cited by examiner

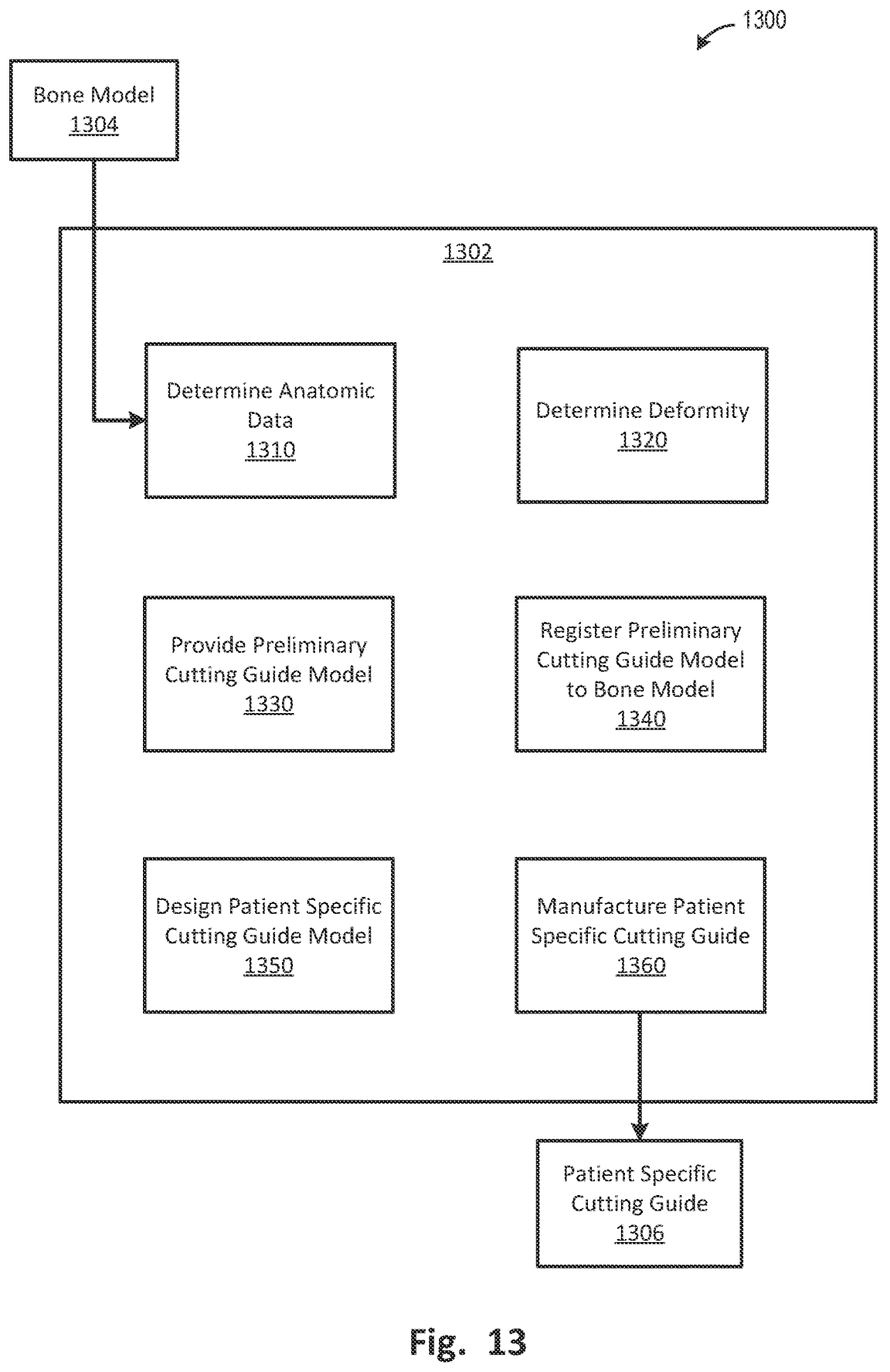

Bone Model
1304

1302

Determine Anatomic
Data
1310

Determine Deformity
1320

Provide Preliminary
Cutting Guide Model
1330

Register Preliminary
Cutting Guide Model
to Bone Model
1340

Design Patient Specific
Cutting Guide Model
1350

Manufacture Patient
Specific Cutting Guide
1360

Patient Specific
Cutting Guide
1306

Fig. 13

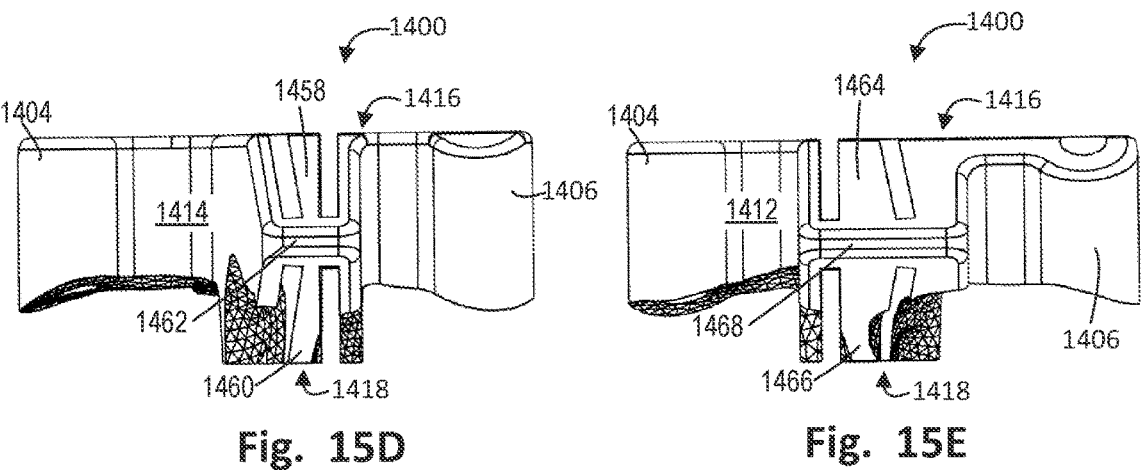
Fig. 15D                    Fig. 15E
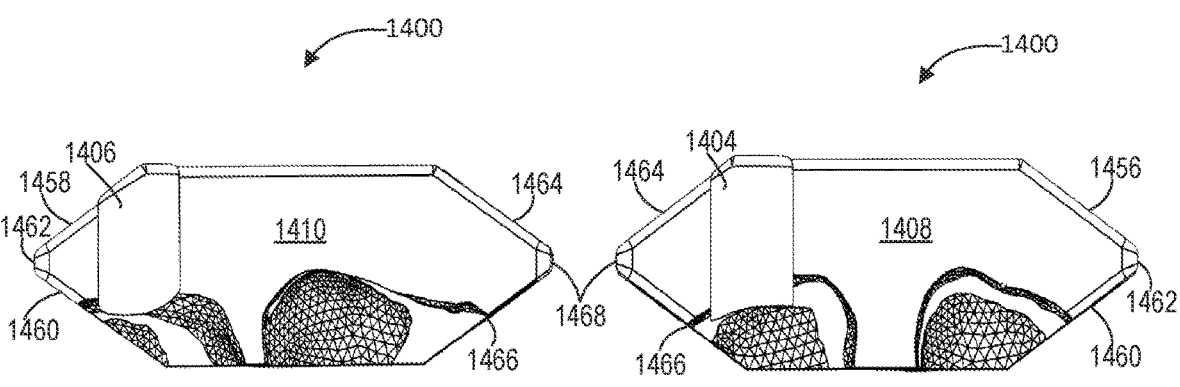
Fig. 15F                    Fig. 15G

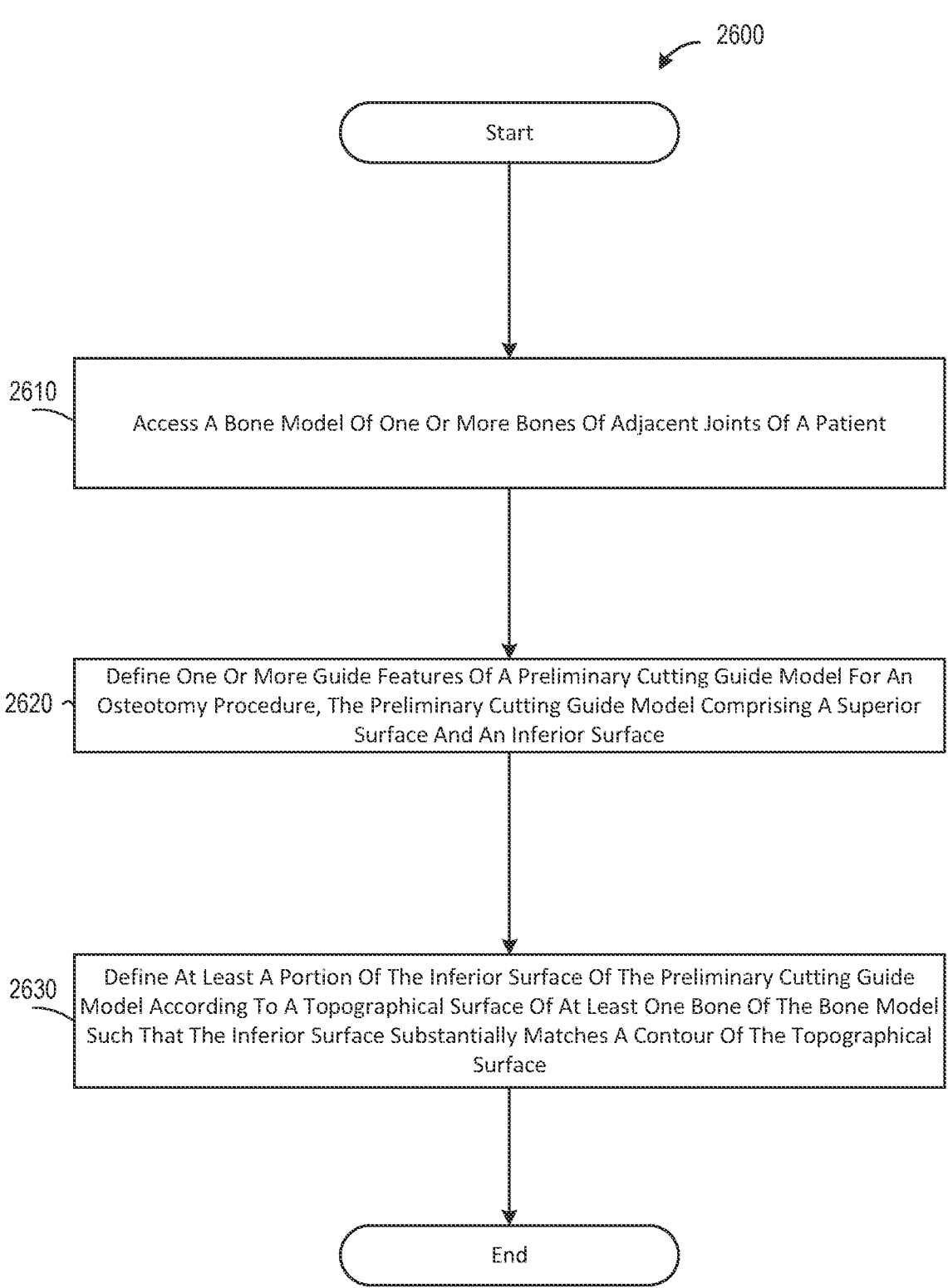

2600

Start

2610    Access A Bone Model Of One Or More Bones Of Adjacent Joints Of A Patient 2620    Define One Or More Guide Features Of A Preliminary Cutting Guide Model For An Osteotomy Procedure, The Preliminary Cutting Guide Model Comprising A Superior Surface And An Inferior Surface 2630    Define At Least A Portion Of The Inferior Surface Of The Preliminary Cutting Guide Model According To A Topographical Surface Of At Least One Bone Of The Bone Model Such That The Inferior Surface Substantially Matches A Contour Of The Topographical Surface End

Fig. 26

PATIENT-SPECIFIC OSTEOTOMY INSTRUMENTATION

CROSS-REFERENCE TO RELATED APPLICATIONS

This application is a continuation of U.S. patent application Ser. No. 17/832,594 filed on Jun. 4, 2022, entitled "PATIENT-SPECIFIC OSTEOTOMY INSTRUMENTATION" which is hereby incorporated by reference in its entirety.

TECHNICAL FIELD

The present disclosure relates to surgical devices, systems, instruments, and methods. More specifically, the present disclosure relates to patient-specific osteotomy guides and methods of designing, fabricating, and using the same.

BACKGROUND

Various bone conditions may be corrected using an osteotomy, in which one or more bones are cut, replaced, and/or reoriented. Osteotomies can be performed on bones at or near a joint, at or near a head or base of a bone, along the metaphyseal region, epiphysis region, or diaphyseal region, or anywhere along a bone of a patient. Traditionally, resection for the osteotomies has been done manually by a skilled surgeon.

Unfortunately, manual resection may not form desired, or optimal cuts, at desired angles for a given procedure. Manual resection for osteotomies includes a risk of an improper cut, inadvertent cuts to surrounding tissues, and/or more cuts than necessary for a given surgical procedure. Cutting guides have been developed to address some of these risks, with some osteotomies, for some procedures. Cutting guides can help a surgeon properly locate, position, and make one or more cuts. Unfortunately, many cutting guides are not patient-specific, and can therefore be difficult to properly position to perform the osteotomy on a specific patient. As a result, many known osteotomy procedures with such conventional cutting guides can carry risk of an improper cut that fails to correct the underlying condition, or even endangers surrounding tissues.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include a patient-specific instrument for performing an osteotomy on a patient. The patient-specific instrument can include a body which may include: a proximal side, a distal side, a medial side, a lateral side and a superior side. The body may include an inferior side which may include a bone engagement surface shaped to match at least one of a first surface of a first bone, a second surface of a second bone, a third surface of a third bone, and a fourth surface of a fourth bone of adjacent joints; and one or more guide features that together, with the bone engagement surface overlying both adjacent joints, are positioned to guide resection of at least one of the first bone, the second bone, the third bone, and the fourth bone during the osteotomy. The instrument includes at least one anchor feature coupled to the body and configured to receive one or more fasteners to anchor the body to one or more bones of a patient; and where the body is configured to seat transverse to the adjacent joints with the bone engagement surface engaging at least one of the first surface, the second surface, the third surface, and the fourth surface.

Implementations may include one or more of the following features. The patient-specific instrument may include a bone engagement surface where the bone engagement surface is shaped to match at least one of the first surface, the second surface, the third surface, and the fourth surface. The bone engagement surface may further include a registration key configured to fit between bones of the adjacent joints. The registration key may include at least one of: a proximal projection; a distal projection; and a midsection projection between the proximal projection and the distal projection.

The bone engagement surface further may include: a first proximal bone recess; a second proximal bone recess; a first distal bone recess; a second distal bone recess; where the first proximal bone recess is opposite the first distal bone recess and the second proximal bone recess is opposite the second distal bone recess. In one aspect, a first anchor feature of the two or more anchor features extends from the proximal side of the body such that the first anchor feature is dorsal to one of the first bone and the third bone; and a second anchor feature of the two or more anchor features extends from the distal side of the body such that the second anchor feature is dorsal to one of the second bone and the fourth bone. Of course, an anchor feature of the one or more or two or more anchor features may extend from a side of the body in directions other than dorsal to one or more of the first bone, the second bone, the third bone, and/or the fourth bone. For example, an anchor feature may also extend from a side of the body dorsomedially, dorsolaterally, or the like.

A first proximal bone recess of the bone engagement surface may include an inferior surface of a first anchor feature and where a second distal bone recess of the bone engagement surface may include an inferior surface of a second anchor feature. In one aspect, the one or more guide features may include: a first guide feature configured to traverse a first joint and a second joint of the adjacent joints; a second guide feature configured to traverse one of the first joint and the second joint; and a third guide feature configured to traverse the other one of the first joint and the second joint not traversed by the second guide feature. At least one of the one or more guide features may include a position and an orientation, at least one of which is based on patient imaging data. At least one of the one or more guide features may include a stop that may include a maximum depth defined using patient imaging data, the stop may be configured to limit a cutting tool to the maximum depth.

One general aspect of the present disclosure can include a patient-specific instrument for correcting an osteotomy on a patient. The patient-specific instrument may include a body may include: a proximal side, a distal side, a medial side, and a lateral side; an inferior side may include a plurality of bone engagement surfaces each shaped to correspond to at least a portion of a surface topography of at least one bone of adjacent joints; a superior side may include at least three guide features configured receive a cutting tool and to guide resection of at least three bones of the adjacent joints during the osteotomy. The instrument includes one or more anchor features extending from the body and configured to anchor the body to one or more bones of the adjacent joints; and where the body is configured to seat transverse to the adjacent joints with the plurality of bone engagement surfaces engaging bones of the adjacent joints.

Implementations may include one or more of the following features. The patient-specific instrument may include a body that may include a longitudinal axis and at least one of the at least three guide features may be oriented within the body at a first angle in relation to the longitudinal axis. At least one of the at least three guide features may extend through the body at a second angle in relation to a longitudinal axis of a bone of the adjacent joints.

At least one of the first angle and the second angle are defined based on, or determined by, patient imaging data. The medial side of the body may include a medial superior surface and a medial inferior surface that meet at a medial edge, the medial inferior surface angled to connect the inferior side of the body and the medial edge such that the medial inferior surface does not impinge upon soft tissue near at least one joint of the adjacent joints.

The lateral side of the body may include a lateral superior surface and a lateral inferior surface that meet at a lateral edge, the lateral superior surface angled to connect the lateral side of the body and the lateral edge such that the lateral superior surface does not impinge upon soft tissue near at least one joint of the adjacent joints. The adjacent joints may include a first tarsometatarsal joint and a second tarsometatarsal joint and the at least three guide features may include a first guide feature, a second guide feature, a third guide feature, and a fourth guide feature. Thus, the adjacent joints may include two tarsometatarsal joints that are next to each other in the foot. Alternatively, or in addition, the adjacent joints may include a First tarsometatarsal joint and a Second tarsometatarsal joint in the foot. Also, the adjacent joints may include a joint included in an osteotomy and/or arthrosis procedure (referred to as an "involved joint") and a joint adjacent to the involved joint (referred to as a "non-involved joint").

One general aspect of the present disclosure can include a method for making a patient-specific cutting guide configured for an osteotomy procedure. The method includes accessing a bone model of one or more bones of adjacent joints of a patient; defining one or more guide features of a preliminary cutting guide model for an osteotomy procedure, the preliminary cutting guide model may include a superior surface and an inferior surface; defining at least a portion of the inferior surface of the preliminary cutting guide model according to a topographical surface of at least one bone of the bone model such that the inferior surface substantially matches a contour of the topographical surface; and where the preliminary cutting guide model is configured for fabrication of a patient-specific cutting guide corresponding to the preliminary cutting guide model.

Implementations may include one or more of the following features. The method may include defining one or more guide features of the preliminary cutting guide model which may further include defining a registration key of the inferior surface of the preliminary cutting guide model according to a topographical surface of two or more bones of adjacent joints of the bone model such that the registration key substantially matches a gap between two or more bones of the bone model.

Defining one or more guide features of the preliminary cutting guide model further may include: defining a first slot configured to guide formation of a first cut surface of a first bone of the patient corresponding to a first modeled bone; defining a second slot configured to guide formation of a second cut surface of a second bone of the patient corresponding to a second modeled bone; defining a third slot configured to guide formation of a third cut surface of a third bone of the patient corresponding to a third modeled bone;

defining a fourth slot configured to guide formation of a fourth cut surface of a fourth bone of the patient corresponding to a fourth modeled bone; and where the first slot, second slot, third slot, and fourth slot are positioned such that fixing the first cut surface of the first bone to the second cut surface and the third cut surface of the third bone to the fourth cut surface of the fourth bone mitigates a condition of the patient.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's in scope, the exemplary embodiments of the disclosure will be described with additional specificity and detail through use of the accompanying drawings in which:

FIG. 13 illustrates an exemplary system configured to generate one or more patient-specific instruments configured for an osteotomy, according to one embodiment.

FIGS. 15A-G are top perspective, top, bottom, right, left, front elevation, and rear elevation views, respectively, of a patient-specific cutting guide according to one embodiment.

FIG. 26 is a flow chart diagram of one example method for making a patient-specific cutting guide configured for an osteotomy procedure according to one embodiment.

DETAILED DESCRIPTION

Figure 1:
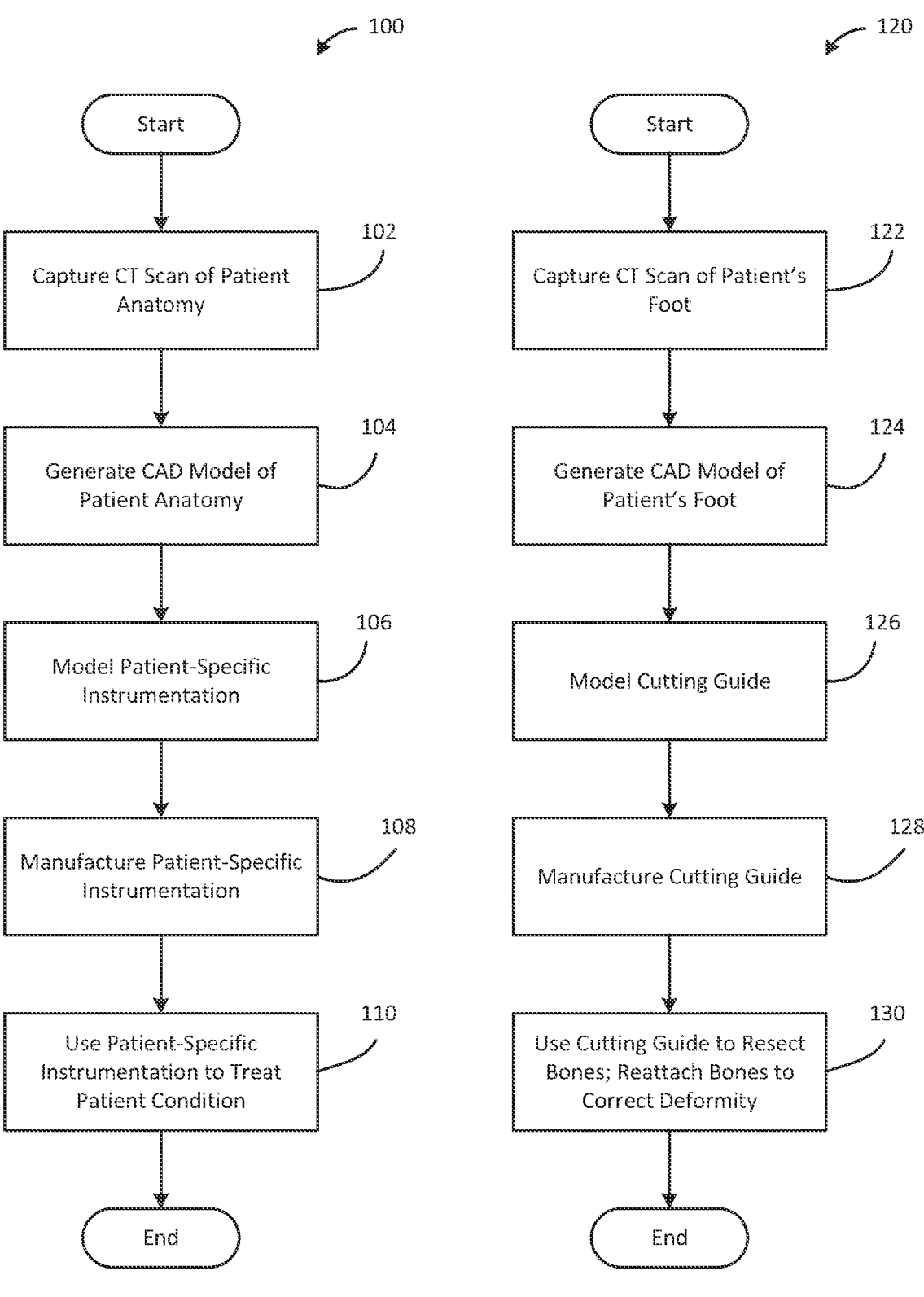
FIG. 1A is a flowchart diagram depicting a method for correcting a bone condition, according to one embodiment.
FIG. 1B is a flowchart diagram depicting a method for correcting a bunion deformity of the human foot, according to one embodiment.

Exemplary embodiments of the disclosure will be best understood by reference to the drawings, wherein like parts are designated by like numerals throughout. It will be readily understood that the components, as generally described and illustrated in the FIGS. herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

"Longitudinal axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

"Topographical" refers to the physical distribution of parts, structures, or features on the surface of, an organ or other anatomical structure, or organism. (Search "define topographical" on google.com. Oxford Languages, Copyright 2022. Oxford University Press. Web., Modified. Accessed 15 Feb. 2022.

The present disclosure discloses surgical instrumentation, devices, systems and/or methods by which an osteotomy can be performed using patient-specific instrumentation, such as for example a patient-specific cutting guide. Osteotomies on certain bones can be very challenging for surgeons to perform manually. In particular, osteotomies on bones in confined spaces or surrounded by other bones can present increased difficulty. For example, osteotomies on small bones such as those of the hands and feet are in small, confined spaces. Such bones may also include a number of other structures, such as soft tissue (e.g., neurovascular bundles and the like) that should be avoided during the osteotomy. Each patient is unique and thus may include various differences in soft tissue structures, hard tissue structures, deformities, or other anomalies that can impact the osteotomy which render known cutting guides impractical or unusable. Advantageously, a patient-specific cutting guide fits a particular patient and can include features having a position and/or orientation as desired by a surgeon to facilitate with the osteotomy.

"Patient-specific instrument" (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient-specific instrument is unique to a single patient and may include features unique to the patient such as a surface contour, component position, component orientation, and/or other features. In other aspects, one patient-specific instrument may be useable with a number of patients having a particular class of characteristics.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may entail capturing a scan of only the particular bone(s) to be treated, or may entail capture of additional anatomic information, such as the surrounding tissues. Additionally or alternatively, the step 102 may entail receiving a previously captured image, for example, at a design and/or fabrication facility. Performance of the step 102 may result in possession of a three-dimensional model of the patient's anatomy, or three-dimensional surface points that can be used to construct such a three-dimensional model.

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiogramand others, represent other technologies that produce data susceptible to representation as a parameter graph vs. time or maps that contain data about the measurement locations. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo.

These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable in the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, bio-chemicals, and the like. Additive manufacturing may provide unique benefits, as an implant together with the pores and/or lattices can be directly manufactured (without the need to generate molds, tool paths, perform any milling, and/or other manufacturing steps).

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a cutting guide that is attachable to one or more bones, with one or more guide features that facilitate resection of the one or more bones pursuant to a procedure such as arthroplasty or arthrodesis. In some embodiments, performance of the step 106 may include modelling an instrument with a bone apposition surface that is shaped to match the contour of a surface of the bone, such that the bone apposition surface can lie directly on the corresponding contour.

As used herein, a "resection" refers to a method, procedure, or step that removes tissue from another anatomical structure or body. A resection is typically performed by a surgeon on a part of a body of a patient. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

As used herein, a "guide" refers to a part, component, or structure designed, adapted, configured, or engineered to guide or direct one or more other parts, components, or structures. A guide may be part of, integrated with, connected to, attachable to, or coupled to, another structure. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, "deployment or insertion guide" that guides or directs the deployment, installation, or insertion of a fastener and/or implant, a "cross fixation guide" that guides deployment of a fastener or fixation member, an "alignment guide" that guides the alignment of two or more objects or structures and the like. Furthermore, guides may include modifiers applied due to the procedure or location within a patient for which the guide is to be used. For example, where a guide is used at a joint, the guide may be referred to herein as an "arthrodesis guide". As used herein, "feature" refers to a distinctive attribute or aspect of something. (Search "feature" on google.com. Oxford Languages, 2021. Web. 20 Apr. 2021.) A feature may include a modifier that identifies a particular function or operation and/or a particular structure relating to the feature. Examples of such modifiers applied to a feature, include, but are not limited to, "attachment feature," "securing feature," "protruding feature," "engagement feature," "disengagement feature," "anchor feature," "guide feature," and the like.

Those of skill in the art will appreciate that a guide feature may take a variety of forms and may include a single feature or one or more features that together form the guide feature. In certain embodiments, the guide feature may take the form of one or more slots. Alternatively, or in addition, a guide feature may be referenced using other names including, but not limited to, channel, cut channels, jig, and the like.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a cutting guide with the bone apposition surface and one or more guide features as described above.

In addition to, or in the alternative to the step 108, the model(s) may be used to select from available sizes of implants and/or instruments and advise the surgeon accordingly. For example, where a range of cutting guides are available for a given procedure, analysis of the CAD data may facilitate pre-operative selection of the optimal cutting guide and/or optimal placement of the cutting guide on the bone. Similarly, if a range of implants may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may be provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may entail placing the modelled bone apposition surface against the corresponding contour of the bone used to obtain its shape, and then using the guide feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions or to generate a patient-specific instrument, such as for example a patient-specific cutting guide. One example of the method 100 will be shown and described in connection with FIG. 1B, for correction of a bunion deformity of the foot. Other examples are included herein.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, advanced computer analysis, machine learning and automated/artificial intelligence may be used to generate a CAD model and/or one or more patient-specific instruments and/or operation plans. For example, a patient-specific cutting guide may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific cutting guide and the patient-specific synthetic cadaver can be provided to a surgeon who can then rehearse an operation procedure in full before going into an operating room with the patient.

In certain embodiments, the patient-specific cutting guide can be used to preposition and pre-drill a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of the cut through the patient-specific cutting guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific cutting guide and/or implant. The details for such lengths, trajectories, and components can be detailed in a report provided to the surgeon preparing to do a procedure.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like. In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft. In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

FIG. 1B is a flowchart diagram depicting a method 120 for correcting bunion deformity of the human foot, according to one embodiment. The method 120 may be used to carry out an arthrodesis procedure by which the first metatarsocuneiform joint is removed and the medial cuneiform and first metatarsal are secured together in a manner that properly aligns the first metatarsal, providing correction of the deformity.

As shown, the method 120 may begin with a step 122 in which a CT scan (or another three-dimensional image) of the patient's foot is obtained. The step 122 may entail capturing a scan of only the medial cuneiform and first metatarsal, or may entail capture of additional anatomic information, i.e., anatomic data, such as the entire foot.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

Additionally or alternatively, the step 122 may entail receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

A bone model or anatomic model of a patient's body or body part(s) may be generated by computing devices that analyze medical imaging images. Structures of a patient's body can be determined using a process called segmentation.

As used herein, "segmentation" or "image segmentation" refers the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while nonparametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct the bunion deformity. Such instrumentation may include a cutting guide that is attachable to the medial cuneiform and the first metatarsal, with two guide features that facilitate resection of the cuneiform and the metatarsal in preparation for arthrodesis. In some embodiments, performance of the step 126 may include modelling the cutting guide with a bone apposition surface that is shaped to match contours of the surfaces of the cuneiform and the metatarsal, such that the bone apposition surface can lie directly on the corresponding contours of the medial cuneiform and the first metatarsal.

In a step 128, the model(s) may be used to manufacture patient-specific instrumentation and/or instruments. This may include manufacturing the cutting guide with the bone apposition surface and the guide features as described above. As in the step 108, the step 128 may additionally or alternatively involve provision of one or more instruments and/or implants from among a plurality of predetermined configurations or sizes. Further, the step 128 may additionally or alternatively involve provision of instructions for placement and/or anchorage of one or more instruments and/or instruments to carry out the procedure.

In a step 130, the manufactured cutting guide may be used in surgery to facilitate treatment of the condition. Specifically, the bone apposition surface of the cutting guide may be placed against the corresponding contours of the medial cuneiform and the first metatarsal. The guide features (for example, slots) may then be positioned on either side of the joint between the medial cuneiform and the first metatarsal to guide resection of the first metatarsal and the medial cuneiform to remove the intervening joint. As used herein, "slot" refers to a narrow opening or groove. (search "slot" on Merriam-Webster.com. Merriam-Webster, 2021. Web. 4 Aug. 2021. Modified.) The cutting guide may then be removed, and the remaining portions of the medial cuneiform and the first metatarsal may be placed to abut each other. The cutting guide may have been shaped such that the cuts made to the medial cuneiform and the first metatarsal are properly oriented to bring the first metatarsal back into its proper orientation relative to the rest of the foot. The medial cuneiform and the first metatarsal may be secured together using a bone plate or the like. The surgical wound may be closed to allow the foot to heal, and to allow the medial cuneiform and the first metatarsal to fuse together.

The method 100 and the method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with FIGS. 2 through 7D. Those of skill in the art will recognize that the method 120 may be used in connection with different instruments; likewise, the instruments of FIGS. 2 through 7D may be used in connection with methods different from the method 100 and the method 120.

Figure 2:
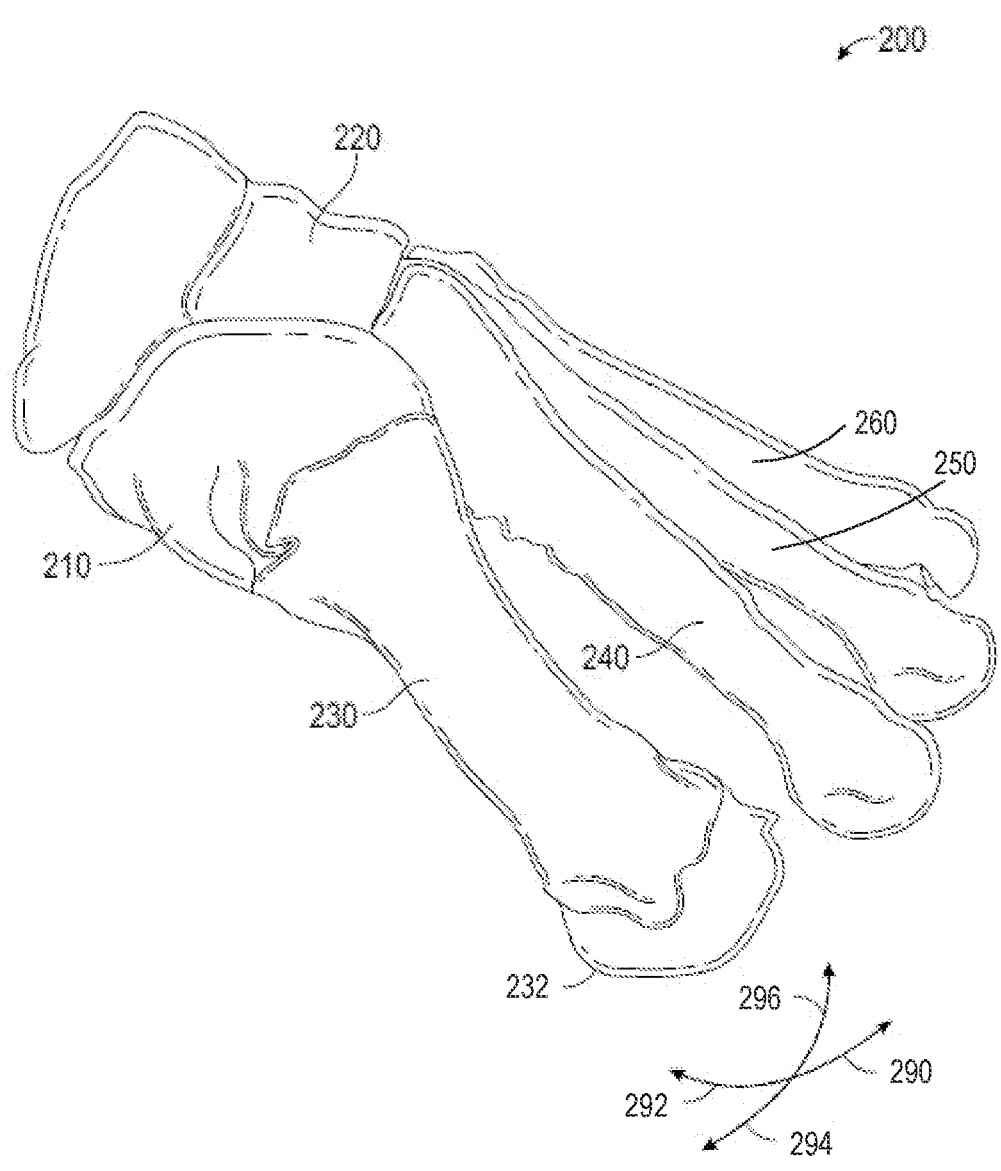
FIG. 2 is a perspective view of a portion of a foot with a bunion deformity to be treated through use of the methods of FIGS. 1A and/or 1B, according to one embodiment.
Figure 3A:
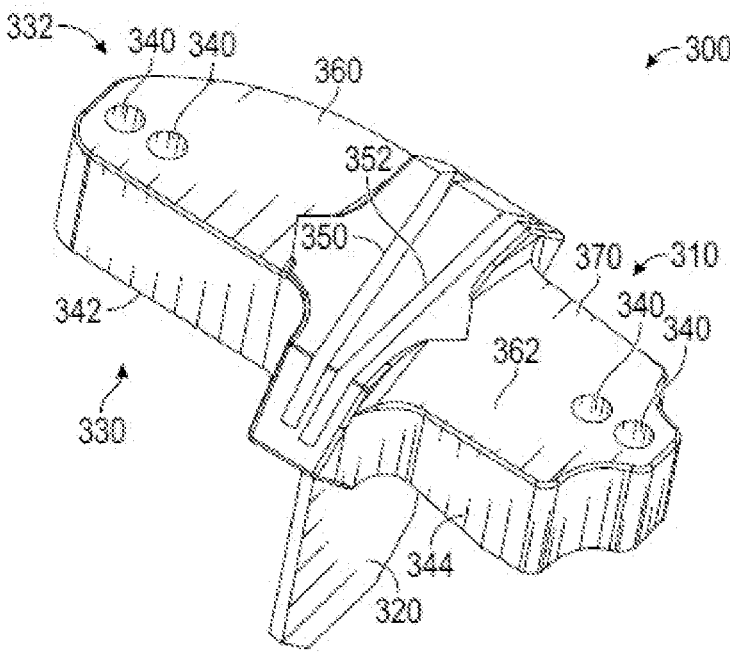
FIGS. 3A, 3B, 3C, and 3D are top perspective, alternative top perspective, front elevation, and bottom perspective views, respectively, of a patient-specific cutting guide, according to one embodiment
Figure 3B:
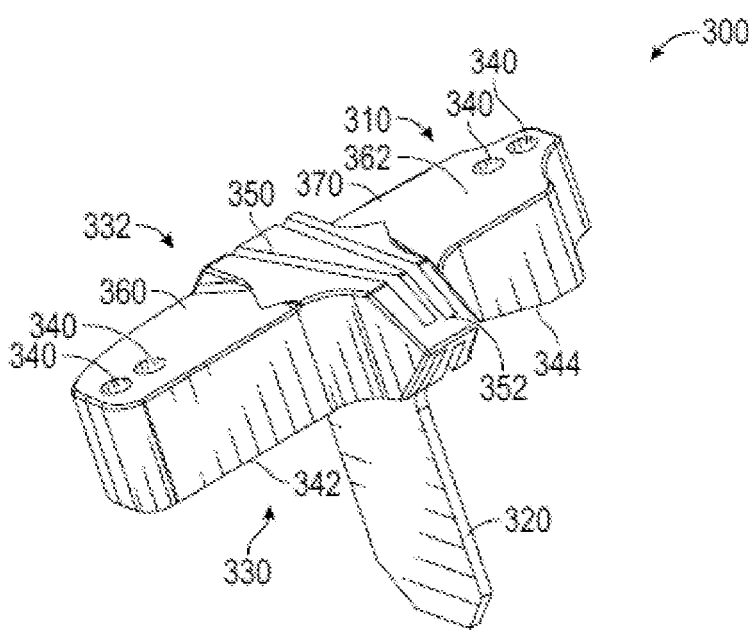
Figure 3C:
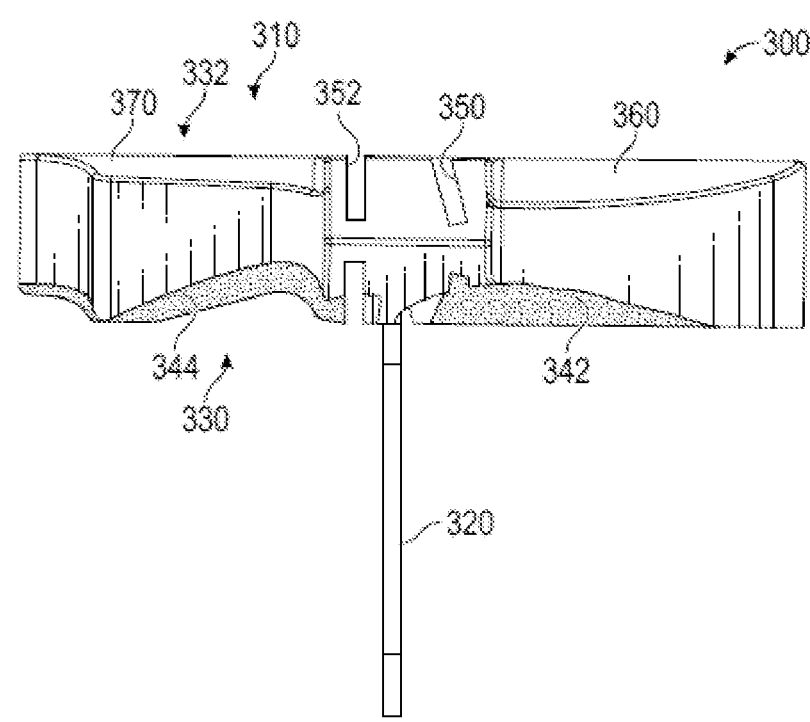
Figure 3D:
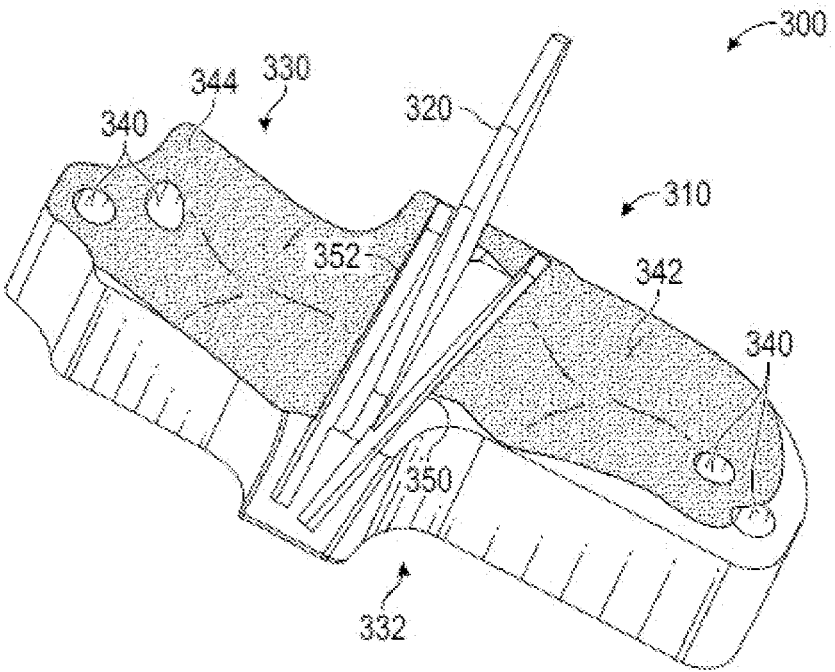

FIG. 2 is a perspective view of a portion of a foot 200 with a bunion deformity to be treated through use of the method 100 (and more specifically, the method 120) described above. The foot 200 may have a medial cuneiform 210, an intermediate cuneiform 220, a first metatarsal 230, a second metatarsal 240, a third metatarsal 250, and a fourth metatarsal 260. The medial cuneiform 210 and the first metatarsal 230 may be joined together at a first metatarsocuneiform joint, and the intermediate cuneiform 220 and the second metatarsal 240 may be joined together at a second metatarsocuneiform joint.

The first metatarsal 230 may be excessively angled in a medial direction 292 (i.e., toward the lower left-hand corner of the page), causing a painful protrusion at a distal end 232 of the first metatarsal 230, and further causing the phalanges (not shown) attached to the distal end 232 to be angled excessively in a lateral direction 290 (i.e., pointing toward the other phalanges of the foot, rather than pointing directly forward). The excessive medial angulation of the first metatarsal 230 may also result in an excessive gap between the first metatarsal 230 and the second metatarsal 240.

The first metatarsal 230 may further be offset in a plantar direction 294 or in a dorsal direction 296, relative to the remainder of the foot 200. Accordingly, the orientation of the first metatarsal 230 may need to be adjusted to move the distal end 232 in the lateral direction 290 and in the plantar direction 294 and/or in the dorsal direction 296.

Every deformity is different; accordingly, the degree of angular adjustment needed in each direction may be different for every patient. Use of a patient-specific cutting guide may help the surgeon obtain the optimal realignment in the lateral direction 290 and in the plantar direction 294 or the dorsal direction 296. Conversely, use of one of several differently-sized cutting guides may provide only approximate correction, as the surgeon may not have a guide that precisely matches the correction needed for the foot 200, and must thus choose the cutting guide that most closely provides the desired correction. Such differently sized cutting guides would not be contoured to fit the medial cuneiform 210 or the first metatarsal 230, thus introducing additional potential for error as the surgeon must properly align the selected cutting guide.

Thus, providing a patient-specific cutting guide may provide unique benefits. Specifically, the patient-specific cutting guide may provide precise correction of the deformity present in the foot 200 and may also reduce the likelihood of improper correction due to misalignment of the cutting guide on the foot 200. The optimal cut provided by such a cutting guide may further reduce the likelihood that additional procedures, such as attachment of the first metatarsal 230 to the second metatarsal 240 to each other with screws or the like, will be needed to provide the desired correction. Any such additional procedure carries its own added surgical burden and risk of failure. Thus, the use of patient-specific instrumentation may shorten surgery, accelerate recovery, and reduce the risk of complications.

FIGS. 3A, 3B, 3C, and 3D are top perspective, alternative top perspective, front elevation, and bottom perspective views, respectively, of a patient-specific cutting guide, or cutting guide 300, according to one embodiment. The cutting guide 300 may be designed to facilitate resection of the medial cuneiform 210 and the first metatarsal 230 with planar cuts at the proper angles to provide dual-plane correction of the orientation of the first metatarsal 230, thereby providing correction in the lateral direction 290 and in the plantar direction 294 or the dorsal direction 296.

As shown, the cutting guide 300 may have a body 310 with a monolithic construction and the general shape of a rectangular prism. As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

The cutting guide 300 may further have a joint alignment feature that helps align the body 310 with the metatarsocuneiform joint between the medial cuneiform 210 and the first metatarsal 230. The joint alignment feature may consist of a joint probe 320 that extends from the body 310 and has a blade-like shape. The body 310 may reside on the dorsal surfaces of the medial cuneiform 210 and the first metatarsal 230, while the joint probe 320 may protrude into the metatarsocuneiform joint between the medial cuneiform 210 and the first metatarsal 230 to provide proper alignment of the body 310 with the metatarsocuneiform joint.

The body 310 may have a bone engagement surface 330 that, upon attachment of the body 310 to the medial cuneiform 210 and the first metatarsal 230, is to face toward the medial cuneiform 210 and the first metatarsal 230. As used herein, "bone engagement surface" refers to a surface or other feature of an object, instrument, or apparatus, such as an implant that is oriented toward, faces, or contacts one or more bones of a patient. In one aspect, the bone engagement surface may abut, touch, or contact a surface of a bone. In another aspect, the bone engagement surface, or parts of the bone engagement surface, may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces. As used herein, matching projections and recesses means that a projection on one structure is of the substantially same size and shape as a corresponding recess of the other structure such that when the two structures are brought into contact or close proximity each projection of one structure seats/sits/fits within the recess of the other structure. A bone engagement surface may include flat parts of a side or surface, contoured parts of a side or surface, projections and/or recesses of a side or surface, or any combination of these. Such variations in the make up and configuration of a bone engagement surface can exist within a single embodiment or separate embodiments.

The body 310 may also have an outward-facing side 332 that, upon attachment of the body 310 to the medial cuneiform 210 and the first metatarsal 230, faces outward, away from the medial cuneiform 210 and the first metatarsal 230. Further, the body 310 may have one or more anchor features that facilitate attachment of the body 310 to the medial cuneiform 210 and/or the first metatarsal 230. Such anchor features may comprise any of a wide variety of holes, spikes, fastening devices, and/or the like. As embodied in FIGS. 3A through 3D, the anchor features may take the form of holes 340 that extend from the bone engagement surface 330 to the outward-facing side 332 and/or one or more fixation devices. The holes 340 may be shaped to accommodate pins, K-wires, and/or other elongated bone fixation elements that can be anchored in the medial cuneiform 210 and/or the first metatarsal 230 to keep the cutting guide 300 in place.

The bone engagement surface 330 may be custom contoured to match the shapes of the medial cuneiform 210 and/or the first metatarsal 230. As embodied in FIGS. 3A through 3D, the bone engagement surface 330 may have a cuneiform apposition portion 342 shaped to lie against the dorsal surface of the medial cuneiform 210, and a metatarsal apposition portion 344 shaped to lie against the dorsal surface of the first metatarsal 230. As shown, the cuneiform apposition portion 342 may be contoured to match the contour of the dorsal surface of the medial cuneiform 210 on which it is to rest, and the metatarsal apposition portion 344 may similarly be contoured to match the contour of the dorsal surface of the first metatarsal 230 on which it is to rest. Thus, the body 310 may have only one stable position and orientation relative to the medial cuneiform 210 and the first metatarsal 230.

Generation of the contours of the cuneiform apposition portion 342 and the metatarsal apposition portion 344 may be performed relative easily in various CAD programs. In some embodiments, the shapes of the corresponding dorsal surfaces of the medial cuneiform 210 and the first metatarsal 230 may be obtained directly from the CAD models and/or CT scan data, and simply copied onto the model for the body 310 of the cutting guide 300. Various operations may be used to copy surfaces from one object to another. Additionally or alternatively, various Boolean operations, such as a Boolean subtraction operation, may be used to remove material from a model for the body 310 with a shape that matches the dorsal surfaces of the medial cuneiform 210 and the first metatarsal 230.

The body 310 may further have guide features that guide a cutter to resect the medial cuneiform 210 and the first metatarsal 230 in the manner needed to make the desired correction. For example, the guide features may be used to guide a planar cutting blade, an arcuate cutting blade, a drill or mill, a burr, and/or the like.

In the embodiment of FIGS. 3A through 3D, the guide features may guide a reciprocating planar blade, such as that of a surgical bone saw, that forms planar cuts in the medial cuneiform 210 and the first metatarsal 230. Thus, the guide features may take the form of a first slot 350 and a second slot 352, which may be positioned toward the center of the body 310, on opposite sides of the joint probe 320. Thus, upon proper positioning of the cutting guide 300, the first slot 350 may be positioned over the medial cuneiform 210 to facilitate resection of the medial cuneiform 210, while the second slot 352 may be positioned over the first metatarsal 230 to facilitate resection of the first metatarsal 230.

In alternative embodiments, a guide feature may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone.

Returning to FIGS. 3A through 3D, the body 310 may further have features that facilitate proper positioning of the cutting guide 300 on the medial cuneiform 210 and the first metatarsal 230. More specifically, the body 310 may have a first bone indicator 360 with the text "CUN," indicating that the end of the body 310 with the first bone indicator 360 is to be positioned over the medial cuneiform 210. Similarly, the body 310 may have a second bone indicator 362 with the text "MET," indicating that the end of the body 310 with the second bone indicator 362 is to be positioned over the first metatarsal 230. In addition, the body 310 may have a side indicator 370 with the text "LEFT," indicating that the cutting guide 300 is to be used in connection with the patient's left foot. The side indicator 370 may be particularly helpful when bunion corrections are to be provided on both of the patient's feet. In such a case, the surgeon may manufacture or receive two separate cutting guides: one for the left foot (the foot 200 of FIG. 2) and another for the right foot (not shown).

Figure 4:
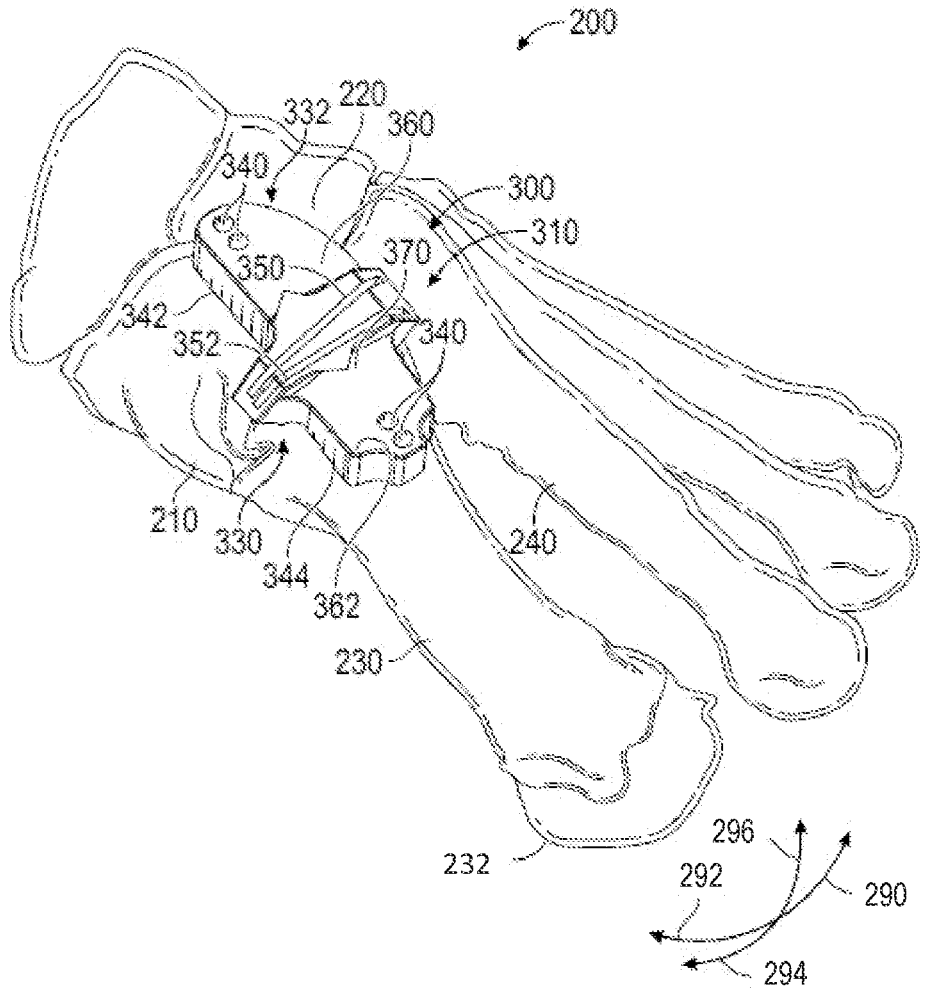
FIG. 4 is a perspective view of the foot of FIG. 2, with the cutting guide of FIGS. 3A, 3B, 3C and 3D positioned on the medial cuneiform and the first metatarsal, but as yet not attached to the medial cuneiform and the first metatarsal.

FIG. 4 is a perspective view of the foot 200 of FIG. 2, with the cutting guide 300 of FIGS. 3A, 3B, 3C and 3D properly positioned on the medial cuneiform 210 and the first metatarsal 230, but as yet not attached to the medial cuneiform 210 and the first metatarsal 230. The surgeon has made the incision(s) to expose the dorsal surfaces of the medial cuneiform 210 and the first metatarsal 230, and has inserted the cutting guide 300 such that the cuneiform apposition portion 342 (identified by the first bone indicator 360 on the outward-facing side 332 of the body 310) is resting on the corresponding dorsal surface of the medial cuneiform 210, and the metatarsal apposition portion 344 (identified by the second bone indicator 362 on the outward-facing side 332 of the body 310) is resting on the corresponding dorsal surface of the first metatarsal 230. Since the cuneiform apposition portion 342 and the metatarsal apposition portion 344 are contoured to match the bone surfaces on which they rest, the body 310 may readily slide into its proper position on the medial cuneiform 210 and the first metatarsal 230.

Notably, the joint probe 320 (not visible) may reside between the medial cuneiform 210 and the first metatarsal 230 (i.e., distal to the medial cuneiform 210 and proximal to the first metatarsal 230). The surgeon may need to cut the metatarsocuneiform joint between the medial cuneiform 210 and the first metatarsal 230 to form a space between the medial cuneiform 210 and the first metatarsal 230 to receive the joint probe 320. Positioning the joint probe 320 in this space may further help to ensure that the cutting guide 300 is properly aligned relative to the medial cuneiform 210 and the first metatarsal 230.

Figure 5:
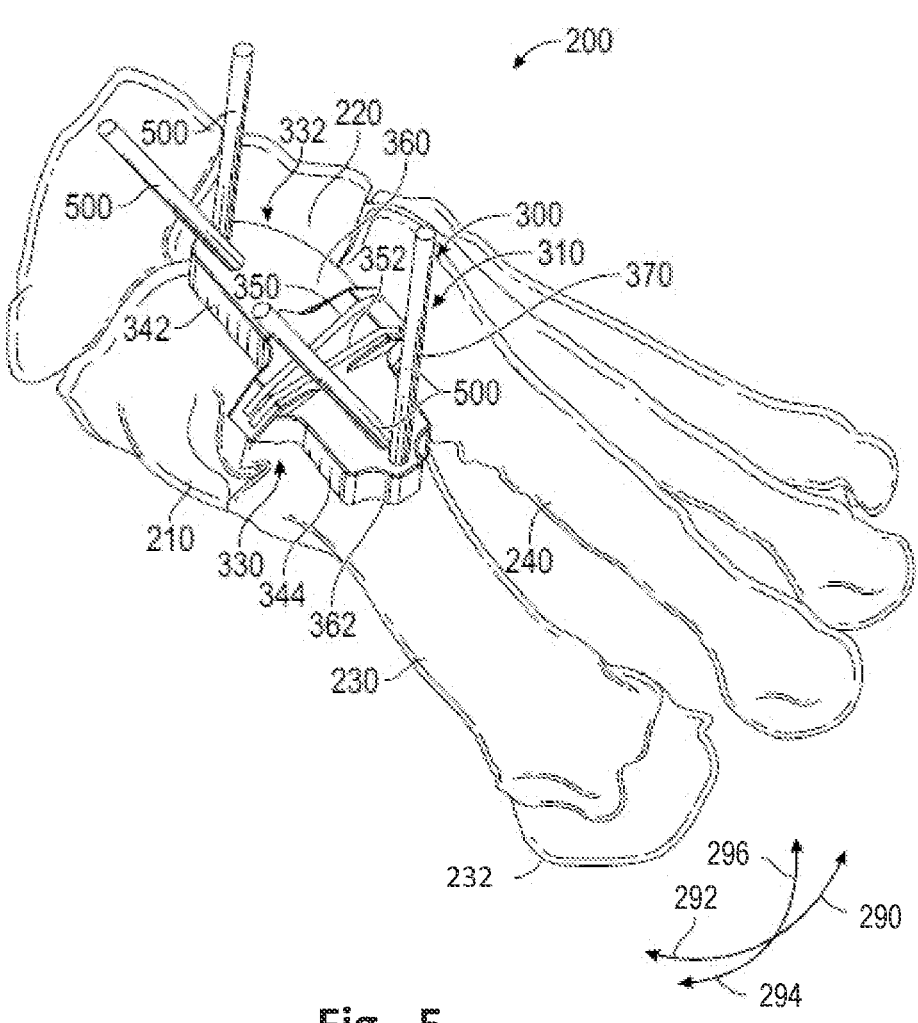
FIG. 5 is a perspective view of the foot of FIG. 2, with the cutting guide of FIGS. 3A, 3B, 3C, and 3D properly positioned on the medial cuneiform and the first metatarsal and attached to the medial cuneiform and the first metatarsal in preparation for resection of the medial cuneiform and the first metatarsal, according to one embodiment.

FIG. 5 is a perspective view of the foot 200 of FIG. 2, with the cutting guide 300 of FIGS. 3A, 3B, 3C, and 3D properly positioned on the medial cuneiform 210 and the first metatarsal 230 and attached to the medial cuneiform 210 and the first metatarsal 230 in preparation for resection of the medial cuneiform 210 and the first metatarsal 230. Specifically, pins 500 may be inserted through the holes 340 in the body 310 and anchored in the medial cuneiform 210 and the first metatarsal 230. Each of the pins 500 may have a sharp and/or threaded distal end that can penetrate and/or readily be retained in the bone of the medial cuneiform 210 or the first metatarsal 230. Additionally or alternatively, a drill or other hole-forming instrument may be used to pre-form holes in the medial cuneiform 210 and/or the first metatarsal 230 to receive the distal ends of the pins 500.

As shown, the body 310 may have two holes 340 positioned over the medial cuneiform 210, and two holes 340 positioned over the first metatarsal 230. This is merely exemplary; in some embodiments, a cutting guide may be secured to one of the medial cuneiform 210 and the first metatarsal 230 or may be secured to either of the medial cuneiform 210 and the first metatarsal 230 with one pin 500, or with more than two pins 500. Further, in some alternative embodiments, different fasteners may be used, such as screws, clamps, clips, and/or the like.

Once the cutting guide 300 has been secured relative to the medial cuneiform 210 and the first metatarsal 230, the medial cuneiform 210 and the first metatarsal 230 may be resected. In some embodiments, a reciprocating blade may be inserted into the first slot 350 and moved medially and laterally, between opposite ends of the first slot 350, to make a planar cut that removes the distal end of the medial cuneiform 210. Similarly, the reciprocating blade (or a different reciprocating blade) may be inserted into the second slot 352 and moved medially and laterally, between opposite ends of the second slot 352, to make a planar cut that removes the proximal end of the first metatarsal 230. The cuts in the medial cuneiform 210 and the first metatarsal 230 may be made in either order. In either case, once both cuts are made, the metatarsocuneiform joint between the medial cuneiform 210 and the first metatarsal 230 may be removed, resulting in exposure of "bleeding" bone at the distal end of the medial cuneiform 210 and the proximal end of the first metatarsal 230. The cutting guide 300 may be removed, along with some or all of the pins 500. If desired, at least two of the pins 500 may remain in place and used to attach a distractor (not shown) to the medial cuneiform 210 and the first metatarsal 230, such that the distractor can temporarily widen the space between the medial cuneiform 210 and the first metatarsal 230 to allow for fenestration and/or other preparation of the cut surfaces of the medial cuneiform 210 and the first metatarsal 230. Once such preparation has been carried out, the remaining pins 500 may also be removed.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface (s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

The resulting bleeding and/or prepared bone may readily grow together and fuse, upon abutment of the distal end of the medial cuneiform 210 to the proximal end of the first metatarsal 230, particularly with application of some compression across the juncture of the two bones. Since the positions and orientations of the first slot 350 and the second slot 352 were carefully selected to provide the proper correction, the first metatarsal 230 may be positioned to abut the medial cuneiform 210, resulting in reorientation of the first metatarsal 230 to a desired orientation, relative to the lateral direction 290 and the plantar direction 294 and/or the dorsal direction 296. Further, the surgeon may optionally rotate the first metatarsal 230, relative to the medial cuneiform 210, about an axis perpendicular to the cutting planes, if desired.

Figures 6A, 6B, 6C:
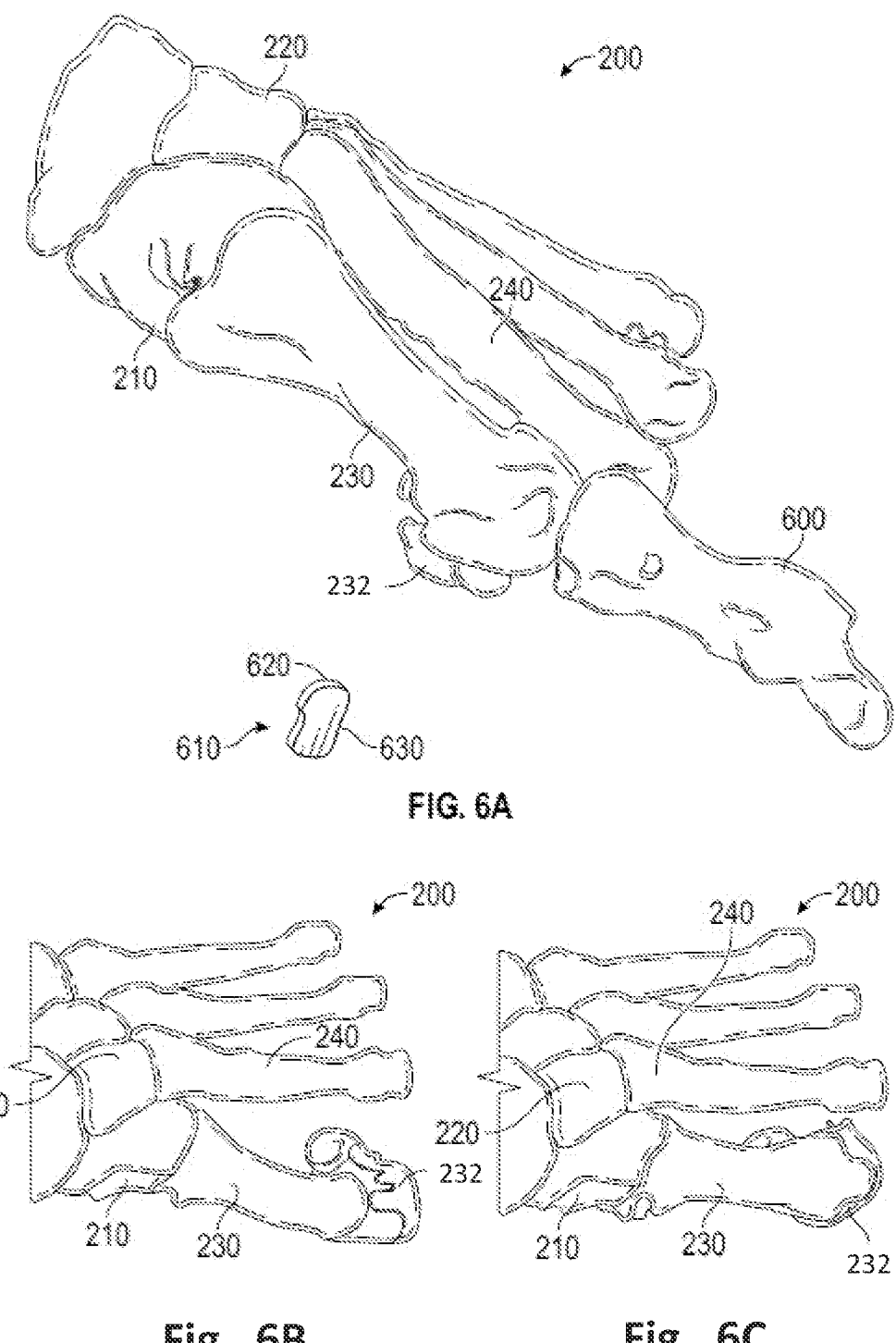
FIG. 6A is a perspective view of the foot of FIG. 2, after resection of the medial cuneiform and the first metatarsal, removal of the cutting guide, and placement of the first metatarsal to abut the medial cuneiform, according to one embodiment.
FIGS. 6B and 6C are dorsal views of the foot of FIG. 2, before and after correction, respectively, according to one embodiment.
Figures 7A, 7B:
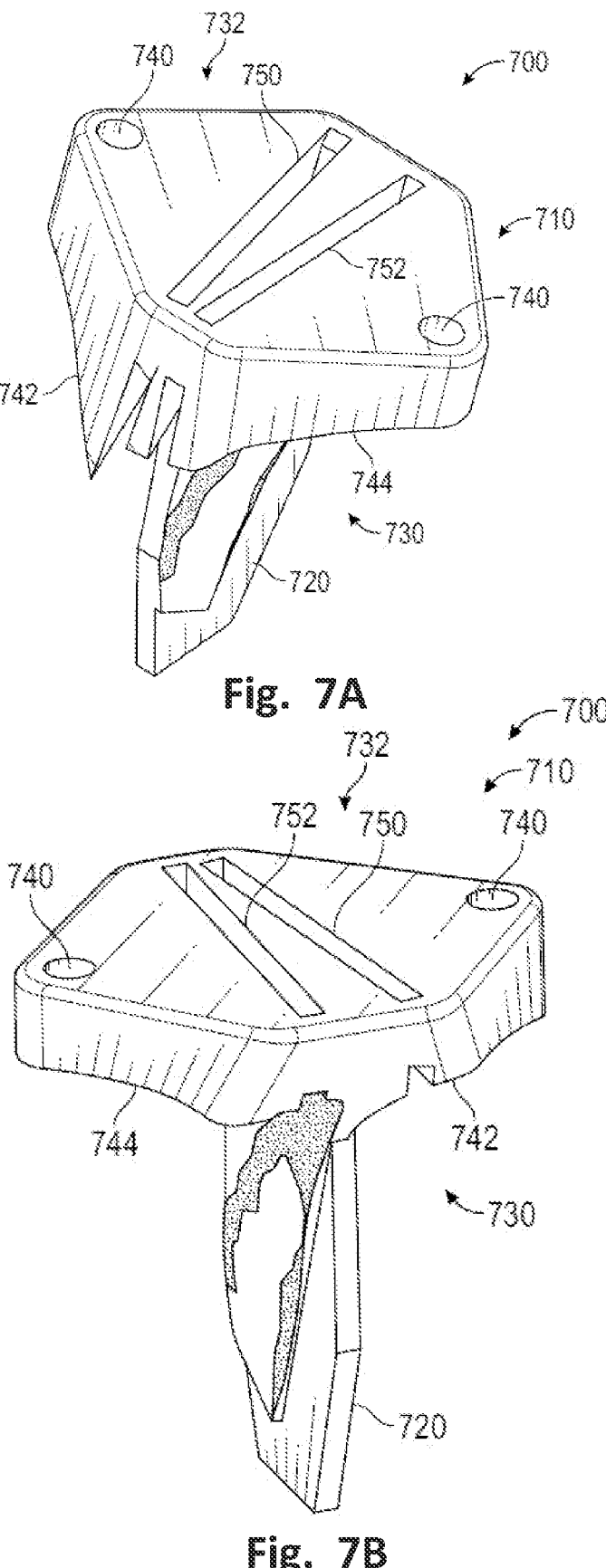
FIGS. 7A, 7B, 7C, and 7D are top perspective, alternative top perspective, front elevation, and bottom perspective views, respectively, of a patient-specific cutting guide according to one alternative embodiment.
Figure 7C:
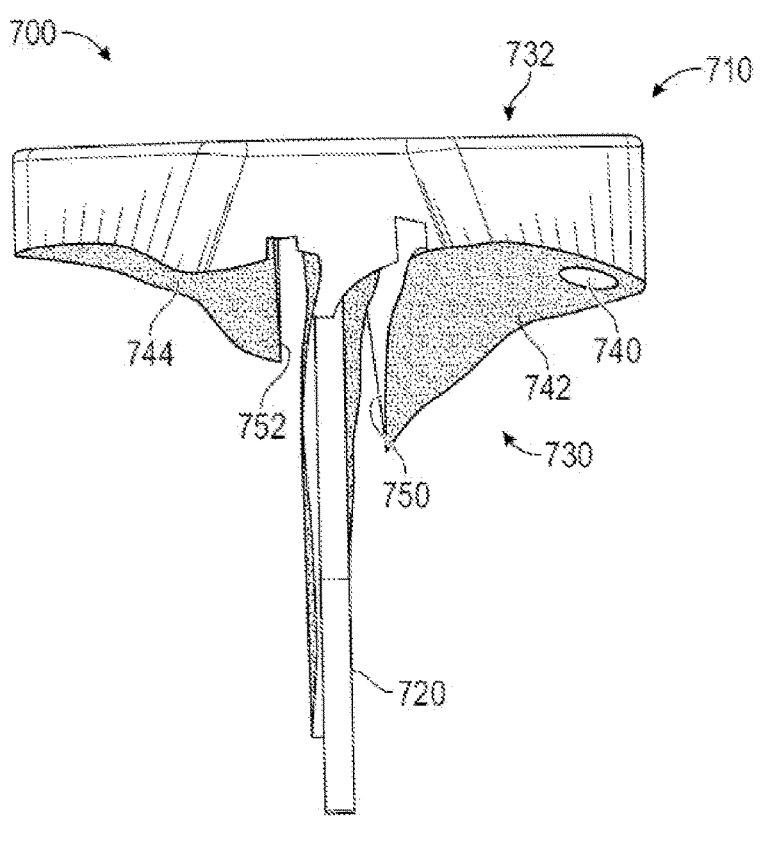
Figure 7D:
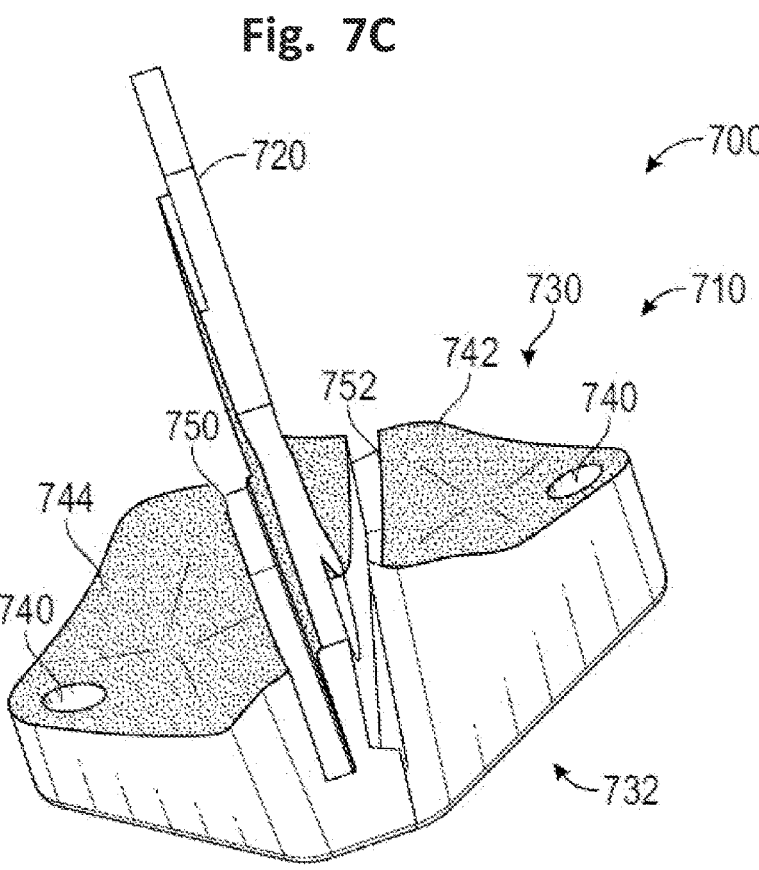

FIG. 6A is a perspective view of the foot 200 of FIG. 2, after resection of the medial cuneiform 210 and the first metatarsal 230, removal of the cutting guide 300, and placement of the first metatarsal 230 to abut the medial cuneiform 210. As shown, the distal end 232 of the first metatarsal 230 may now be positioned much closer to the second metatarsal 240, in a more natural position. Further, FIG. 6A depicts a first proximal phalanx 600, which may now be properly oriented generally parallel to the other phalanges (not shown), rather than pointing in the lateral direction 290. If desired, further steps may be performed relative to the joint between the first metatarsal 230 and the first proximal phalanx 600 in order to keep them in the proper relative orientation. The distal end 232 may also have been shifted in the plantar direction 294 or in the dorsal direction 296 from the position of FIG. 2. Thus, the desired dual-plane correction of the orientation of the first metatarsal 230 may be complete.

The first metatarsal 230 may be secured to the medial cuneiform 210, at least until proper bone in-growth has occurred between the medial cuneiform 210 and the first metatarsal 230. In some embodiments, a bone plate (not shown) or other fastener (not shown) may be used to secure the medial cuneiform 210 and the first metatarsal 230 together. Additional hardware (not shown) may be used to stabilize the position and/or orientation of the first proximal phalanx 600 relative to the first metatarsal 230, if desired. The surgical wound may be closed, and the foot 200 may be allowed to heal with the bunion deformity corrected.

FIGS. 6B and 6C are dorsal views of the foot 200, before and after correction, respectively. FIGS. 6B and 6C illustrate the correction of the angulation of the first metatarsal 230, by which the distal end 232 of the first metatarsal 230 is moved in the lateral direction 290. In some embodiments, an implant 610 may be inserted in the space between the first metatarsal 230 and the medial cuneiform 210 in order hold the first metatarsal 230 and the medial cuneiform 210 together and/or facilitate bony fusion between the first metatarsal 230 and the medial cuneiform 210.

In some embodiments, the implant 610 may be patient-specific. For example, the implant 610 may have a cuneiform-facing side 620 that is shaped and/or sized to be secured to the adjoining, resected surface of the medial cuneiform 210, and a metatarsal-facing side 630 that is shaped and/or sized to be secured to the adjoining, resected surface of the first metatarsal 230. As the resections made to the first metatarsal 230 and the medial cuneiform 210 may both planar, the cuneiform-facing side 620 and/or the metatarsal-facing side 630 may also be planar. However, the cuneiform-facing side 620 and/or the metatarsal-facing side 630 may advantageously each be shaped to match the profile of the resected surface of the medial cuneiform 210 and the first metatarsal 230, respectively.

This shaping may be accomplished by custom-designing the implant 610 for the patient, using the same models (for example, from CT scans) of the first metatarsal 230 and the medial cuneiform 210 that were used to generate the cutting guide 300. Thus, the implant 610 may have a shape that provides secure attachment and/or fusion between the first metatarsal 230 and the medial cuneiform 210 while avoiding proud edges or other protruding features that could otherwise interfere with surrounding tissues.

As indicated previously, the cutting guide 300 is one of many patient-specific instruments that may be used in connection with the method 100 and/or the method 120. An alternative cutting guide suitable for use with the method 120 will be shown and described in connection with FIGS. 7A, 7B, 7C, and 7D.

FIGS. 7A, 7B, 7C, and 7D are top perspective, alternative top perspective, front elevation, and bottom perspective views, respectively, of a patient-specific cutting guide, or cutting guide 700, according to one alternative embodiment. The cutting guide 700 may be used to correct a bunion deformity, such as that of the foot 200 of FIG. 2. Thus, the cutting guide 700 may also be designed to facilitate resection of the medial cuneiform 210 and the first metatarsal 230 with planar cuts at the proper angles to provide dual-plane correction of the orientation of the first metatarsal 230, thereby providing correction in the lateral direction 290 and in the plantar direction 294 or the dorsal direction 296.

As shown, the cutting guide 700 may have a body 710 with a monolithic construction and the general shape of a rectangular prism. The cutting guide 700 may further have a joint alignment feature that helps align the body 710 with the metatarsocuneiform joint between the medial cuneiform 210 and the first metatarsal 230. The joint alignment feature may consist of a joint probe 720 that extends from the body 710 and has a blade-like shape. The body 710 may reside on the dorsal surfaces of the medial cuneiform 210 and the first metatarsal 230, while the joint probe 720 may protrude into the metatarsocuneiform joint between the medial cuneiform 210 and the first metatarsal 230 to provide proper alignment of the body 710 with the metatarsocuneiform joint. Notably, the joint probe 720 may have surfaces that are not simply planar, but rather have some contouring by which the shape of the joint probe 720 is matched to the adjoining surfaces of the medial cuneiform 210 and/or the first metatarsal 230. Such contouring of the joint probe 720 may enable more precise alignment of the body 710 with the metatarsocuneiform joint.

The body 710 may have a bone engagement surface 730 that, upon attachment of the body 710 to the medial cuneiform 210 and the first metatarsal 230, is to face toward the medial cuneiform 210 and the first metatarsal 230. The body 710 may also have an outward-facing side 732 that, upon attachment of the body 710 to the medial cuneiform 210 and the first metatarsal 230, faces outward, away from the medial cuneiform 210 and the first metatarsal 230. Further, the body 710 may have one or more anchor features that facilitate attachment of the body 710 to the medial cuneiform 210 and/or the first metatarsal 230. Such anchor features may comprise any of a wide variety of holes, spikes, fastening devices, and/or the like. As embodied in FIGS. 7A through 7D, the anchor features may take the form of holes 740 that extend from the bone engagement surface 330 to the outward-facing side 332 and/or one or more fixation devices. The holes 340 may be shaped to accommodate pins, K-wires, and/or other elongated bone fixation elements that can be anchored in the medial cuneiform 210 and/or the first metatarsal 230 to keep the cutting guide 700 in place. As embodied in FIGS. 7A through 7D, only one hole 340 may be present on each side of the body 710. Thus, the body 710 may be secured to the medial cuneiform 210 with only a single pin or K-wire (not shown) and to the first metatarsal 230 with only another single pin or K-wire (not shown).

The bone engagement surface 730 may be custom contoured to match the shapes of the medial cuneiform 210 and/or the first metatarsal 230. As embodied in FIGS. 7A through 7D, the bone engagement surface 730 may have a cuneiform apposition portion 742 shaped to lie against the dorsal surface of the medial cuneiform 210, and a metatarsal apposition portion 744 shaped to lie against the dorsal surface of the first metatarsal 230. As shown, the cuneiform apposition portion 742 may be contoured to match the contour of the dorsal surface of the medial cuneiform 210 on which it is to rest, and the metatarsal apposition portion 744 may similarly be contoured to match the contour of the dorsal surface of the first metatarsal 230 on which it is to rest. Thus, the body 710 may have only one stable position and orientation relative to the medial cuneiform 210 and the first metatarsal 230. Alternatively, or in addition, the cuneiform apposition portion 742 may be contoured to match the contour of a surface that is between the dorsal surface and a medial or lateral surface and/or the surface includes at least a portion of the dorsal surface of the medial cuneiform 210 on which it is to rest, and the metatarsal apposition portion 744 may similarly be contoured to match the contour of a surface that is between the dorsal surface and a medial or lateral surface and/or the surface includes at least a portion of the dorsal surface of the dorsal surface of the first metatarsal 230.

In certain embodiments, the cuneiform apposition portion 742 and/or metatarsal apposition portion 744 may be referred to as a bone engagement surface. "Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search "joint" on Wikipedia.com Dec. 19, 2021. CC-BY-SA 3.0 Modified. Accessed Jan. 20, 2022.)

In certain embodiments, certain portions of the topography of the articular surfaces of a joint may not factor into the form and/or shape of the cuneiform apposition portion 742 and/or the metatarsal apposition portion 744 because those parts of the bones will be resected during the procedure. Alternatively, or in addition, the topography of the articular surfaces of a joint may be factored into the form and/or shape of the cuneiform apposition portion 742 and/or the metatarsal apposition portion 744 even though those parts of the bones will be resected during the procedure.

Like the cuneiform apposition portion 342 and the metatarsal apposition portion 344 of the cutting guide 300, generation of the contours of the cuneiform apposition portion 742 and the metatarsal apposition portion 744 may be performed relative easily in various CAD programs through surface copy operations, Boolean operations, and/or the like.

The body 710 may further have guide features that guide a cutter to resect the medial cuneiform 210 and the first metatarsal 230 in the manner needed to make the desired correction. For example, the guide features may be used to guide a planar cutting blade, an arcuate cutting blade, a drill or mill, and/or the like.

In the embodiment of FIGS. 7A through 7D, the guide features may guide a reciprocating planar blade, such as that of a surgical bone saw, that forms planar cuts in the medial cuneiform 210 and the first metatarsal 230. Thus, the guide features may take the form of a first slot 750 and a second slot 752, which may be positioned toward the center of the body 710, on opposite sides of the joint probe 720. Thus, upon proper positioning of the cutting guide 700, the first slot 750 may be positioned over the medial cuneiform 210 to facilitate resection of the medial cuneiform 210, while the second slot 752 may be positioned over the first metatarsal 230 to facilitate resection of the first metatarsal 230.

In operation, the cutting guide 700 may be used in a manner similar to that of the cutting guide 300. However, the cutting guide 700 may only be secured to each of the medial cuneiform 210 and the first metatarsal 230 with a single pin or K-wire (not shown), as mentioned previously. Further, the cutting guide 700 is smaller than the cutting guide 300. Thus, the cutting guide 700 may be placed through a smaller, less invasive incision. One advantage to patient-specific instrumentation may be that instruments may be made smaller, since they are not limited to certain sizes. Many known instruments come in discrete sizes, each of which is designed to accommodate a range of patient anatomic dimensions. Thus, for given patient anatomy, the instrument must be large enough to treat the anatomy at either end of its range. This typically requires the instrument to be oversized for many anatomic dimensions it is designed to treat. Notably, the cutting guide 700 is merely one compact example; other cutting guides may be made even smaller; in some embodiments, cutting guides may be made that have a smaller width between holes (e.g., holes 740 on the cutting guide 700). As long as the holes are sufficiently far apart to avoid interference of the pins 500 with the operation of the cutting blade, the cutting guide may function appropriately. Thus, Lapidus and other procedures may be accomplished through a very narrow incision through the use of patient-specific instrumentation.

Those of skill in the art will recognize that a wide variety of differently configured cutting guides may be used in conjunction with the method 120 set forth above. Further, a wide variety of patient-specific instruments may be used in connection with the method 100, including but not limited to cutting guides, gages, implant positioning guides, joint distractors, joint compressors, soft tissue retractors, and the like. "Patient-specific cutting guide" refers to a cutting guide designed, engineered, and/or fabricated for use with a specific patient. In one aspect, a patient-specific cutting guide is unique to a single patient and may include features unique to the patient such as a surface contour or other features.

Furthermore, patient-specific cutting guides may be used for various other procedures on the foot, or on other bones of the musculoskeletal system. Patient-specific cutting guides may be used for various procedures involving osteotomy, including but not limited to arthroplasty, fusion, and deformity correction procedures. According to one example, patient-specific cutting guides similar to the cutting guide 300 and the cutting guide 700 may be used for the metatarsophalangeal ("MTP") joint. A method similar to the method 100 may be employed.

In some embodiments, one or more articulating surfaces of a joint may be replaced and/or resurfaced. For example, for the MTP joint, a patient-specific cutting guide may be used to determine the angles of cuts on the distal metatarsal or the proximal phalanx in preparation for replacement or resurfacing of the metatarsal head and/or the proximal phalangeal base. Implants for either the metatarsal or the phalanx may be customized to match the patient's original anatomy, such as the curvature of the MTP joint. In other embodiments, an MTP joint may be fused through the use of patient-specific cutting guides. Patient-specific cutting guides may be used to treat (for example, via fusion, resurfacing, and/or arthroplasty) any joint in the body, using methods similar to the method 100.

According to other examples, patient-specific cutting guides may be used to carry out an Evans calcaneal osteotomy and/or a medializing calcaneal osteotomy. Patient-specific instruments will be shown and described in connection with FIGS. 8A through 11, in relation to an Evans calcaneal osteotomy, and a medializing calcaneal osteotomy.

As used herein, "osteotomy procedure" or "surgical osteotomy" refers to a surgical operation in which one or more bones are cut to shorten and/or lengthen them and/or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics.

Figures 8A, 8B, 8C:
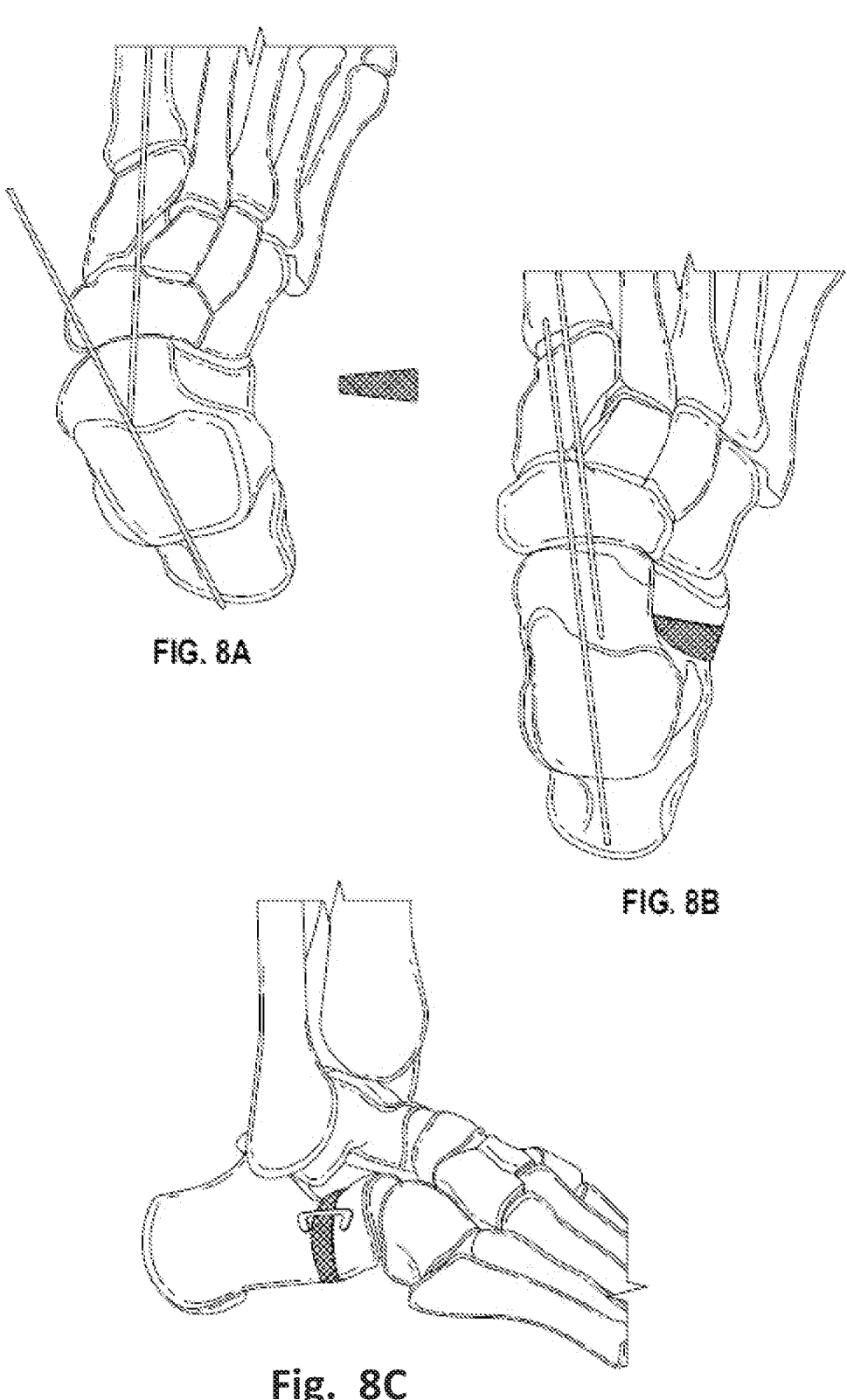
FIGS. 8A, 8B, and 8C are dorsal pre-operative, dorsal post-operative, and lateral post-operative views, respectively, of a foot treated with an Evans calcaneal osteotomy, according to one embodiment.

FIGS. 8A, 8B, and 8C are dorsal pre-operative, dorsal post-operative, and lateral post-operative views, respectively, of a foot treated with an Evans calcaneal osteotomy, according to one embodiment. Outward rotation of the foot may occur in patients with flatfoot. An Evans or lateral column lengthening procedure is sometimes performed for these patients. An incision is made on the outside of the foot, and the front half of the heel bone is cut. A bone wedge (typically either titanium or a bone-based graft) is then placed into the cut area of the heel bone. This wedge helps to "lengthen" the heel bone and rotate the foot back into its correct position. The wedge is usually kept in place using screws or a surgical staple.

Figure 9A:
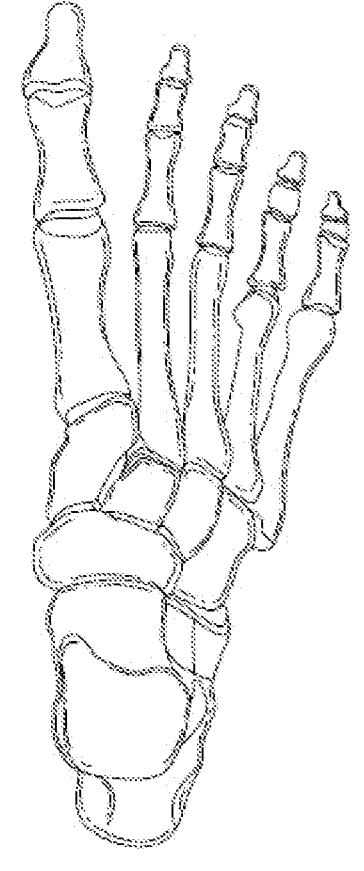
FIGS. 9A and 9B are dorsal post-operative and lateral post-operative views, respectively, of a foot treated with a medializing calcaneal osteotomy, according to one embodiment.
Figure 9B:
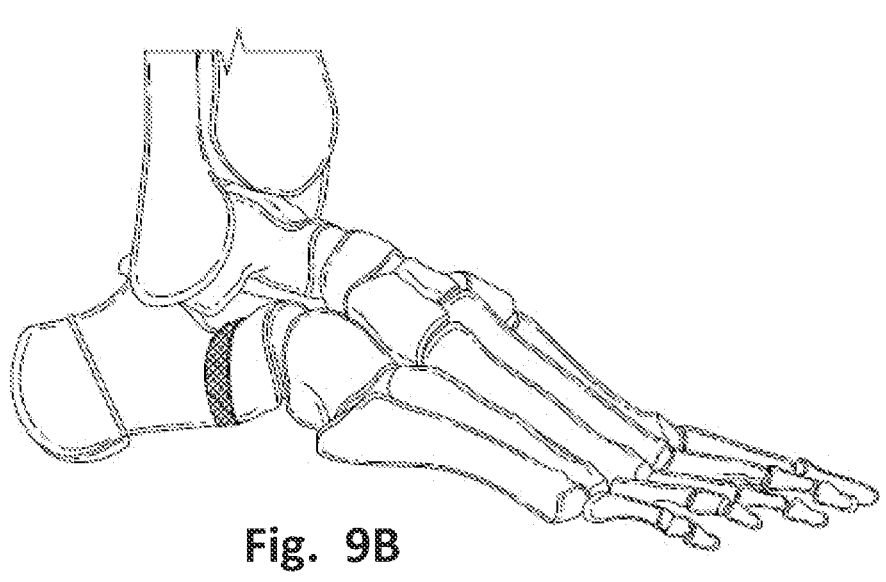

FIGS. 9A and 9B are dorsal post-operative and lateral post-operative views, respectively, of a foot treated with a medializing calcaneal osteotomy, according to one embodiment. A medializing calcaneal osteotomy (heel slide) procedure is often used when the calcaneus (heel bone) has shifted out from underneath the leg. An incision is made on the outside of the heel, and the back half of the heel bone is cut and slid back underneath the leg. The heel is then fixed in place using metal screws or a plate. This also helps to reposition the Achilles tendon towards the center of the ankle/rearfoot. The medializing calcaneal osteotomy can be used in place of, or in addition to, an Evans calcaneal osteotomy.

Figure 10:
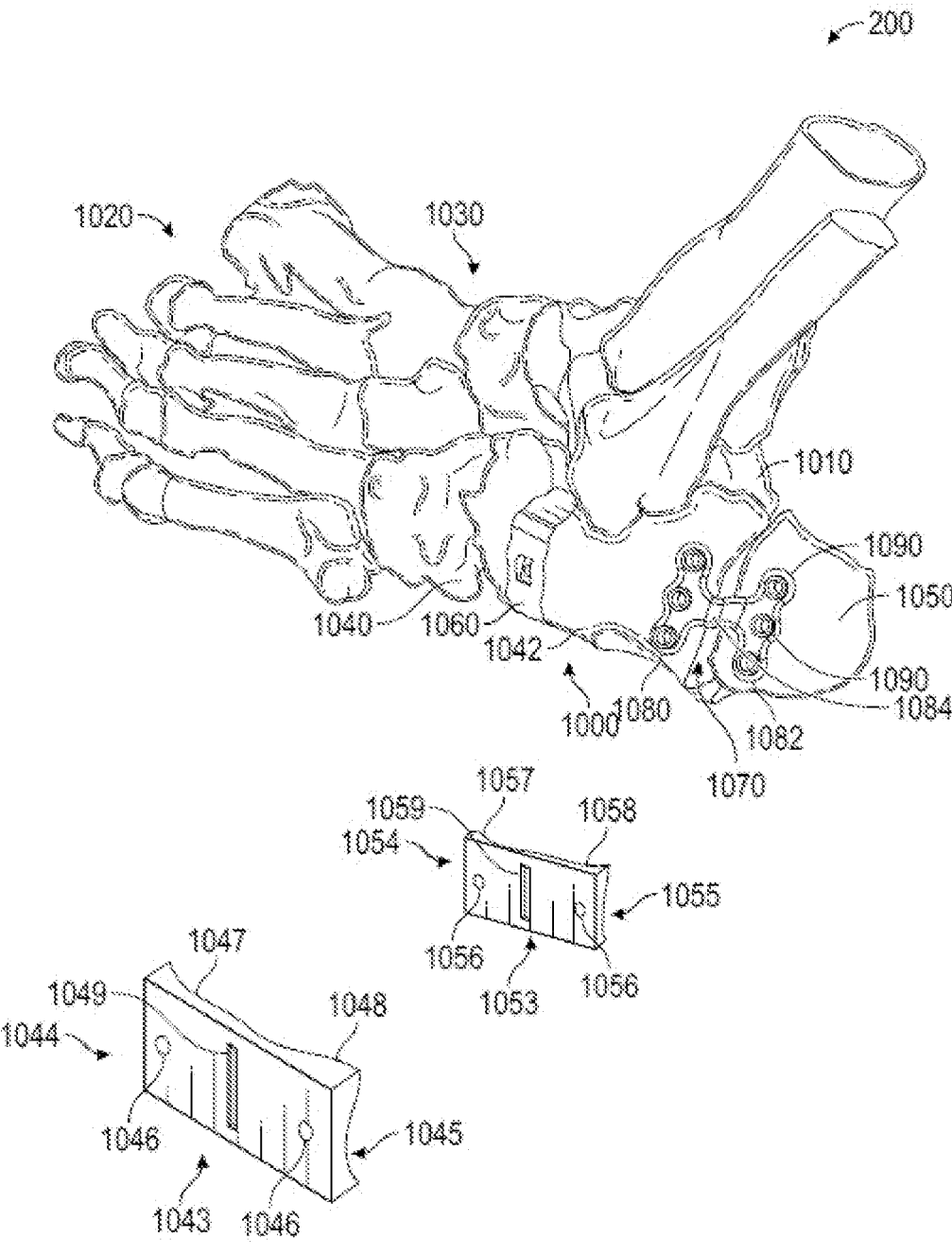
FIG. 10 is a rear, perspective view of the foot of FIG. 2, after performance of an Evans calcaneal osteotomy and a medializing calcaneal osteotomy with patient-specific instruments and/or implants, according to one embodiment.

FIG. 10 is a rear, perspective view of the foot 200 of FIG. 2, after performance of an Evans calcaneal osteotomy and a medializing calcaneal osteotomy with patient-specific instruments and/or implants, according to one embodiment. The foot 200 may have a calcaneus 1000 and a talus 1010, in addition to the metacarpals 1020 and cuneiforms 1030 depicted in FIG. 2. Pursuant to the Evans calcaneal osteotomy, an anterior portion of the calcaneus 1000 may be cut along the medial-lateral direction to separate a first bone segment 1040 of the calcaneus 1000 from a second bone segment 1042 of the calcaneus 1000. The second bone segment 1042 may be reoriented medially, relative to the first bone segment 1040, such that a heel 1050 of the calcaneus 1000 is moved medially, simulating a natural, healthy arch in the foot 200.

The cut between the first bone segment 1040 and the second bone segment 1042 may be carried out virtually (for example, in CAD) on a model of the calcaneus 1000 obtained from a CT scan or other imaging of the patient's foot. Thus, the optimal realignment of the posterior end of the calcaneus 1000 can be obtained. If desired, a patient-specific cutting guide, or cutting guide 1043, may be generated in order to facilitate resection of the calcaneus 1000.

As shown, the cutting guide 1043 may have a first end 1044 and a second end 1045, each of which has an anchor feature 1046. The anchor features 1046 may be used to secure the first end 1044 and the second end 1045 to the first bone segment 1040 and the second bone segment 1042, respectively. The first end 1044 may have a first bone engagement surface 1047 that is shaped to match a corresponding contour on the first bone segment 1040, and the second end 1045 may have a second bone engagement surface 1048 that is shaped to match a corresponding contour on the second bone segment 1042. Thus, the cutting guide 1043 may naturally lie flush with the surface of the calcaneus 1000, in the optimal position on the calcaneus 1000 to facilitate resection of the calcaneus 1000 to divide the first bone segment 1040 from the second bone segment 1042. The cutting guide 1043 may have a guide feature 1049, such as a slot, that can be used to guide a cutter to form a single cut between the first bone segment 1040 and the second bone segment 1042.

After the cut has been made to split the calcaneus 1000 into the first bone segment 1040 and the second bone segment 1042, the surgeon may angle the second bone segment 1042 relative to the first bone segment 1040 in the predetermined (previously modeled) relative orientation. This reorientation between the first bone segment 1040 and the second bone segment 1042 may leave a wedge-shaped gap between the first bone segment 1040 and the second bone segment 1042. In order to maintain the desired relative orientation, an implant 1060 with a wedge shape may be inserted into the gap and secured to the first bone segment 1040 and the second bone segment 1042. The implant 1060 may be fabricated specifically for the patient, since the precise angulation and position of the realignment may also be patient-specific. As shown, the implant 1060 may have exterior surfaces that are contoured to match the contours of the adjoining portions of the first bone segment 1040 and the second bone segment 1042. Thus, the implant 1060 may provide secure fixation, while not protrude beyond the adjoining surfaces of the first bone segment 1040 and the second bone segment 1042. Thus, the implant 1060 may be devoid of proud edges or other protrusions that could otherwise interfere with motion between the calcaneus 1000 and the talus 1010, or with surrounding soft tissues, thus interfering with the patient's post-operative gait. "Soft tissue" refers to tissue of a patient (i.e., human or animal). Examples of soft tissue include but are not limited to skin, ligament, tendon, fascia, fat muscle, fibrous tissue, blood vessels, lymph vessels, brain tissue, and/or nerves.

The implant 1060 may be made of any biocompatible material, including but not limited to Titanium and alloys thereof, stainless steel, PEEK, and/or the like. The implant 1060 may be formed by any method known in the art, including but not limited to forging, casting, milling, additive manufacturing, and/or the like. In some embodiments, the implant 1060 may have an interior void that can be filled with bone graft or other material designed to promote boney in-growth between the cut surfaces of the first bone segment 1040 and the second bone segment 1042. In alternative embodiments, the implant 1060 may have a mesh and/or lattice structure that facilitates such boney in-growth, which structure may be formed via additive manufacturing.

As mentioned previously, a medializing calcaneal osteotomy may optionally be performed in addition to, or in place of, the Evans calcaneal osteotomy. As shown, the heel 1050 may be cut from the remainder of the second bone segment 1042 and may be displaced medially. This displacement may also help to restore normal gait and tendon function in the foot 200, particularly when coupled with the Evans calcaneal osteotomy. The proper displacement of the heel 1050 relative to the remainder of the second bone segment 1042 may be determined based on analysis of the CAD models from scans of the foot 200. If desired, the model of the calcaneus 1000 may be divided and manipulated in CAD to simulate the repositioning of the heel 1050 pursuant to the medializing calcaneal osteotomy. Thus, the alignment of the heel 1050 relative to the remainder of the foot 200 can easily be assessed and optimized prior to surgery.

Such preoperative alignment and planning may be particularly useful where multiple procedures, such as the Evans calcaneal osteotomy and the medializing calcaneal osteotomy, are combined for a single patient. Without such planning, it may be difficult to properly assess the effect of the combined procedures on the patient's anatomy. For example, the effect of the Evans calcaneal osteotomy, and that of the medializing calcaneal osteotomy, is to shift the heel 1050 medially. The combined shift may be difficult to assess in the operating room but may be much more easily and accurately gauged via manipulation of the modeled anatomy.

In some embodiments, one or more additional procedures may be carried out, in addition to or in the alternative to those of FIG. 9. For example, in addition to or in the alternative to the Evans calcaneal osteotomy and the medializing calcaneal osteotomy, a cotton osteotomy (medial cuneiform opening wedge osteotomy) and/or a first meta-tarsal midfoot osteotomy may be performed. Patient-specific cutting guides may be designed, fabricated, and surgically used to facilitate any of these procedures through the presence of bone engagement surfaces that are shaped to rest on the particular bony surfaces adjacent to the osteotomy.

As in the case of the Evans calcaneal osteotomy, a custom cutting guide, or cutting guide 1053, may be generated to help the surgeon obtain the correction that was previously modeled and/or planned using the computer models of the foot 200. The cutting guide 1053 may have a structure and function similar to that of the cutting guide 1043 used for the Evans calcaneal osteotomy. Such a cutting guide may have contoured surfaces that match the contours of the adjoining boney surfaces of the remainder of the second bone segment 1042 and/or the heel 1050.

More specifically, the cutting guide 1053 may have a first end 1054 and a second end 1055, each of which has an anchor feature 1056. The anchor features 1056 may be used to secure the first end 1054 and the second end 1055 to the second bone segment 1042 and the heel 1050, respectively. The first end 1054 may have a first bone engagement surface 1057 that is shaped to match a corresponding contour on the second bone segment 1042, and the second end 1055 may have a second bone engagement surface 1058 that is shaped to match a corresponding contour on the heel 1050. Thus, the cutting guide 1053 may naturally lie flush with the surface of the calcaneus 1000, in the optimal position on the calcaneus 1000 to facilitate resection of the calcaneus 1000 to divide the second bone segment 1042 from the heel 1050. The cutting guide 1053 may have a guide feature 1059, such as a slot, that can be used to guide a cutter to form a single cut between the second bone segment 1042 and the heel 1050.

In order to maintain the heel 1050 in the proper position relative to the remainder of the second bone segment 1042, a bone plate 1070 may be secured to the heel 1050 and to the remainder of the second bone segment 1042. The bone plate 1070 may include a first end 1080 secured to the remainder of the second bone segment 1042, a second end 1082 secured to the heel 1050, and an intermediate portion 1084 that extends from the first end 1080 to the second end 1082, and provides the desired medial shift between the first end 1080 and the second end 1082. The first end 1080 and the second end 1082 may be secured to the remainder of the second bone segment 1042 and to the heel 1050, respectively, through the use of screws 1090.

Like the implant 1060, the bone plate 1070 may be made of any known biocompatible material, through the use of any manufacturing process known in the art. In some embodiments, the bone plate 1070 may also be fabricated specifically for the foot 200, enabling the bone plate 1070 to precisely maintain the desired level of correction. When made specifically for the foot 200 in combination with each other, the implant 1060 and the bone plate 1070 may provide a highly predictable, precise, and customizable level of correction of the flat foot deformity.

Figure 11:
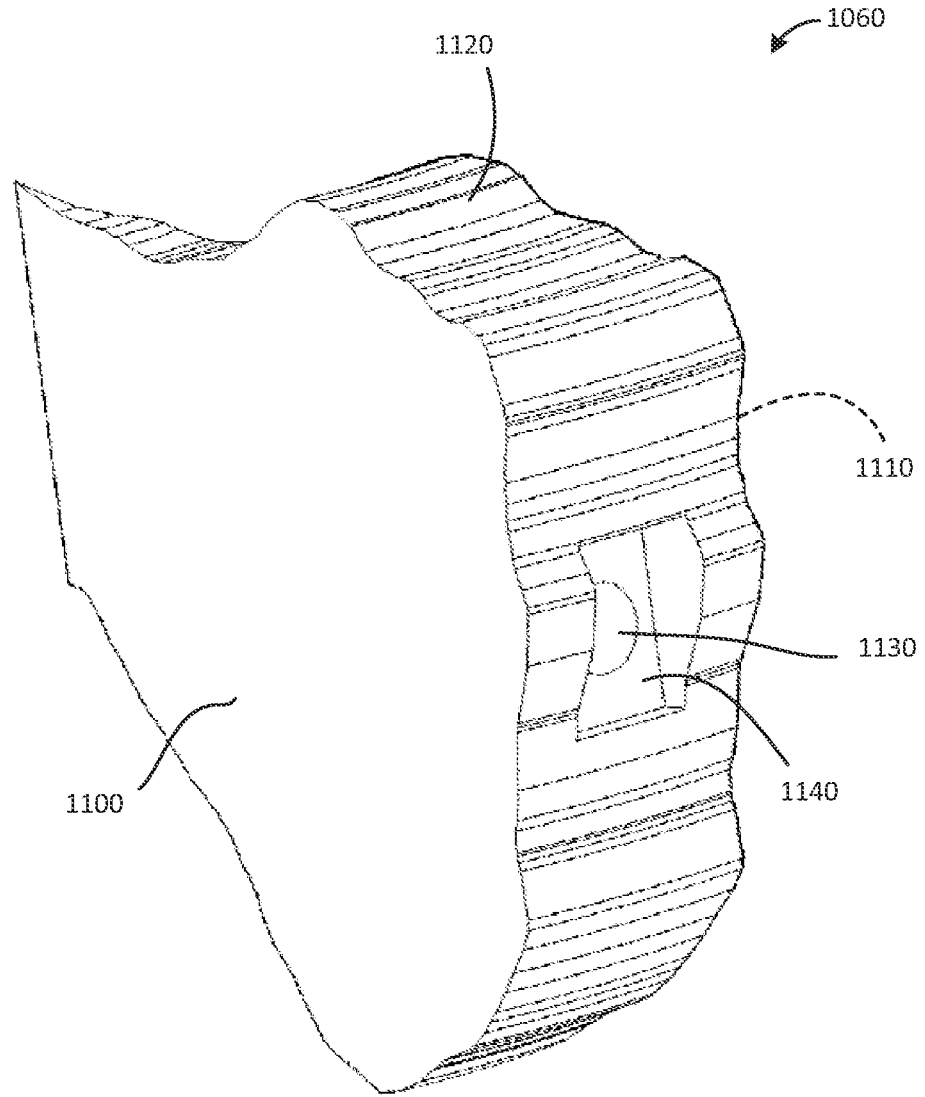
FIG. 11 is a perspective view of the implant of FIG. 10, in isolation, according to one embodiment.

FIG. 11 is a perspective view of the implant 1060, in isolation. As shown, the implant 1060 may have a first bone-facing surface 1100 that is generally flat and shaped to match the cut surface of the first bone segment 1040. The first bone-facing surface 1100 is shown in FIG. 11 with a smooth shape; however, in alternative embodiments, the first bone-facing surface 1100 may be roughened and/or may have teeth, spikes, ridges, and/or other features intended to penetrate the first bone segment 1040 in order to provide for more secure engagement of the implant 1060 with the first bone segment 1040. Similarly, the implant 1060 may have a second bone-facing surface 1110 (not visible) that is also generally flat and shaped to match the cut surface of the second bone segment 1042. Like the first bone-facing surface 1100, the second bone-facing surface 1110 may be roughened or have protruding features that strengthen engagement of the implant 1060 with the second bone segment 1042. If desired, the implant 1060 may be further held in place through the use of bone screws, cement, one or more bone plates, and/or other features known in the art to secure an implant to bone.

The edges of the first bone-facing surface 1100 and the second bone-facing surface 1110 may be shaped to line up with the edges of the cut surfaces of the first bone segment 1040 and the second bone segment 1042, respectively. The implant 1060 may also have a contoured surface 1120 that extends between the edges of the first bone-facing surface 1100 and the second bone-facing surface 1110. The contoured surface 1120 may also be contoured to match the contours of the adjoining portions of the first bone segment 1040 and the second bone segment 1042. Thus, the contoured surface 1120 may provide a continuous surface, devoid of protrusions, that extends between the adjoining surfaces of the first bone segment 1040 and the second bone segment 1042.

A threaded hole 1130 may optionally be provided in the contoured surface 1120. The threaded hole 1130 may be used to secure the implant 1060 to an insertion instrument, a positioning instrument, and/or a removal instrument. The threaded hole 1130 may be formed in a recess 1140 in the contoured surface 1120 so that the threaded hole 1130 can have the desired orientation, without affecting the shape of the contoured surface 1120 more than necessary. Of course, many other features may be used to secure an instrument to the implant 1060, including various clips, clamps, fasteners, and interfacing features, as known in the art.

As used herein, "registration" refers to a method, process, module, component, apparatus, and/or system that seeks to achieve precision in the alignment of two objects. One object may serve as a source object and the other object may serve as the destination object. The source object and destination object may each be physical objects and/or one object or the other may be a model of an object, the model maintained, represented, and managed within a computer. The goal of the registration operation is to coordinate, align, or arrange the source object and the destination object in to a substantially matching relationship relative to each other.

In one example, a source object may be a physical device, implant, or instrument designed and configured to contact a surface of the destination object. Accordingly, the two connecting surfaces may be configured to each have a substantially matching contour (one the inverse of the other). In this example, the destination object may be a natural object such as a bone of a patient. The contour of the destination object may be obtained by using medical imaging and models derived from the medical imaging.

In the process of registering the source object to the destination object two surfaces of the objects may be brought into contact and one object, or the other, or both, may be moved relative to each other until each protrusion from one objects fits within a corresponding recess, depression, void, or groove of the other object and/or the other object's surface and vice versa. When such alignment and/or coordination of the source object and destination object is accomplished the source object is considered "registered" with destination object. In this example, the source object may be an instrument and destination object is a bone and the instrument is registered with the bone surface when the instrument is placed against the bone such that the contour of the surface of the instrument touching the surface of the bone have a matching/coordinate relationship (e.g., each protrusion on one surface extends into a corresponding recess, depression, or void of the other surface).

The present disclosure is not limited to cutting guides or extremity procedures. In some embodiments, patient-specific instrumentation may be used to correct a wide variety of bone conditions. Such conditions include, but are not limited to, any angular deformities from within one bone segment in either the lower or upper extremities (for example, tibial deformities, calcaneal deformities, femoral deformities, and radial deformities). The present disclosure may also be used to treat an interface between two bone segments (for example, the ankle joint, metatarsal cuneiform joint, lisfranc's joint, complex charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cubiod or subtalar joint or at the ankle between the tibia and talar junction. Additionally, patient-specific instruments could be used in the proximal leg between two bone segments or in the upper extremity such as found at the wrist or metacarpal levels.

Figure 12:
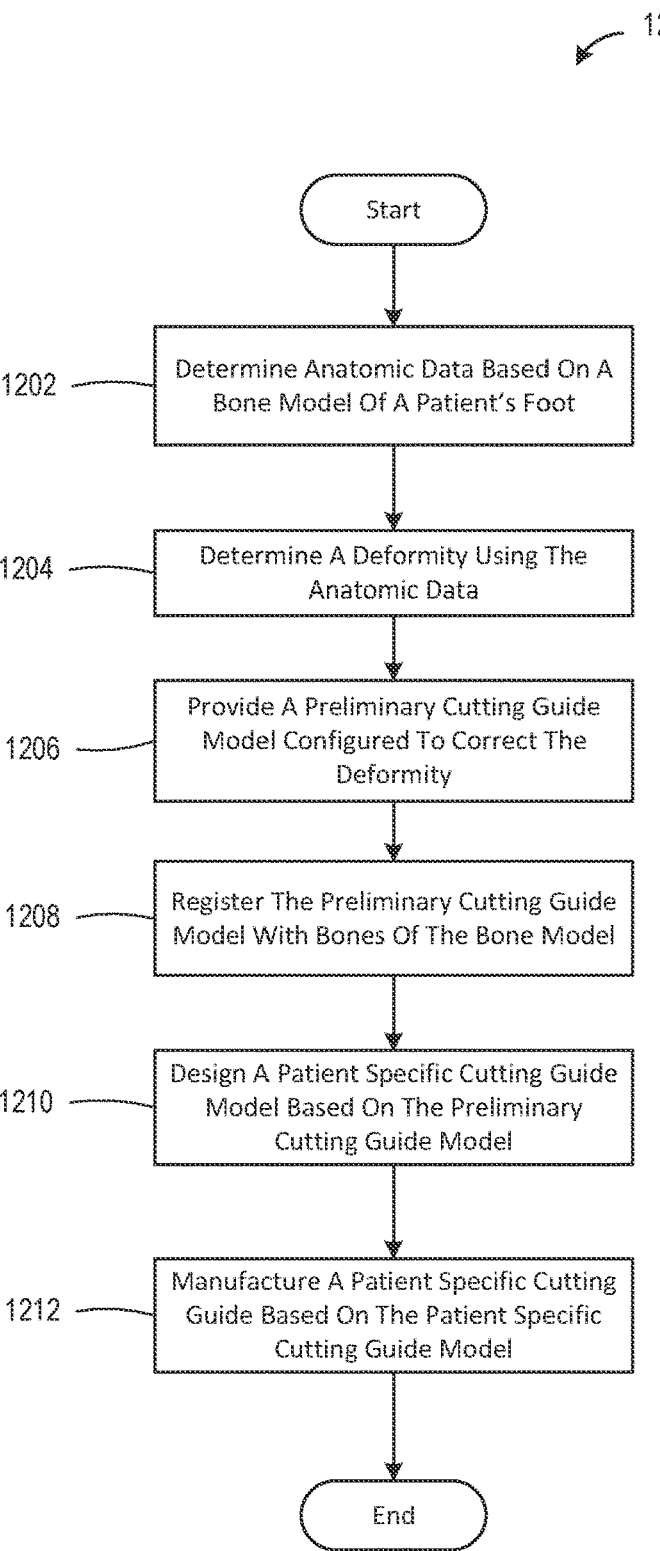
FIG. 12 is a flowchart diagram depicting a method for generating one or more patient-specific instruments configured to correct a bone condition, according to one embodiment.

FIG. 12 illustrates a flowchart diagram depicting a method 1200 for generating one or more patient-specific instruments configured to correct a bone condition, according to one embodiment. Prior to steps of the method 1200, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve or be a part of anatomic data for a patient.

In one embodiment, the method 1200 begins after a bone model of a patient's body or body part(s) is generated. In a first step 1202, the method 1200 may review the bone model and data associated with the bone model to determine anatomic data of a patient's foot.

After step 1202, the method 1200 determine 1204 a deformity in the patient's anatomy using the anatomic data. In certain embodiments, the detection and/or identification of a deformity may employ advanced computer analysis, expert systems, machine learning, and/or automated/artificial intelligence. As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.) Various kinds of deformities may be identified, such as a bunion. The deformities determined may include congenital as well as those caused by injury or trauma.

Next, the method 1200 proceeds and a preliminary cutting guide model is provided 1206 from a repository of template cutting guide models. A preliminary cutting guide model is a model of a preliminary cutting guide.

As used herein, "preliminary cutting guide" refers to a guide configured, designed, and/or engineered to serve as a template, prototype, archetype, or starting point for creating, generating, or fabricating a patient-specific cutting guide. In one aspect, the preliminary cutting guide may be used, as-is, without any further changes, modifications, or adjustments and thus become a patient-specific cutting guide. In another aspect, the preliminary cutting guide may be modified, adjusted, or configured to more specifically address the goals, objectives, or needs of a patient or a surgeon and by way of the modifications become a patient-specific cutting guide. The patient-specific cutting guide can be used by a user, such as a surgeon, to guide making one or more resections of a structure, such as a bone for a procedure. Accordingly, a preliminary cutting guide model can be used to generate a patient-specific cutting guide model. The patient-specific cutting guide model may be used in a surgical procedure to address, correct, or mitigate effects of the identified deformity and may be used to generate a patient-specific cutting guide that can be used in a surgical procedure for the patient.

In certain embodiments, the preliminary cutting guide model may be generated based on anatomic data and/or a bone model or a combination of these, and no model or predesigned structure, template, or prototype. Alternatively, or in addition, the preliminary cutting guide model may be, or may originate from, a template cutting guide model selected from a set of template cutting guide model. Each model in the set of template cutting guide models may include one or more cutting guide features positioned and/or sized and/or configured to fit for an average patient's foot. The template cutting guide model may subsequently be modified or revised by an automated process or manual process to generate the preliminary cutting guide model used in this disclosure.

As used herein, "template cutting guide" refers to a guide configured, designed, and/or engineered to serve as a template for creating, generating, or fabricating a patient-specific cutting guide. In one aspect, the template cutting guide may be used, as-is, without any further changes, modifications, or adjustments and thus become a patient-specific cutting guide. In another aspect, the template cutting guide may be modified, adjusted, or configured to more specifically address the goals, objectives, or needs of a patient or a surgeon and by way of the modifications become a patient-specific cutting guide. The patient-specific cutting guide can be used by a user, such as a surgeon, to guide making one or more resections of a structure, such as a bone for a procedure. Accordingly, a template cutting guide model can be used to generate a patient-specific cutting guide model. The patient-specific cutting guide model may be used in a surgical procedure to address, correct, or mitigate effects of the identified deformity or condition and may be used to generate a patient-specific cutting guide that can be used in a surgical procedure for the patient.

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

Next, the method 1200 may register 1208 the preliminary cutting guide model with one or more bones of the bone model. This step 1208 facilitates customization and modification of the preliminary cutting guide model to generate a patient-specific cutting guide model from which a patient-specific cutting guide can be generated. The registration step 1208 combines two models and/or patient imaging data and positions both models for use in one system and/or in one model.

As used herein, "image registration" refers to a method, process, module, component, apparatus, and/or system that seeks to achieve precision in the alignment of two images. As used here, "image" may refer to one or more of an image of a structure or object, a time series of images such as a video or other time series, another image, or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. Image registration can be done using an intrinsic method or an extrinsic method or a combination of both. The extrinsic image registration method uses an outside object that is introduced into the physical space where the image was taken. The outside object may be referred to using different names herein such as a "reference," "visual reference," "visualization reference," "reference point," "reference marker," "patient reference," or "fiducial marker." The intrinsic image registration method uses information from the image of the patient, such as landmarks and object surfaces.

There may be several considerations made when performing image registration: The transformation model. Common choices are rigid, affine, and deformable (i.e., nonlinear) transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures. Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

Next, the method 1200 may design 1210 a patient-specific cutting guide model based on the preliminary cutting guide model. The design step 1210 may be completely automated or may optionally permit a user to make changes to a preliminary cutting guide model or partially completed patient-specific cutting guide model before the patient-specific cutting guide model is complete. A preliminary cutting guide model and patient-specific cutting guide model are two examples of an instrument model. As used herein, "instrument model" refers to a model, either physical or digital, that represents an instrument, tool, apparatus, or device. Examples, of an instrument model can include a cutting guide model, a patient-specific cutting guide model, and the like. In one embodiment, a patient-specific cutting guide and a patient-specific cutting guide model may be unique to a particular patient and that patient's anatomy and/or condition.

The method 1200 may conclude by a step 1212 in which patient-specific cutting guide may be manufactured based on the patient-specific cutting guide model. Various manufacturing tools, devices, systems, and/or techniques can be used to manufacture the patient-specific cutting guide. As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

FIG. 13 illustrates an exemplary system 1300 configured to generate one or more patient-specific instruments configured for an osteotomy or an osteotomy to correct a bone condition, according to one embodiment. "Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position. The system 1300 may include an apparatus 1302 configured to accept, review, receive or reference a bone model 1304 and provide a patient-specific cutting guide 1306. In one embodiment, the apparatus 1302 is a computing device. In another embodiment, the apparatus 1302 may be a combination of computing devices and/or software components or a single software component such as a software application.

The apparatus 1302 may include a determination module 1310, a deformity module 1320, a provision module 1330, a registration module 1340, a design module 1350, and a manufacturing module 1360. Each of which may be implemented in one or more of software, hardware, or a combination of hardware and software.

The determination module 1310 determines anatomic data 1312 from a bone model 1304. In certain embodiments, the system 1300 may not include a determination module 1310 if the anatomic data is available directly from the bone model 1304. In certain embodiments, the anatomic data for a bone model 1304 may include data that identifies each anatomic structure within the bone model 1304 and attributes about the anatomic structure. For example, the anatomic data may include measurements of the length, width, height, and density of each bone in the bone model. Furthermore, the anatomic data may include position information that identifies where each structure, such as a bone is in the bone model 1304 relative to other structures, including bones. The anatomic data may be in any suitable format and may be stored separately or together with data that defines the bone model 1304.

In one embodiment, the determination module 1310 may use advanced computer analysis such as image segmentation to determine the anatomic data. Alternatively, or in addition the determination module 1310 may use software and/or systems that implement one or more artificial intelligence methods (e.g., machine learning and/or neural networks) for deriving, determining, or extrapolating, anatomic data from the bone model. In one embodiment, the determination module 1310 may perform an anatomic mapping of the bone model 1304 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

The deformity module 1320 determines or identifies one or more deformities or other anomalies based on the anatomic data 1312. The deformity may include a deformity between two bones of a patient's foot as represented in the bone model 1304. In one embodiment, the deformity module 1320 may compare the anatomic data 1312 to a general model that is representative of most patient's anatomies and that does not have a deformity or anomaly. In one embodiment, if the anatomic data 1312 does not match the general model a deformity is determined. Various deformities may be detected including those that have well-known names for the condition and those that are unnamed.

The provision module 1330 is configured to provide a preliminary cutting guide model. The provision module 1330 may use a variety of methods to provide the preliminary cutting guide model. In one embodiment, the provision module 1330 may generate preliminary cutting guide model. In the same or an alternative embodiment, the provision module 1330 may select a template cutting guide model for an osteotomy procedure configured to correct the deformity identified by the deformity module 1320. In one embodiment, the provision module 1330 may select a template cutting guide model from a set of template cutting guide models (e.g., a library, set, or repository of template cutting guide models).

The registration module 1340 registers the preliminary cutting guide model with one or more bones or other anatomical structures of the bone model 1304. As explained above, registration is a process of combining medical imaging data, patient imaging data, and/or one or more models such that the preliminary cutting guide model can be used with the bone model 1304.

The design module 1350 designs a patient-specific cutting guide (or patient-specific cutting guide model) based on the preliminary cutting guide model. The design operation of the design module 1350 may be completely automated, partially automated, or completely manual. A user may control how automated or manual the designing of the patient-specific cutting guide (or patient-specific cutting guide model) is.

The manufacturing module 1360 may manufacture a patient-specific cutting guide 1306 using the preliminary cutting guide model. The manufacturing module 1360 may use a patient-specific cutting guide model generated from the preliminary cutting guide model. The manufacturing module 1360 may provide the patient-specific cutting guide model to one or more manufacturing tools and/or fabrication tool. The patient-specific cutting guide model may be sent to the tools in any format such as an STL file or any other CAD modeling or CAM file or method for data exchange. In one embodiment, a user can adjust default parameters for the patient-specific cutting guide such as types and/or thicknesses of materials, dimensions, and the like before the manufacturing module 1360 provides the patient-specific cutting guide model to a manufacturing tool.

Figure 14:
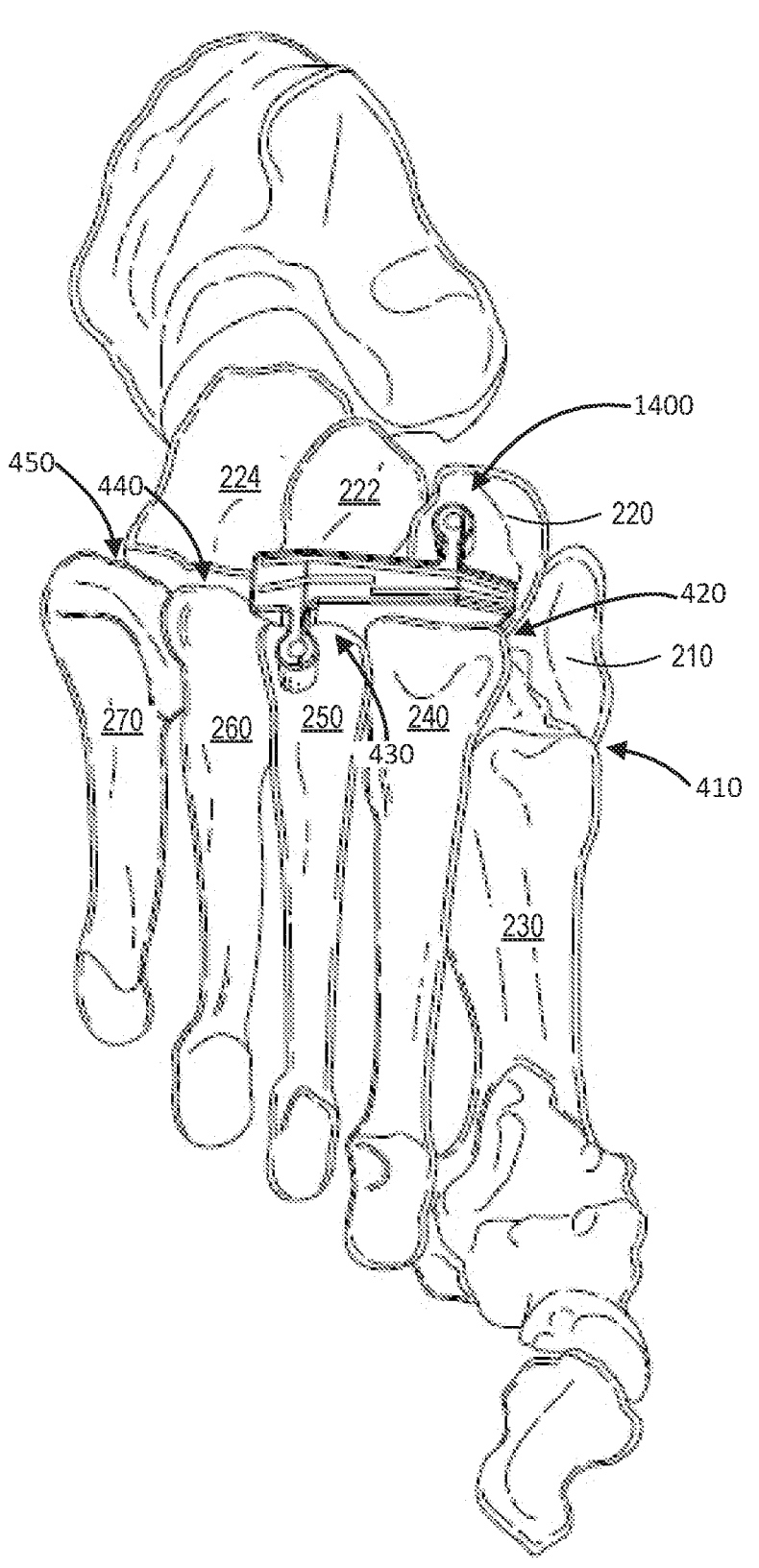
FIG. 14 illustrates a perspective view of a patient-specific cutting guide positioned over adjacent joints of a foot according to one embodiment.

FIG. 14 illustrates a perspective view of a patient-specific cutting guide 1400 positioned over adjacent joints of a foot according to one embodiment. FIG. 14 illustrates some of the bones of a foot. The illustrated bones include bones illustrated in FIG. 2 of a foot 200 and may include a medial cuneiform 210, an intermediate cuneiform 220, a first metatarsal 230, a second metatarsal 240, a third metatarsal 250, a fourth metatarsal 260, and a fifth metatarsal 270. The foot also includes a lateral cuneiform 222 and cuboid 224. The medial cuneiform 210, intermediate cuneiform 220, lateral cuneiform 222, and cuboid 224 (tarsal bones) connect to the metatarsal bones (first metatarsal 230, second metatarsal 240, third metatarsal 250, fourth metatarsal 260, and fifth metatarsal 270) by way of one or more tarsometatarsal joints (TMT joints).

A first TMT joint 410 may include the first metatarsal 230 and the medial cuneiform 210. A second TMT joint 420 may include the second metatarsal 240 and the intermediate cuneiform 220. A third TMT joint 430 may include the third metatarsal 250 and the lateral cuneiform 222. A fourth TMT joint 440 may include the fourth metatarsal 260 and the cuboid 224. A fifth TMT joint 450 may include the fifth metatarsal 270 and the cuboid 224.

In certain instances, a patient may present with a particular foot condition. To address, correct, and/or mitigate effects of the condition a physician may perform one or more osteotomy procedures on the particular foot of the patient. For example, one condition may include a bunion or hallux valgus. The same foot of a patient with a hallux valgus condition may also include a metatarsus adductus condition. Of course, a patient may present with a metatarsus adductus and not also present with the hallux valgus condition. A metatarsus adductus ("MTA"—referred to herein as Metaductus) is a condition in which the one or more metatarsals of the foot are deviated or angled medially toward or past the midline rather than extending substantially straight out from the midfoot. Alternatively, or in addition, one or more metatarsals of the foot may extend more dorsal than others such that the toe at the distal end of the metatarsal does not rest in the same plane as other toes of the foot (a condition referred to as dorsiflexion). Alternatively, or in addition, one or more metatarsals of the foot may extend more plantar than others such that the toe at the distal end of the metatarsal does not rest in the same plane as other toes of the foot (a condition referred to as plantarflexion).

Conventional procedures to address a Metaductus condition are to perform a midfoot arthrodesis. More specifically, a midfoot arthrodesis performed on one or more of the TMT joints. Often, sufficient and desired correction, or mitigation, is achieved by performing a midfoot arthrodesis of the second TMT joint 420 and the third TMT joint 430. Conventional solutions include a surgeon manually making one or more resections of one or more articular surfaces of the second TMT joint 420 and/or third TMT joint 430. Such articular resections may be done without a cutting guide which may raise a risk of an improper resection.

The present disclosure presents one example embodiment of a patient-specific cutting guide 1400 for the second TMT joint 420, the third TMT joint 430, and/or both the second TMT joint 420 and the third TMT joint 430 in the same patient-specific cutting guide 1400. Alternatively, or in addition, the patient-specific cutting guide 1400 may be configured to guide resection of three or more TMT joints with a single patient-specific cutting guide 1400. For example, the patient-specific cutting guide 1400 may be configured to guide resection of the first TMT joint 410, the second TMT joint 420, and the third TMT joint 430.

In addition to providing the features and benefits of a cutting guide for TMT joint arthrodesis procedures, the patient-specific cutting guide 1400 is patient specific. In other words, the patient-specific cutting guide 1400 is a patient-specific instrument. Alternatively, or in addition, the patient-specific cutting guide 1400 may be used in one or more patient-specific osteotomy procedures. Use of a patient-specific cutting guide 1400 can significantly simplify the osteotomy procedures.

FIG. 14 illustrates one example patient-specific cutting guide 1400 positioned dorsal to the second TMT joint 420 and the third TMT joint 430 of a foot of a patient. In certain embodiments, the patient-specific cutting guide 1400 is configured to sit transverse to two or more adjacent joints. In another embodiment, the patient-specific cutting guide 1400 is configured to sit transverse to a single joint of a midfoot of a patient.

In one embodiment, the patient-specific cutting guide 1400 can sit, or seat, dorsal to a first bone, a second bone, a third bone, and a fourth bone of adjacent joints of a patient. In the illustrated embodiment, the patient-specific cutting guide 1400 may sit transverse to adjacent joints: second TMT joint 420 and third TMT joint 430. In such an embodiment, the patient-specific cutting guide 1400 may sit dorsal to a first bone (e.g., intermediate cuneiform 220), a second bone (e.g., second metatarsal 240), a third bone (e.g., lateral cuneiform 222), and a fourth bone (e.g., third metatarsal 250).

In certain embodiments, the patient-specific cutting guide 1400 contacts one or more of each of the first bone, second bone, third bone, and/or fourth bone. The patient-specific cutting guide 1400 may directly contact an exposed cortex of one or more of each of the first bone, second bone, third bone, and/or fourth bone. In another embodiment, the patient-specific cutting guide 1400 may contact soft tissue (or a combination of soft tissue and hard tissue) on a cortex of one or more of each of the first bone, second bone, third bone, and/or fourth bone. In certain embodiments, the patient-specific cutting guide 1400 contacts at least one of a first surface of a first bone, a second surface of a second bone, a third surface of a third bone, and a fourth surface of a fourth bone. As discussed in more detail herein, the patient-specific cutting guide 1400 may include an inferior side having a bone engagement surface shaped to match one or more of the first surface, second surface, third surface, and/or fourth surface.

Those of skill in the art will appreciate that a patient-specific cutting guide 1400 may be used on adjacent joints of a patient other than the examples illustrated and described herein and thus may contact one or more of other bones of those adjacent joints. For example, a patient-specific cutting guide 1400 may sit dorsal to, and be used to, resect one or more bones of a first TMT joint 410 and an adjacent second TMT joint 420, or a third TMT joint 430 and an adjacent fourth TMT joint 440, or any other suitable combination of adjacent joints of a patient.

FIGS. 15A-G are top perspective, top, bottom, right, left, front elevation, and rear elevation views, respectively, of a patient-specific cutting guide 1400 according to one embodiment.

The patient-specific cutting guide 1400 can facilitate resection of one or more of the TMT joints. The patient-specific cutting guide 1400 can include a body 1402 and two or more anchor features, for example a proximal anchor feature 1404 and a distal anchor feature 1406.

In one embodiment, the body 1402 serves as a main structural component of the patient-specific cutting guide 1400. As shown, the body 1402 may have a monolithic construction and the general shape of a rectangular prism. The body 1402 may be configured to reside on the dorsal surfaces of one or more cuneiform bones and/or one or more metatarsal bones to provide desired alignment of the body 1402 with the second TMT joint 420 and/or the third TMT joint 430 and/or fourth TMT joint 440 and/or the fifth TMT joint 450.

In certain embodiments, the body 1402 includes a proximal side 1408, a distal side 1410, a medial side 1412, a lateral side 1414, a superior side 1416, and an inferior side 1418. The proximal side 1408 is the side closest to the trunk of the patient when the cutting guide 1400 is in use. The distal side 1410 is the side furthest from the trunk of the patient when the cutting guide 1400 is in use. The medial side 1412 is the side facing medial when the cutting guide 1400 is in use. The lateral side 1414 is the side facing lateral when the cutting guide 1400 is in use. The superior side 1416 is the side facing up away from the bone(s) when the cutting guide 1400 is in use. The inferior side 1418 is the side facing down, facing and/or contacting the bone(s) (e.g., contacting a surface of one or more bones) when the cutting guide 1400 is in use.

Figures 15A, 15B, 15C:
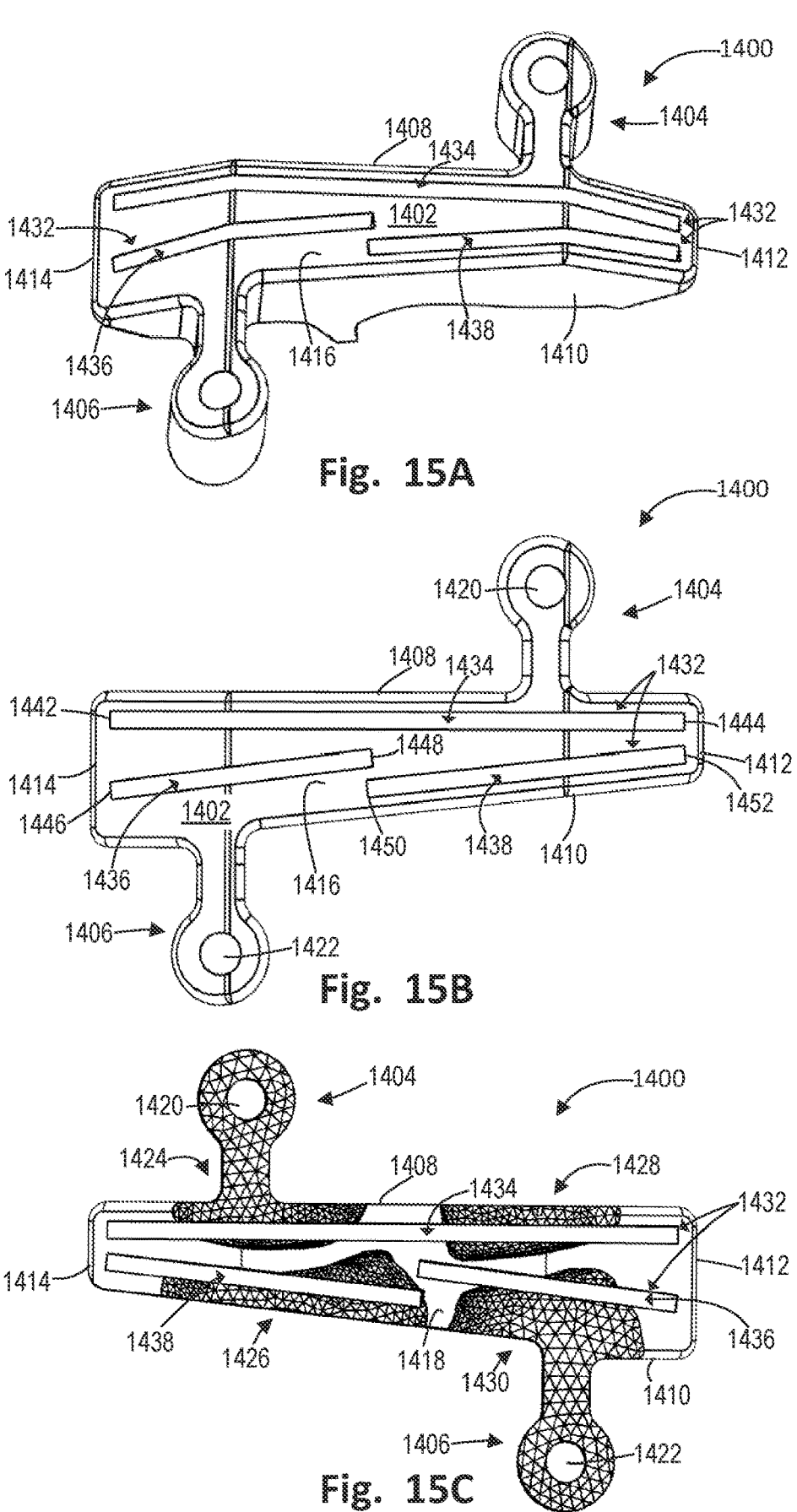

Referring now to FIG. 15B, the two or more anchor features of the patient-specific cutting guide 1400 serve to anchor, attach, or secure the patient-specific cutting guide 1400 to one or more bones of a patient. The two or more anchor features may include any of a wide variety of holes, spikes, fastening devices, and/or the like. As embodied in examples herein, the anchor features may take the form of holes and/or one or more fasteners or fixation devices. The holes may be shaped to accommodate pins, K-wires, and/or other elongated bone fixation elements that can be anchored in bone to keep the patient-specific cutting guide 1400 in place.

The two or more anchor features may be coupled to the body 1402 and configured to accept or receive two or more fasteners to anchor the body 1402 to one or more bones of a patient. In one embodiment, the two or more anchor features may include one or more features that accept fasteners that cooperate with the two or more anchor features to secure the patient-specific cutting guide 1400 to one or more bones of a patient.

In one embodiment, the proximal anchor feature 1404 extends from the proximal side 1408 of the body 1402. The proximal anchor feature 1404 may extend such that the proximal anchor feature 1404 is dorsal to one of two bones on a proximal side of two adjacent joints. For example, the proximal anchor feature 1404 may extend such that the proximal anchor feature 1404 is dorsal to one of the intermediate cuneiform 220 (e.g., first bone) and the lateral cuneiform 222 (e.g., third bone). Alternatively, or in addition, the body 1402 may include two or more proximal anchor features. One proximal anchor feature may extend dorsal to the intermediate cuneiform 220 and another proximal anchor feature may extend dorsal to the lateral cuneiform 222. The distal anchor feature 1406 may extend from the distal side 1410 of the body 1402. The distal anchor feature 1406 may extend such that the distal anchor feature 1406 is dorsal to one of two bones on a distal side of two adjacent joints. For example, the distal anchor feature 1406 may extend such that the distal anchor feature 1406 is dorsal to one of the second metatarsal 240 (e.g., second bone) and the third metatarsal 250 (e.g., fourth bone). Alternatively, or in addition, the body 1402 may include two or more distal anchor features. One distal anchor feature may extend dorsal to the second metatarsal 240 and another distal anchor feature may extend dorsal to the third metatarsal 250.

In the illustrated embodiment, the each of the two or more anchor features may include at least one hole that passes through the anchor feature. For example, proximal anchor feature 1404 may include hole 1420 and distal anchor feature 1406 may include hole 1422. Each hole 1420, 1422 may be configured and/or sized to accept one or more fasteners (e.g., a pin, K-wire, screw, or the like). The fastener may pass through the hole 1420, 1422 and engage one or more bones of a patient to anchor the patient-specific cutting guide 1400.

FIG. 15C illustrates a bottom view of the patient-specific cutting guide 1400 of FIGS. 15A, 15B. FIG. 15C illustrates the inferior side 1418 of the body 1402. The inferior side 1418 facilitates placement, positioning and anchoring of the body 1402 to the one or more bones of one or more joints, such as two adjacent joints. In certain embodiments, the inferior side 1418 includes one or more features to facilitate placement, positioning and anchoring of the body 1402.

In one embodiment, the inferior side 1418 includes a bone engagement surface shaped to match at least one of a first surface of a first bone, a second surface of a second bone, a third surface of a third bone, and a fourth surface of a fourth bone of adjacent joints. FIG. 15C illustrates example recesses 1424, 1426, 1428, 1430 that can match bone surfaces of one or more, such as four bones of adjacent joints (e.g., second TMT joint 420 and third TMT joint 430).

Referring now to FIGS. 15A-C, the body 1402 may also include one or more guide features 1432. The one or more guide features 1432 guide a cutting tool to resect one or more bones. In one embodiment, the one or more guide features 1432 guide resection for an osteotomy of, at, or near an articular surface of a bone. Alternatively, or in addition, the one or more guide features 1432 guide resection for an osteotomy of, at, or near any section, region, or portion of a bone. "Cutting tool" refers to any tool that can be used to cut or resect another object. In particular, a cutting tool can refer to a manual or power tool for cutting or resecting tissue of a patient. Examples, of cutting tools include, but are not limited to, a burr, an oscillating saw, a reciprocating saw, a grater saw, a drill, a mill, a side-cutting burr, or the like. In one embodiment, the one or more guide features 1432 may cooperate with one or more bone engagement surfaces overlying one or more adjacent joints to guide the resection of at least one of the first bone, the second bone, the third bone, and/or the fourth bone during an osteotomy. In addition, the one or more guide features 1432 may be positioned, sized, and/or oriented within the body 1402 to guide one or more resection operations in the osteotomy.

In certain embodiments, the one or more guide features 1432 are straight and enable a surgeon to make a planar cut or resection. Alternatively, or in addition, the one or more guide features 1432 may include one or more angles and/or curves and enable a surgeon to make a cut or resection that corresponds to the configuration of the one or more guide features 1432.

In the illustrated embodiment of FIG. 15A-G, the one or more guide features 1432 may include a first guide feature, a second guide feature, and a third guide feature and may take the form of a first slot 1434, a second slot 1436, and a third slot 1438. The first slot 1434 may include a lateral end 1442 and a medial end 1444. The second slot 1436 may include a lateral end 1446 and a medial end 1448. The third slot 1438 may include a lateral end 1450 and a medial end 1452. Those of skill in the art will appreciate that the patient-specific cutting guide may include one, two, three, four, or more guide features 1432.

In one embodiment, the first slot 1434, second slot 1436, and the third slot 1438 may extend from the superior side 1416 to the inferior side 1418. In certain embodiments, the first slot 1434 may extend from near the medial side 1412 to near the lateral side 1414. The second slot 1436 may extend from near the lateral side 1414 to near a central portion of the body 1402. The third slot 1438 may extend from near a central portion of the body 1402 to near the medial side 1412. In certain embodiments, one or more of the slots may intersect to form a single or a composite slot.

Referring now to FIGS. 14, 15A-C, the body 1402 is configured to seat transverse to adjacent joints (e.g., second TMT joint 420 and third TMT joint 430) with the bone engagement surface engaging at least one of the first surface, the second surface, the third surface, and the fourth surface a first surface of a first bone (e.g., intermediate cuneiform 220), a second surface of a second bone (e.g., second metatarsal 240), a third surface of a third bone (e.g., lateral cuneiform 222), and a fourth surface of a fourth bone (e.g., third metatarsal 250).

FIG. 15D illustrates the patient-specific cutting guide 1400 from a view facing the lateral side 1414. FIG. 15E illustrates the patient-specific cutting guide 1400 from a view facing the medial side 1412.

In certain embodiments, the patient-specific cutting guide 1400 may include one or more features that facilitate use of the patient-specific cutting guide 1400 while avoiding certain soft tissue in the vicinity of one or more joints.

For example, the lateral side 1414 may include a lateral superior surface 1458 and a lateral inferior surface 1460 that meet at a lateral edge 1462. In another example, the medial side 1412 may include a medial superior surface 1464 and a medial inferior surface 1466 that meet at a medial edge 1468.

In one embodiment, the lateral superior surface 1458 may extend from the superior side 1416 to the lateral edge 1462 at an angle. In certain embodiments, the angle may range between about 80 and about 170 degrees. The angle of the lateral superior surface 1458 may enable use of the patient-specific cutting guide 1400 in tighter openings and/or spaces and thus minimize the size of incisions used for a procedure. Similarly, the lateral inferior surface 1460 may extend from inferior side 1418 to the lateral edge 1462 at an angle such that the lateral inferior surface 1460 does not impinge soft tissue near a joint (e.g., near at least one joint of adjacent joints). In certain embodiments, the angle may range between about 80 and about 170 degrees.

Of course, the medial superior surface 1464 may extend from the superior side 1416 to the medial edge 1468 at an angle. The angle of the medial superior surface 1464 may enable use of the patient-specific cutting guide 1400 in tighter openings and/or spaces and thus minimize the size of incisions used for a procedure. Advantageously, the medial inferior surface 1466 may extend from inferior side 1418 to the medial edge 1468 at an angle such that the medial inferior surface 1466 does not impinge soft tissue near a joint (e.g., near at least one joint of adjacent joints). In certain embodiments, the angle may range between about 80 and about 170 degrees. In the illustrated embodiment of FIGS. 15D and 15E, each of the lateral superior surface 1458, medial superior surface 1464, lateral inferior surface 1460, and medial inferior surface 1466 may extend to one of the lateral edge 1462 and/or medial edge 1468 at an angle.

Alternatively, or in addition, each extension angle may be the same or may be different. Those of skill in the art will appreciate that the extension angle may be zero. Some extension angles may be the same and/or each of the extension angles may be different. Alternatively, or in addition, in certain embodiments, an extension angle for one or more of the lateral superior surface 1458, medial superior surface 1464, lateral inferior surface 1460, and medial inferior surface 1466 may be determined based on patient imaging data. For example, patient imaging data may indicate the presence of a neurovascular structure near a joint and one or more extension angles for the one or more of the lateral superior surface 1458, medial superior surface 1464, lateral inferior surface 1460, and medial inferior surface 1466 may be defined to avoid impingement of the neurovascular structure by the patient-specific cutting guide 1400.

Figures 16A, 16B, 16C:
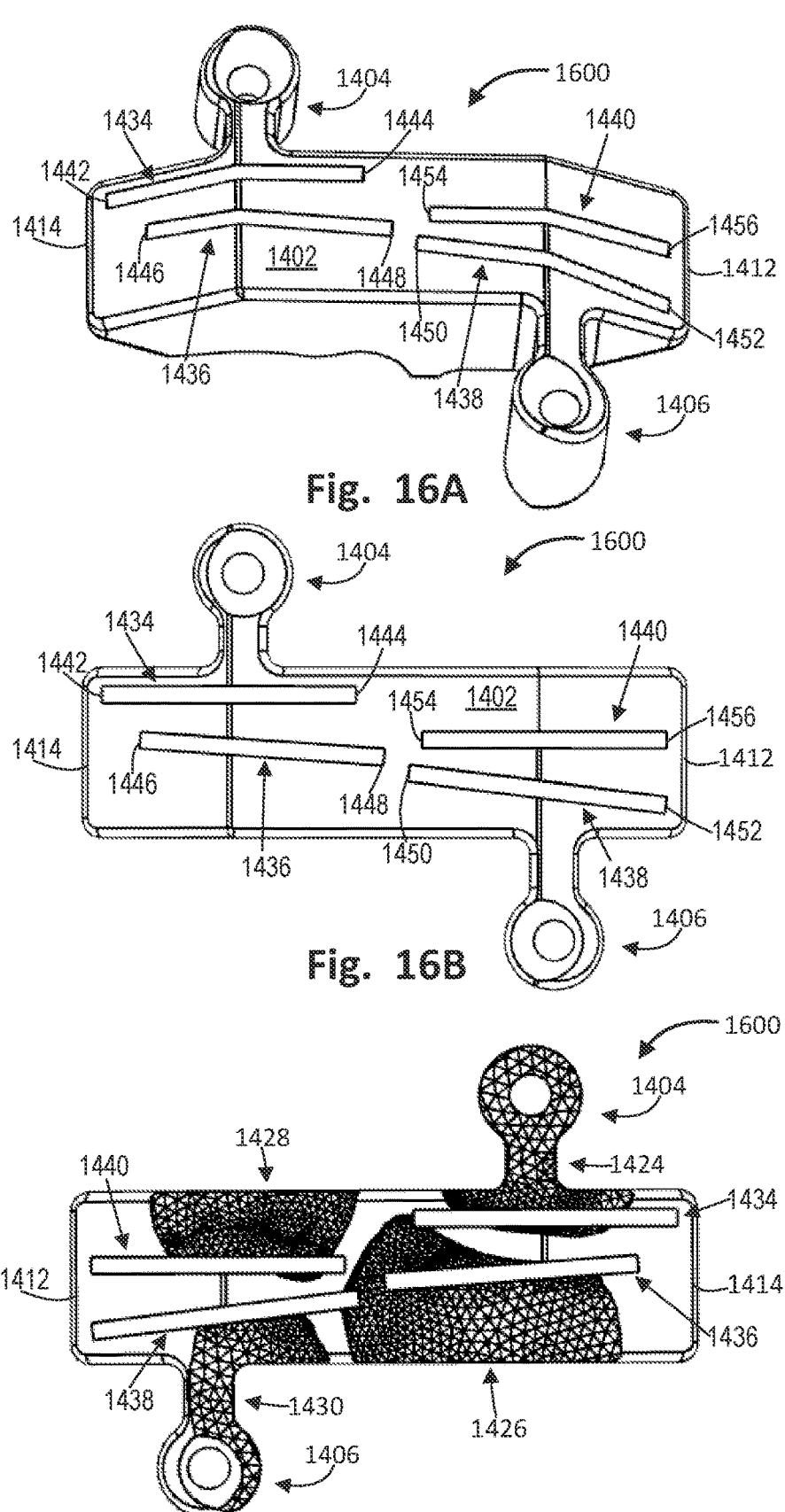
FIGS. 16A-C are top perspective, top, and bottom views, respectively, of a patient-specific cutting guide according to one embodiment.

FIGS. 16A-C are top perspective, top, and bottom views, respectively, of a patient-specific cutting guide 1600 according to one embodiment. In the illustrated embodiment of FIG. 16A-C, the one or more guide features 1432 may include a first guide feature, a second guide feature, a third guide feature, and a fourth guide feature and may take the form of a first slot 1434, a second slot 1436, a third slot 1438, and a fourth slot 1440. The fourth slot 1440 may also include a lateral end 1454 and a medial end 1456.

In one embodiment, the first slot 1434, second slot 1436, third slot 1438, and the fourth slot 1440 may extend from the superior side 1416 to the inferior side 1418. In certain embodiments, the first slot 1434 may extend from near the lateral side 1414 to near a central portion of the body 1402. The second slot 1436 may extend from near the lateral side 1414 to near a central portion of the body 1402. The third slot 1438 may extend from near a central portion of the body 1402 to near the medial side 1412. The fourth slot 1440 may extend from near a central portion of the body 1402 to near the medial side 1412.

FIGS. 16A-C includes a patient-specific cutting guide 1600 having similar components, parts, devices, apparatus, features, and aspects as those disclosed and described in relation to the embodiment of FIGS. 15A-15G, however one difference in FIGS. 16A-C is that the one or more guide features 1432 includes a fourth slot 1440.

In certain embodiments, the number of one or more guide features 1432, their position within the body 1402, their orientation, their size, and/or their shape may be determined based on anatomical data about the patient, anatomical structures of the patient, the osteotomy procedure to be performed, preferences of the surgeon, the nature of a condition, and the like. In one embodiment, the patient-specific cutting guide 1600 is configured for use on a second TMT joint 420 and a third TMT joint 430 of a patient. Accordingly, the first slot 1434 may be configured to guide resection of a lateral cuneiform 222, the second slot 1436 may be configured to guide resection of a third metatarsal 250, the third slot 1438 may be configured to guide resection of a second metatarsal 240, and the fourth slot 1440 may be configured to guide resection of an intermediate cuneiform 220.

FIG. 16C illustrates that the patient-specific cutting guide 1600 may include a recess 1424 configured to contact and/or fit at least a portion of the lateral cuneiform 222, a recess 1426 configured to contact and/or fit at least a portion of the third metatarsal 250, a recess 1428 configured to contact and/or fit at least a portion of the intermediate cuneiform 220, a recess 1430 configured to contact and/or fit at least a portion of the second metatarsal 240. Those of skill in the art will recognize that while FIG. 16C illustrates a patient-specific cutting guide 1600 that includes recess 1424, recess 1426, recess 1428, and recess 1430, the patient-specific cutting guide 1600 may include fewer than the number of recesses illustrated depending on the anatomical structures of the patient, the osteotomy procedure being performed, preferences of the surgeon, the nature of a condition, and the like.

Figures 17A, 17B, 17C:
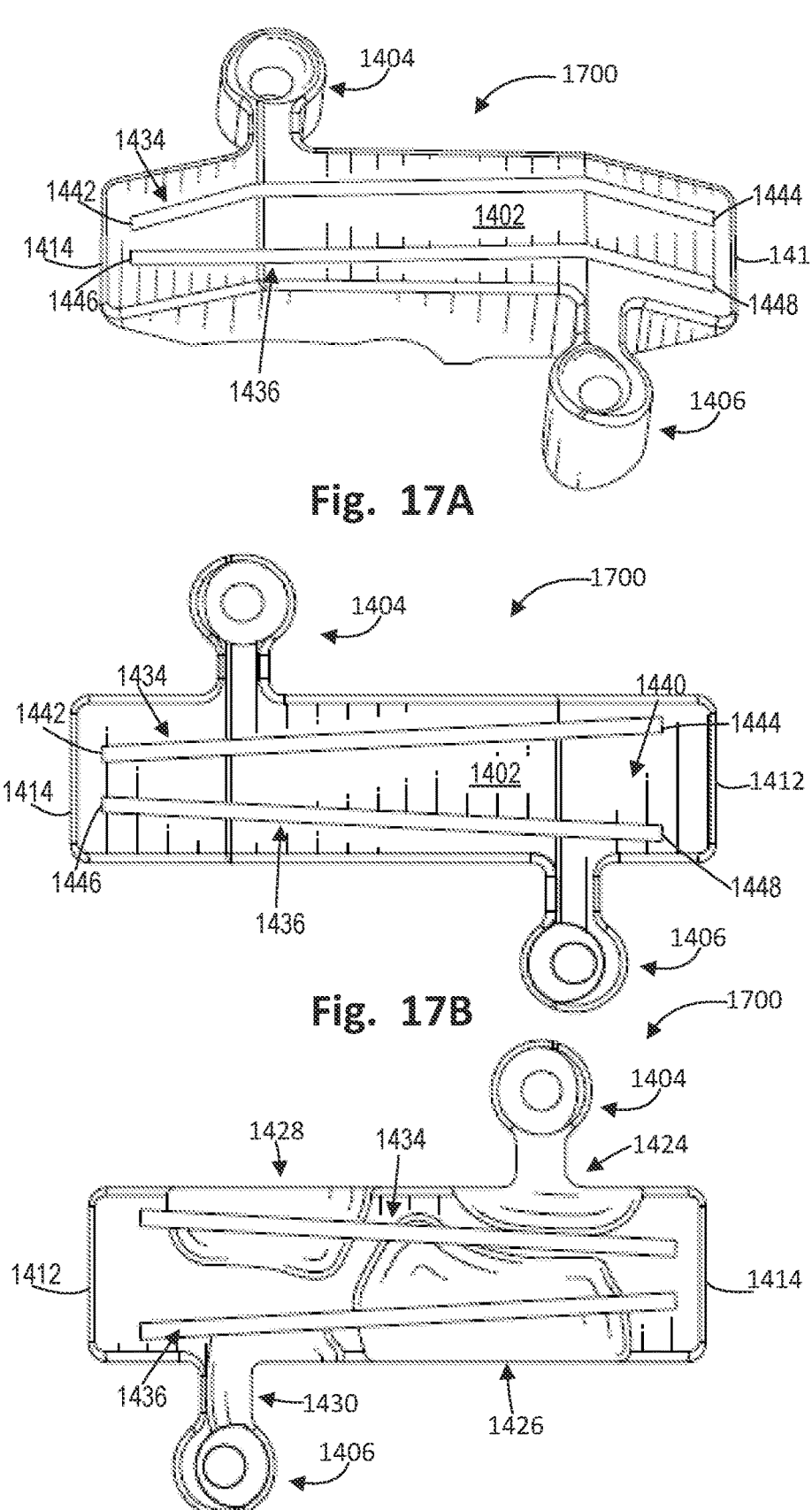
FIGS. 17A-C are top perspective, top, and bottom views, respectively, of a patient-specific cutting guide according to one embodiment.

FIGS. 17A-C includes a patient-specific cutting guide 1700 having similar components, parts, devices, apparatus, features, and aspects as those disclosed and described in relation to the embodiment of FIGS. 15A-15G, however one difference in FIGS. 17A-C is that the one or more guide features 1432 includes a first slot 1434 and a second slot 1436.

In certain embodiments, the number of one or more guide features 1432, their position within the body 1402, their orientation, their size, and/or their shape may be determined based on anatomical data about the patient, anatomical structures of the patient, the osteotomy procedure to be performed, preferences of the surgeon, the nature of a condition, and the like. In one embodiment, the patient-specific cutting guide 1700 is configured for use on a second TMT joint 420 and a third TMT joint 430 of a patient. Accordingly, the first slot 1434 may be configured to guide resection of at least a portion of a lateral cuneiform 222 and/or a portion of intermediate cuneiform 220. The second slot 1436 may be configured to guide resection of at least a portion of a third metatarsal 250 and/or a portion of a second metatarsal 240.

FIG. 17C illustrates that the patient-specific cutting guide 1700 may include a recess 1424 configured to contact and/or fit at least a portion of the lateral cuneiform 222, a recess 1426 configured to contact and/or fit at least a portion of the third metatarsal 250, a recess 1428 configured to contact and/or fit at least a portion of the intermediate cuneiform 220, a recess 1430 configured to contact and/or fit at least a portion of the second metatarsal 240. Those of skill in the art will recognize that while FIG. 17C illustrates a patient-specific cutting guide 1700 that includes recess 1424, recess 1426, recess 1428, and recess 1430, the patient-specific cutting guide 1700 may include fewer than the number of recesses illustrated depending on the anatomical structures of the patient, the osteotomy procedure being performed, preferences of the surgeon, the nature of the condition, and the like.

Figures 18A, 18B, 18C:
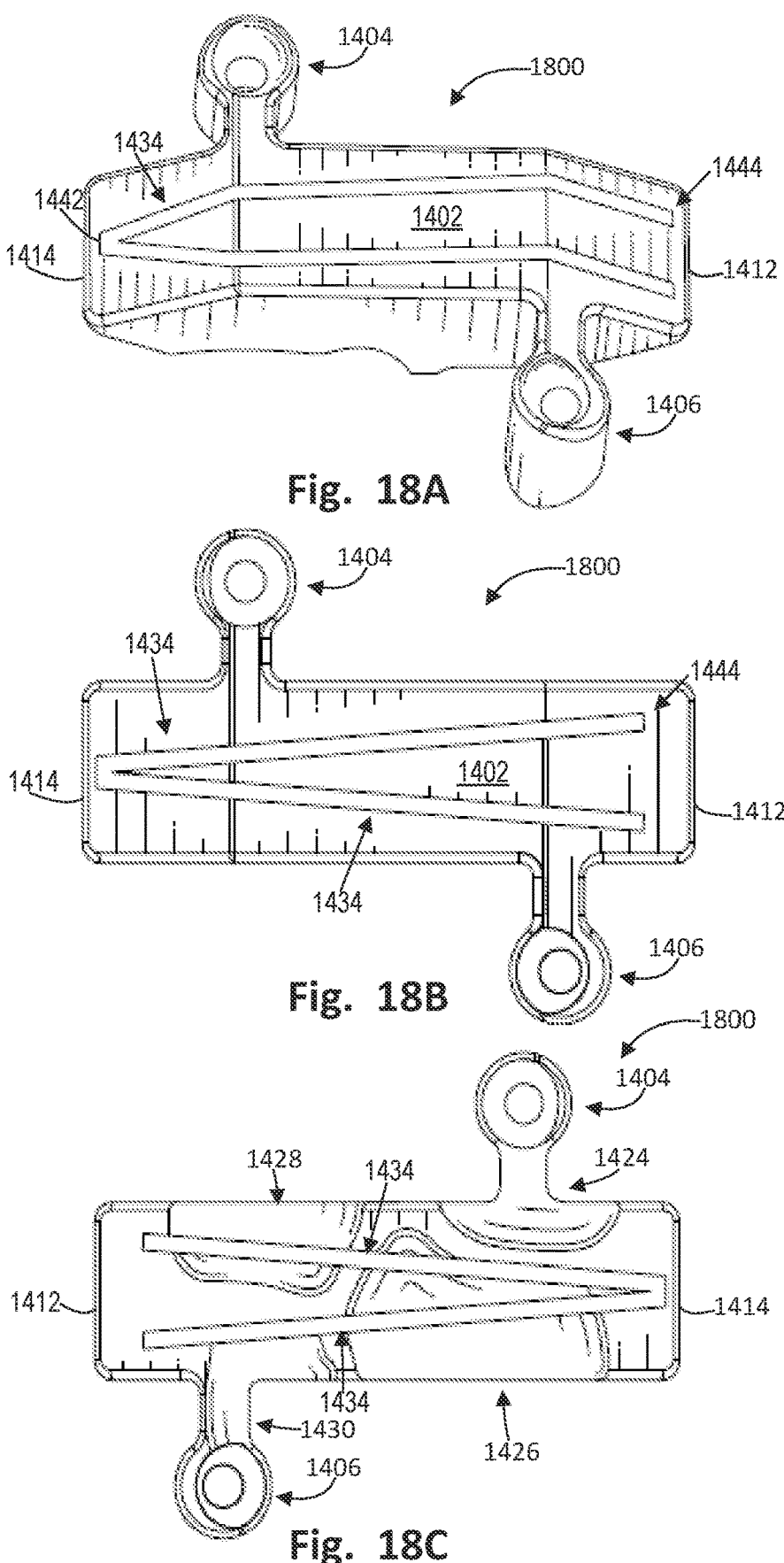
FIGS. 18A-C are top perspective, top, and bottom views, respectively, of a patient-specific cutting guide according to one embodiment.

FIGS. 18A-C includes a patient-specific cutting guide 1800 having similar components, parts, devices, apparatus, features, and aspects as those disclosed and described in relation to the embodiment of FIGS. 15A-15G, however one difference in FIGS. 18A-C is that the one or more guide features 1432 includes a first slot 1434. More particularly, the first slot 1434 is shaped like a "V" (lying on its side). In certain embodiments, the lateral end 1442 may include two parts of the "V" shape that come together and are connected to form the single first slot 1434. The medial end 1444 may include two top parts of a "V" shape that are separated near the recess 1424.

In certain embodiments, the number of one or more guide features 1432, their position within the body 1402, their orientation, their size, and/or their shape may be determined based on anatomical data about the patient, anatomical structures of the patient, the osteotomy procedure to be performed, preferences of the surgeon, the nature of a condition, and the like. In one embodiment, the patient-specific cutting guide 1800 is configured for use on a second TMT joint 420 and a third TMT joint 430 of a patient. Accordingly, the first slot 1434 may be configured to guide resection of at least a portion of a lateral cuneiform 222 and/or a portion of intermediate cuneiform 220 and/or at least a portion of a third metatarsal 250 and/or a portion of a second metatarsal 240.

FIG. 18C illustrates that the patient-specific cutting guide 1800 may include a recess 1424 configured to contact and/or fit at least a portion of the lateral cuneiform 222, a recess 1426 configured to contact and/or fit at least a portion of the third metatarsal 250, a recess 1428 configured to contact and/or fit at least a portion of the intermediate cuneiform 220, a recess 1430 configured to contact and/or fit at least a portion of the second metatarsal 240. Those of skill in the art will recognize that while FIG. 18C illustrates a patient-specific cutting guide 1700 that includes recess 1424, recess 1426, recess 1428, and recess 1430, the patient-specific cutting guide 1700 may include fewer than the number of recesses illustrated depending on the anatomical structures of the patient, the osteotomy procedure being performed, preferences of the surgeon, the nature of the condition, and the like.

Figure 19:
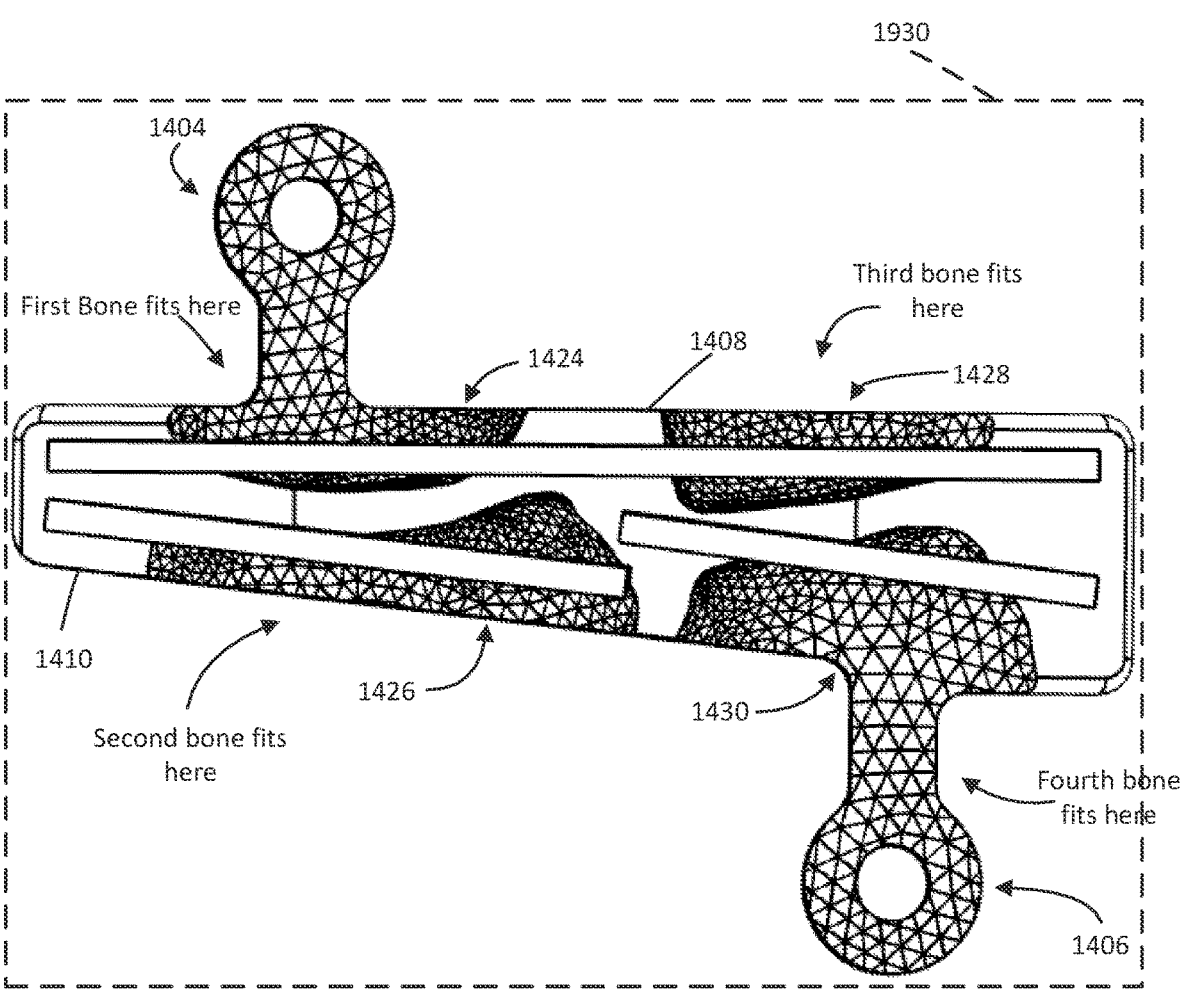
FIG. 19 is a bottom view of patient-specific cutting guide according to one embodiment.

FIG. 19 is a bottom view of patient-specific cutting guide 1400 according to one embodiment. The inferior side 1418 may include a bone engagement surface 1930 shaped to match at least one of a first surface of a first bone, a second surface of a second bone, a third surface of a third bone, and a fourth surface of a fourth bone of adjacent joints. For example in one embodiment, the bone engagement surface 1930 may include recesses 1424, 1426, 1428, 1430 that may match bone surfaces of one or more bones, such as four bones of adjacent joints (e.g., second TMT joint 420 and third TMT joint 430). The bone engagement surface 1930 may be shaped to include some, or all, of the inferior side 1418.

In one example, a recess 1424 of the bone engagement surface 1930 can be shaped such that the recess 1424 matches a surface of an intermediate cuneiform 220 and a recess 1426 of the bone engagement surface 1930 matches a surface of a second metatarsal 240 of a second TMT joint 420. In addition, the recess 1428 of the bone engagement surface 1930 can be shaped such that the recess 1428 matches a surface of lateral cuneiform 222 and a recess 1430 of the bone engagement surface 1930 matches a surface of third metatarsal 250 of a third TMT joint 430. The bone engagement surface 1930 can be so shaped because it is fabricated from a bone model of the patient's bones. The body 1402 is configured, designed, and/or fabricated to seat transverse to one or more TMT joints.

Based on the location and position of the recesses, the recess 1424 and recess 1428 may be referred to as a first proximal bone recess 1424 and a second proximal bone recess 1428. Alternatively, or in addition, the first proximal bone recess 1424 may be referred to as a first proximal medial bone recess 1424 and the second proximal bone recess 1428 may be referred to as a second proximal lateral bone recess 1428. Similarly, the recess 1426 and recess 1430 may be referred to as a first distal bone recess 1426 and a second distal bone recess 1430. Alternatively, or in addition, the first distal bone recess 1426 may be referred to as a first distal medial bone recess 1426 and the second distal bone recess 1430 may be referred to as a second distal lateral bone recess 1430. The first proximal bone recess 1424 is opposite the first distal bone recess 1426 and the second proximal bone recess 1428 is opposite the second distal bone recess 1430.

Advantageously, a first bone (e.g., intermediate cuneiform 220) can fit within the first proximal bone recess 1424, a second bone (e.g., second metatarsal 240) can fit within the first distal bone recess 1426, a third bone (e.g., lateral cuneiform 222) can fit within the second proximal bone recess 1428, a fourth bone (e.g., third metatarsal 250) can fit within the second distal bone recess 1430. Those of skill in the art will appreciate that the bone engagement surface 1930 may include more or fewer than the recesses 1424, 1426, 1428, and 1430 illustrated in FIG. 19. In one embodiment, the bone engagement surface 1930 can include a single recess (e.g., a contour), a plurality of recesses, a single projection, a plurality of projections, and/or any combination of these.

In one embodiment, the body 1402 is configured to reside on the dorsal surfaces of the intermediate cuneiform 220, lateral cuneiform 222, second metatarsal 240, and third metatarsal 250 to provide proper alignment of the body 1402 with second TMT joint 420 and third TMT joint 430. As shown, the recesses 1424, 1426, 1428, and 1430 may be contoured to match the contour of the surface of the bones on which they are to rest. Said another way, the recesses 1424, 1426, 1428, and 1430 cooperate with other parts of the bone engagement surface 1930 to provide a topography that corresponds to the topography of two adjacent joints and/or the bones that form the joints and/or any articular surfaces of the joints. Thus, the body 1402 may have only one stable position and orientation relative to the TMT joints during a surgical osteotomy for correcting a condition. Those of skill in the art will appreciate that the adjacent joints can be the second TMT joint 420 and the third TMT joint 430 or the first TMT joint 410 and the second TMT joint 420 or the fourth TMT joint 440 and the third TMT joint 430 or the like.

Advantageously, the fidelity of the patient imaging data enables the bone model, preliminary cutting guide model, and patient-specific instrument (e.g., patient-specific cutting guide, patient-specific pin guide, patient-specific alignment guide, etc.) to uniquely match a particular patient. Consequently, the bone engagement surface 1930 can engage the surfaces of the bones of one or more joints in a single configuration. Such a close matching fit facilitates the surgical osteotomy.

Referring still to FIG. 19, in one embodiment, the recesses 1424, 1426, 1428, and 1430 may include parts of the proximal anchor feature 1404 and/or the distal anchor feature 1406. For example, in one embodiment, the first proximal bone recess 1424 can include an inferior surface of the proximal anchor feature 1404 (which inferior surface may be contoured to match a surface of a bone (e.g., intermediate cuneiform 220)). Similarly. The second distal bone recess 1430 can include an inferior surface of the distal anchor feature 1406 (which inferior surface may be contoured to match a surface of a bone (e.g., third metatarsal 250)).

Figure 20:
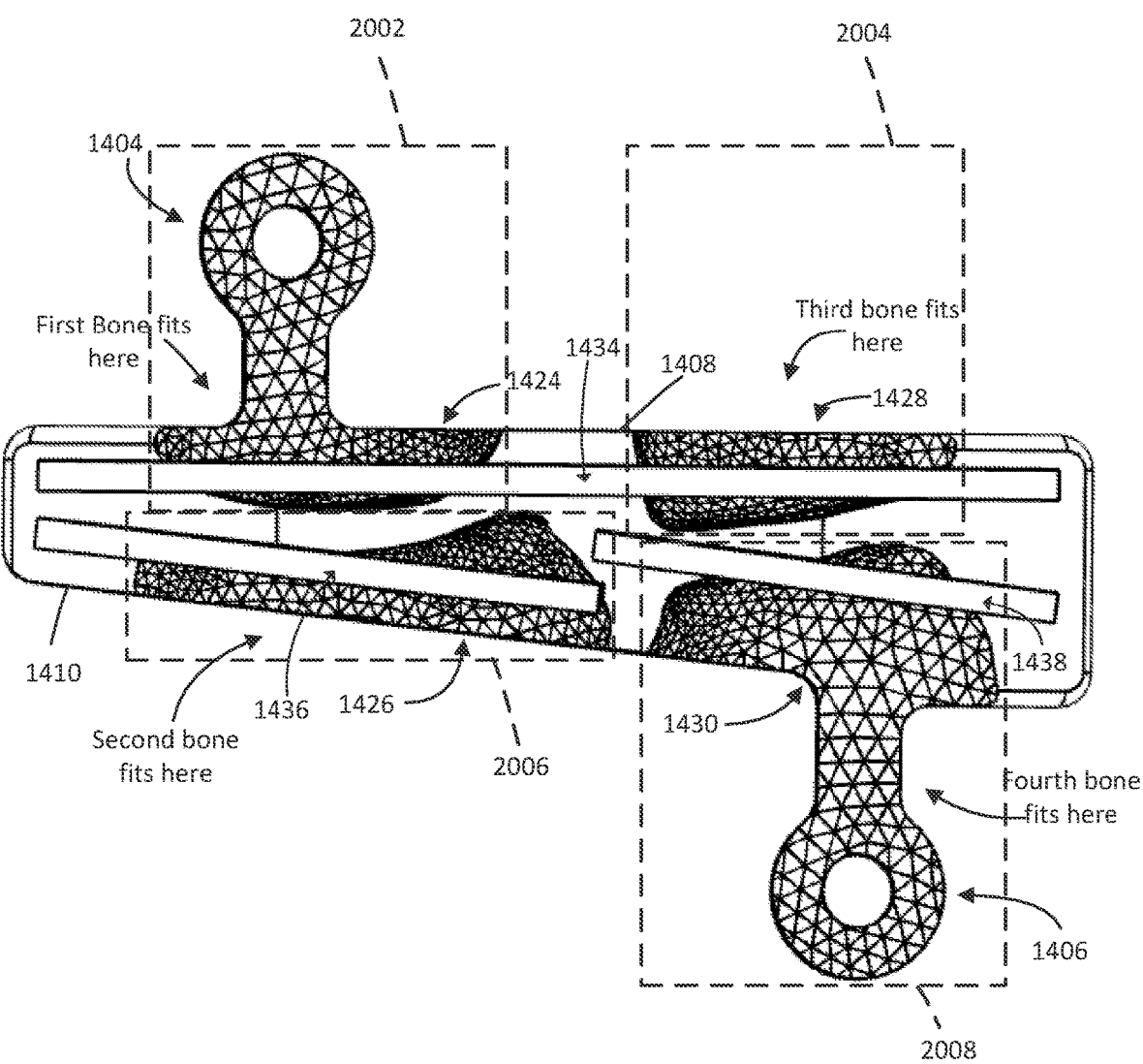
FIG. 20 is a bottom view of patient-specific cutting guide according to one embodiment.

FIG. 20 is a bottom view of patient-specific cutting guide 1400 according to one embodiment. The inferior side 1418 may include a plurality of bone engagement surfaces. For example, in the embodiment illustrated in FIG. 20, the inferior side 1418 may include four bone engagement surfaces 2002, 2004, 2006, 2008. Each of these four bone engagement surfaces 2002, 2004, 2006, 2008 may be contoured inferior surfaces that together make up an inferior surface of the patient-specific cutting guide 1400.

The plurality of bone engagement surfaces may be shaped to correspond to at least a portion of a surface topography of at least one bone of adjacent joints. For example, bone engagement surface 2002 can be shaped to match at least one of at least a portion of a surface of a first bone (e.g., intermediate cuneiform 220). Bone engagement surface 2004 can be shaped to match at least one of at least a portion of a surface of a second bone (e.g., lateral cuneiform 222).

Bone engagement surface 2006 can be shaped to match at least one of at least a portion of a surface of a third bone (e.g., second metatarsal 240). Bone engagement surface 2008 can be shaped to match at least one of at least a portion of a surface of a fourth bone (e.g., third metatarsal 250). The bone engagement surfaces 2002, 2004, 2006, 2008 may be configured to engage surfaces and/or voids within one or more or two or more adjacent joints (e.g., second TMT joint 420 and third TMT joint 430). In certain embodiments, a bone engagement surface 1930 and/or a plurality of bone engagement surfaces 2002, 2004, 2006, 2008 are configured to enable the patient-specific cutting guide 1400 to seat transverse to the adjacent joints with the plurality of bone engagement surfaces 2002, 2004, 2006, 2008 engaging bones of the adjacent joints.

In one embodiment, a bone engagement surface 1930 and/or bone engagement surfaces 2002, 2004, 2006, 2008 may be formed by creating contours or recesses within a planar or substantially planar (e.g., lateral inferior surface 1460 and/or medial inferior surface 1466) inferior side 1418. Alternatively, or in addition, bone engagement surface 1930 and/or bone engagement surfaces 2002, 2004, 2006, 2008 can also include one or more projections formed on or as part of an inferior side 1418.

Those of skill in the art will appreciate that a bone engagement surface 1930 and/or plurality of bone engagement surfaces 2002, 2004, 2006, 2008 may be configured to "engage with" a bone surface of one or more bones of a joint or adjacent joints or may be "shaped to match" at least one of the surfaces of at least one of the bones of a joint or adjacent joints. A bone engagement surface that "engages with" a bone surface of one or more bones of a joint and a bone engagement surface that is "shaped to match" a bone surface of one or more bones of a joint or adjacent joints may differ in the amount of contact, engagement, or interaction between a surface of the one or more bones and one or more aspects of the bone engagement surface. For example, a bone engagement surface that is "shaped to match" a bone surface of one or more bones of a joint or adjacent joints may include a surface that is shaped to include a topography that is an inverse of the topography of the one or more bones of a joint or adjacent joints.

Figure 21A:
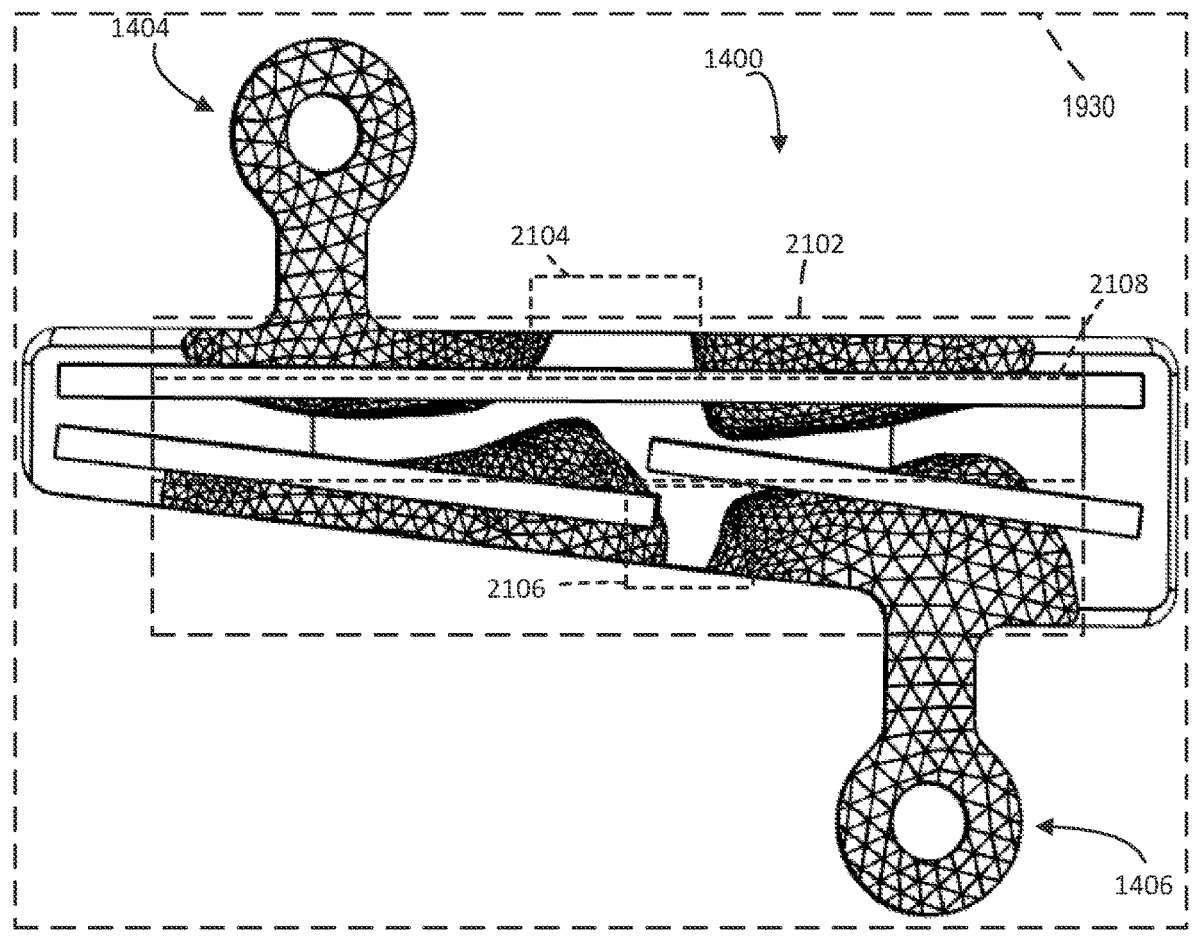
FIG. 21A is a bottom view of patient-specific cutting guide according to one embodiment.

FIG. 21A is a bottom view of patient-specific cutting guide 1400 according to one embodiment. The patient-specific cutting guide 1400 may include a bone engagement surface 1930 that can include one or more or all of the features on the inferior side 1418. In one embodiment, the bone engagement surface 1930 is custom contoured to match the shapes of one or more bones of one or more joints (e.g., adjacent joints). In certain embodiments, the bone engagement surface 1930 includes a registration key 2102. The registration key 2102 is configured to fit between the bones of adjacent joints and may include a set of features. "Registration key" refers to a structure, surface, feature, module, component, apparatus, and/or system that facilitates, enables, guides, promotes, precision in the alignment of two objects by way of registration. In one aspect a registration key can include a surface and one or more recesses and/or features of that surface that are configured to fit within corresponding recesses, projections, and/or other features of another structure such as another surface. In one aspect a registration key can include a surface and one or more projections and/or features of, extending from, or connected to that surface that are configured to fit within corresponding recesses, projections, and/or other features of another structure such as another surface. In certain aspects, the features of the registration key may be configured to fit within, or in contact, or in close contact with those of the another structure. In one embodiment, when the two structures align the registration key has served its purpose. In certain embodiments, the registration key 2102 may include one or more structures of the inferior side 1418 that extend down into one or more of the adjacent joints and/or between the bones.

The registration key 2102 facilitates a desired alignment and placement of the patient-specific cutting guide 1400 on the adjacent joints. It should be noted that the adjacent joints can be two adjacent joints of which one or more bones of the joints are to be resected (e.g., third TMT joint 430 and second TMT joint 420). However, the adjacent joints that receive the registration key 2102 can also include one joint that will be resected and an adjacent joint whose bones are not to be resected (e.g., second TMT joint 420 and first TMT joint 410). The registration key 2102 can be formed by a variety of structures, including recesses, planar parts of an inferior side 1418, angled parts of an inferior side 1418, one or more projections added to an inferior side 1418, openings in guide features, and the like.

In the example of FIG. 21A, the registration key 2102 can include the area of the inferior side 1418 that includes the recesses 1422, 1424, 1426, 1428. The registration key 2102 can be further divided into a proximal projection 2104, a distal projection 2106, and a midsection projection 2108 between the proximal projection 2104 and the distal projection 2106. The proximal projection 2104 is near and may include one or more parts of the proximal side 1408. The distal projection 2106 is near and may include one or more parts of the distal side 1410. The midsection projection 2108 is between the proximal projection 2104 and the distal projection 2106. The proximal projection 2104, distal projection 2106, and midsection projection 2108 facilitate the patient-specific cutting guide 1400 in seating onto the adjacent joints of the patient.

Figure 21B:
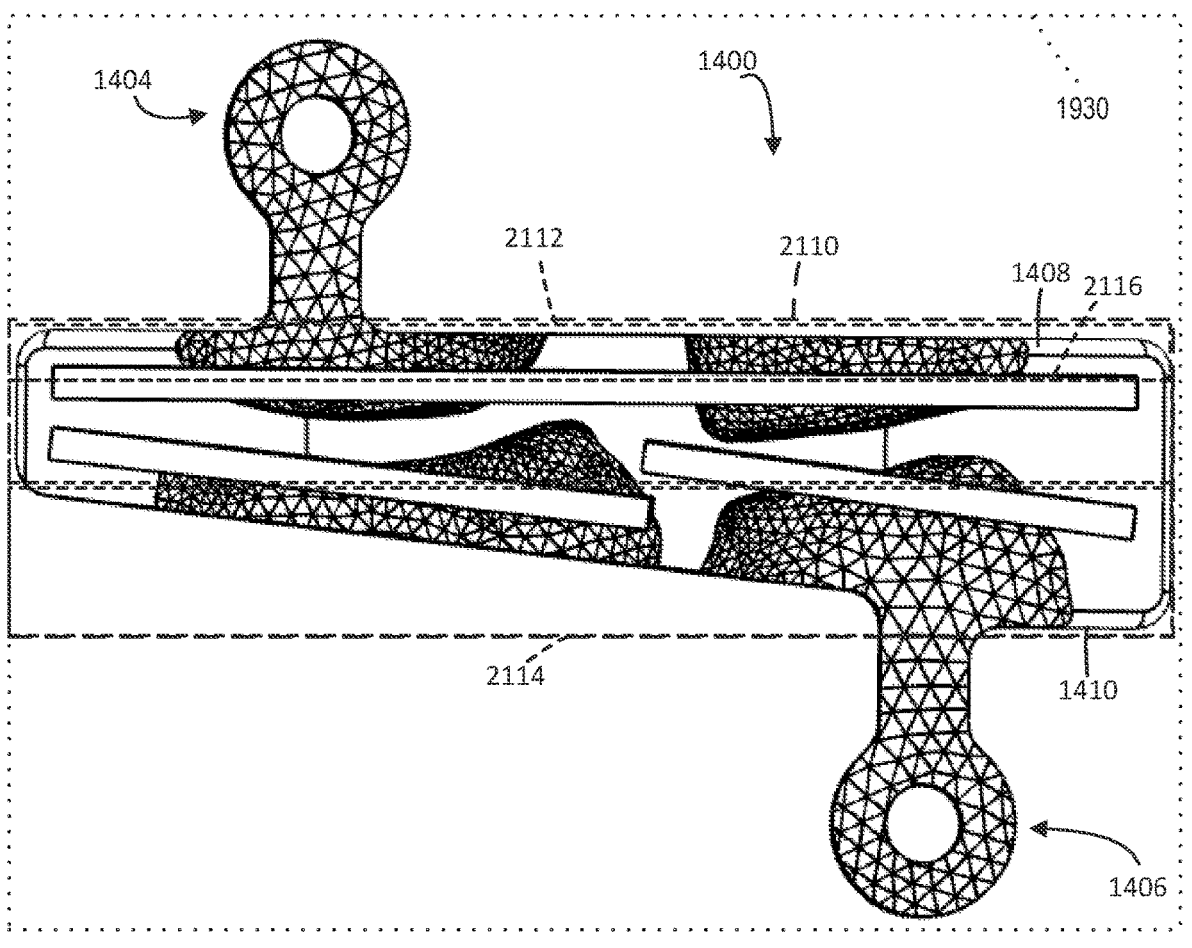
FIG. 21B is a bottom view of patient-specific cutting guide according to one embodiment.

FIG. 21B is a bottom view of patient-specific cutting guide 1400 according to one embodiment. The patient-specific cutting guide 1400 may include an alternative embodiment of a registration key. The patient-specific cutting guide 1400 may include registration key 2110 which may include all area of the inferior side 1418. The registration key 2110 can be further divided into a proximal projection 2112, a distal projection 2114, and a midsection projection 2116 between the proximal projection 2112 and the distal projection 2114. The proximal projection 2112, distal projection 2114, and midsection projection 2116 facilitate the patient-specific cutting guide 1400 in seating onto the adjacent joints of the patient.

Figure 22A:
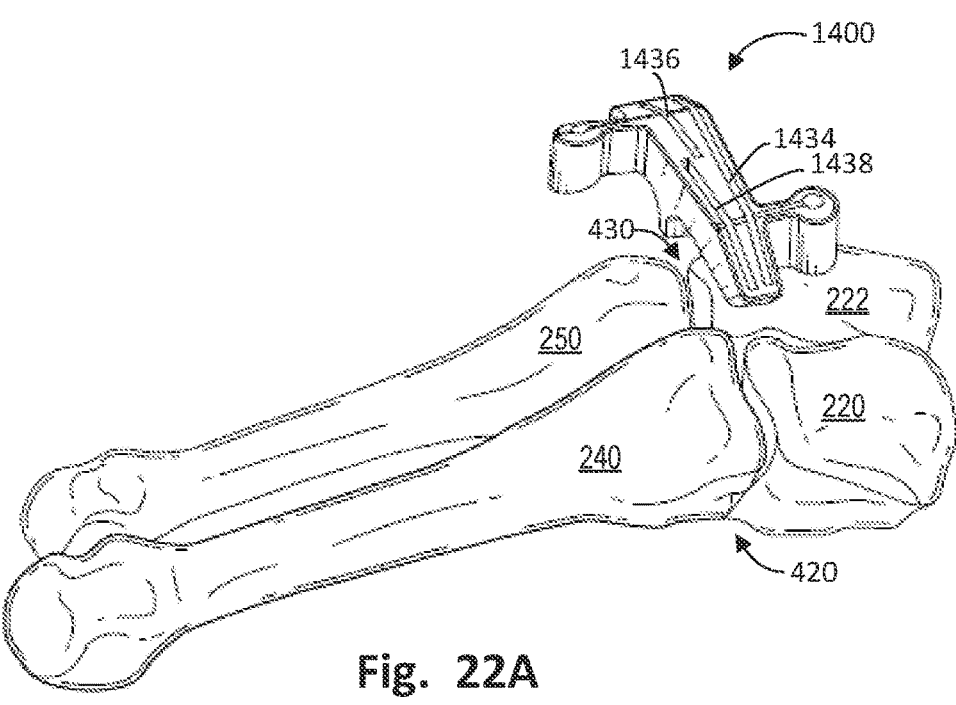
FIG. 22A is a perspective view of a patient-specific cutting guide positioned for placement on adjacent joints of a second metatarsal and a third metatarsal of a foot according to one embodiment.

FIG. 22A is a perspective view of a patient-specific cutting guide 1400 positioned for placement on adjacent joints (e.g., second TMT joint 420 and third TMT joint 430) of a foot according to one embodiment. The patient-specific cutting guide 1400 is properly positioned above the second TMT joint 420 and third TMT joint 430, but as yet not attached to the foot. The surgeon has made the incision(s) to expose the dorsal surfaces of the intermediate cuneiform 220, lateral cuneiform 222, second metatarsal 240, and third metatarsal 250, and has inserted the cutting guide 1400 such that the inferior side 1418 can be placed on the corresponding dorsal surfaces of the intermediate cuneiform 220, lateral cuneiform 222, second metatarsal 240, and third metatarsal 250. Since the inferior side 1418 is contoured to match the bone surfaces on which the patient-specific cutting guide 1400 will rest, the body 1402 may readily slide into its proper position traversing the second TMT joint 420 and third TMT joint 430.

FIG. 22A illustrates an embodiment of a patient-specific cutting guide that includes one or more guide features 1432. In particular, the patient-specific cutting guide 1400 includes a first guide feature implemented as a first slot 1434, a second guide feature implemented as a second slot 1436, and a third guide feature implemented as a third slot 1438.

Figure 22B:
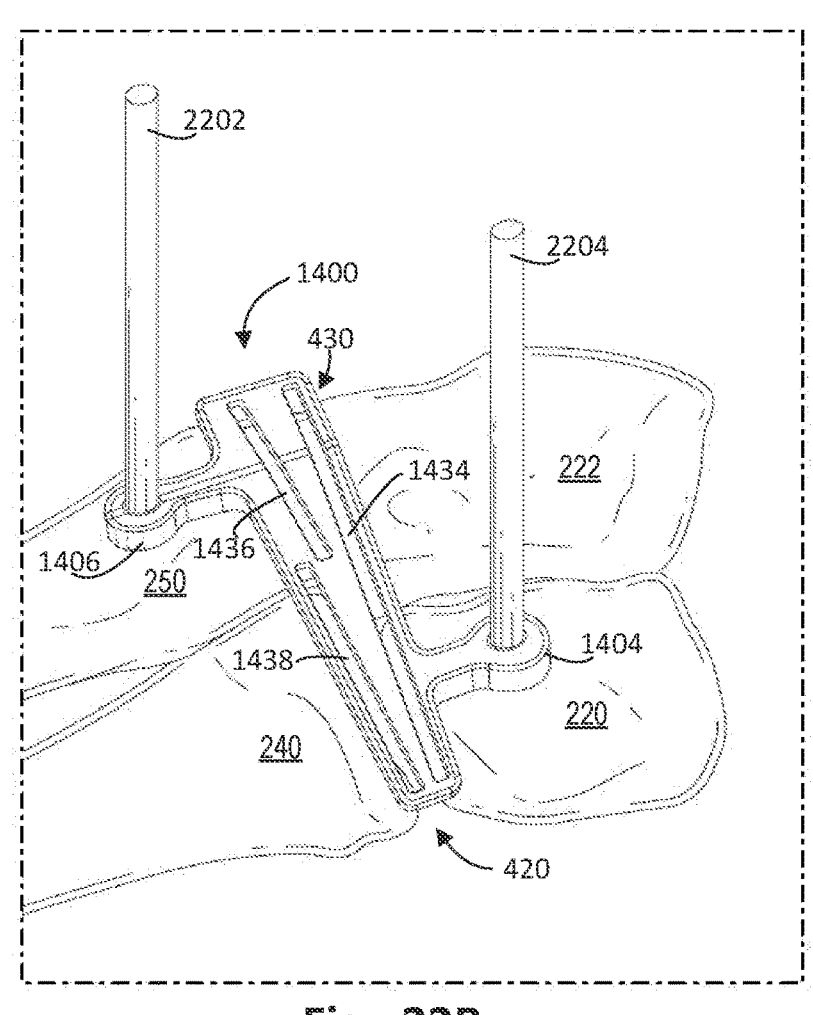
FIG. 22B is a perspective view of a patient-specific cutting guide positioned on adjacent joints of a second metatarsal and a third metatarsal of a foot according to one embodiment.

FIG. 22B is a perspective view of the patient-specific cutting guide 1400 of FIG. 22A positioned on adjacent joints of a second metatarsal and a third metatarsal of a foot according to one embodiment. The patient-specific cutting guide 1400 is secured by one or more fasteners 2202, 2204 is coordination with one or more anchor features (e.g., proximal anchor feature 1404 and/or distal anchor feature 1406). In certain embodiments, the one or more anchor features may include two or more holes configured to receive fasteners. In the illustrated embodiment, the fasteners 2202, 2204 are embodied as pins, such as K-wires. The fasteners 2202, 2204 can secure the patient-specific cutting guide 1400 across the one or more joints as an osteotomy is performed on bones of the joints. Those of skill in the art will appreciate that the proximal anchor feature 1404 may be dorsal to the lateral cuneiform 222 and the distal anchor feature 1406 may be dorsal to the second metatarsal 240. Alternatively, or in addition, two proximal anchor features 1404 and/or two distal anchor features 1406 can be used.

In the illustrated embodiment, the first slot 1434 traverses a first joint and a second joint of two adjacent joints. In the example, the first slot 1434 traverses both the second TMT joint 420 and the third TMT joint 430. The second slot 1436 traverses one of the first joint and the second joint of the two adjacent joints. In the example, the second slot 1436 traverses the third TMT joint 430. The third slot 1438 traverses the other one of the first joint and the second joint of the two adjacent joints. In the example, the third slot 1438 traverses the second TMT joint 420 (e.g., the joint not traversed by the second slot 1436).

Advantageously, at least one of the one or more guide features 1432 can be positioned and/or oriented with the body 1402 based at least on patient imaging data. In addition, the one or more guide features 1432 may be positioned and/or oriented based on, or determined by, patient imaging data, the anatomical structures of the patient, the osteotomy procedure being performed, preferences of the surgeon, the nature of a patient's condition, and the like. Those of skill in the art will appreciate that the position and orientation of the one or more guide features 1432 and the corresponding cut surface a surgeon can form using these guide features can vary depending on the anatomical structures of the patient, the osteotomy procedure being performed, preferences of the surgeon, the nature of the condition, and the like.

Figures 23, 24:
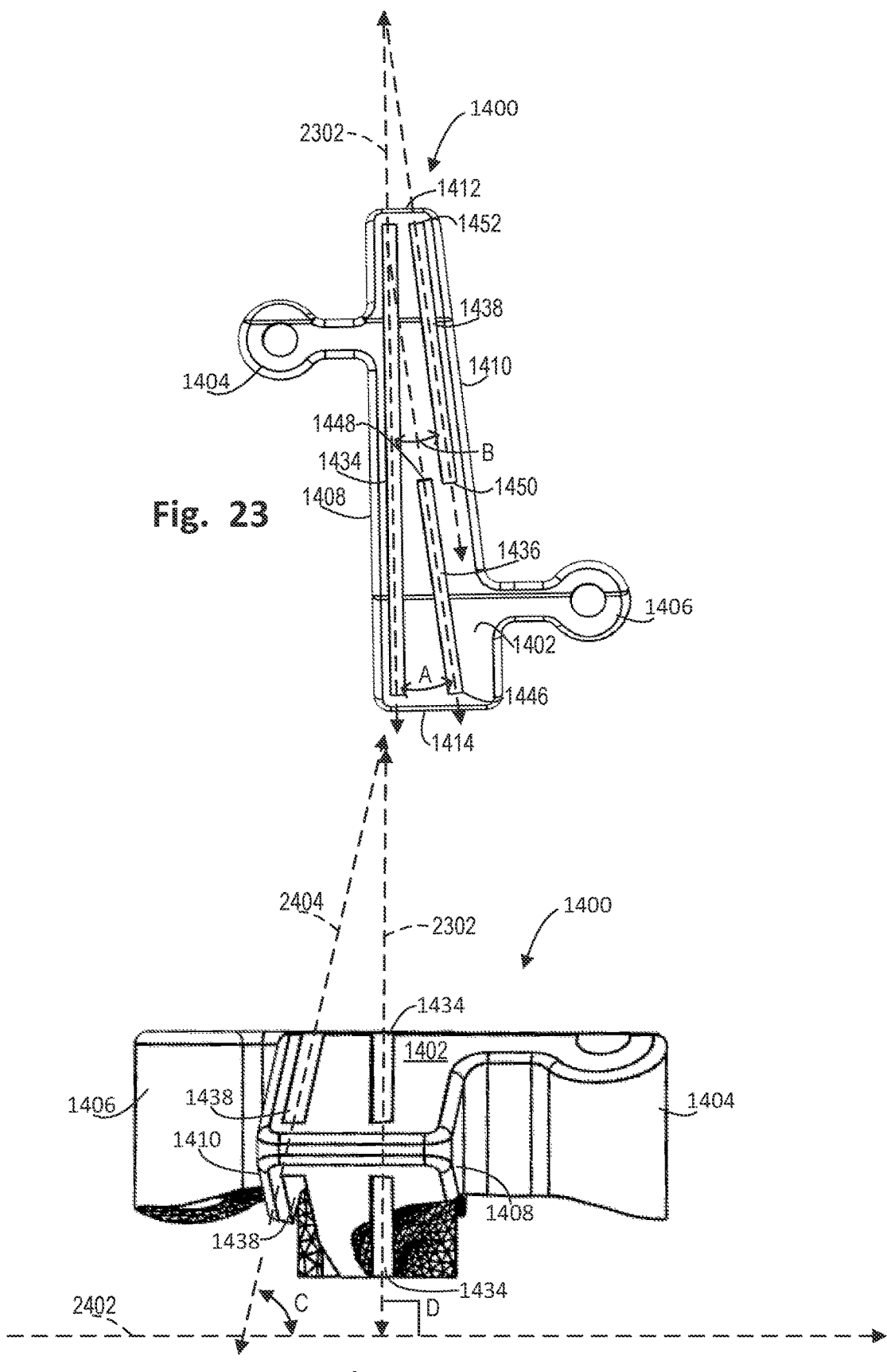
FIG. 23 is a top view of a patient-specific cutting guide according to one embodiment.
FIG. 24 is a side view of a patient-specific cutting guide according to one embodiment.

FIG. 23 is a top view of a patient-specific cutting guide 1400 according to one embodiment. In one embodiment, the body 1402 of the patient-specific cutting guide 1400 may include a longitudinal axis 2302. The longitudinal axis 2302 may run lengthwise from the medial side 1412 to the lateral side 1414. The longitudinal axis 2302 may be centered within a guide feature such as first slot 1434. In one embodiment, a size, position, and/or orientation of the first slot 1434 may be determined based, at least in part, on one or more of patient imaging data, anatomical structures of the patient, the osteotomy procedure being performed, preferences of the surgeon, a request of the surgeon, the nature of a patient's condition, and the like. In the illustrated example, the first slot 1434 is positioned near the proximal side 1408 and parallel to the longitudinal axis 2302.

Similarly, in one embodiment, a size, position, and/or orientation of the second slot 1436 and/or third slot 1438 may be determined based, at least in part, on one or more of patient imaging data, anatomical structures of the patient, the osteotomy procedure being performed, preferences of the surgeon, a request of the surgeon, the nature of a patient's condition, and the like. In the illustrated example, the second slot 1436 is positioned between the first slot 1434 and the distal side 1410 and at a first angle (illustrated by angles A and B) relative to the longitudinal axis 2302. The second slot 1436 may be oriented within the body 1402 relative to the longitudinal axis 2302 such that the medial end 1448 is closer to the first slot 1434 than the lateral end 1446 is to the first slot 1434. In the illustrated embodiment, this orientation is indicated by angle A and angle A extends distally from the longitudinal axis 2302. In addition, the third slot 1438 is positioned between the first slot 1434 and the distal side 1410 and at an angle (illustrated by angle B) relative to the longitudinal axis 2302. The third slot 1438 may be oriented within the body 1402 relative to the longitudinal axis 2302 such that the medial end 1452 is closer to the first slot 1434 than the lateral end 1450 is to the first slot 1434. In the illustrated embodiment, this orientation is indicated by angle B and angle B extends distally from the longitudinal axis 2302. Of course, angle A and/or B can extend proximally from the longitudinal axis 2302 in certain embodiments. Angles A and/or B can range from between about 0 degrees and about 90 degrees in various embodiments.

FIG. 24 is a side view of a patient-specific cutting guide 1400 of FIG. 23 according to one embodiment. The longitudinal axis 2302 may be centered within a guide feature such as, for example, first slot 1434. In one embodiment, a size, position, and/or orientation of the first slot 1434, second slot 1436, and/or third slot 1438 may be determined based, at least in part, on one or more of patient imaging data, anatomical structures of the patient, the osteotomy procedure being performed, preferences of the surgeon, a request of the surgeon, the nature of a patient's condition, and the like. In the illustrated example, the first slot 1434 and third slot 1438 are visible.

FIG. 24 illustrates that the first slot 1434 and third slot 1438 can extend through the body 1402 from the superior side 1416 to the inferior side 1418. The first slot 1434, second slot 1436, and/or third slot 1438 can extend through the body 1402 at an orientation that may extend distally or proximally in relation to a superior side 1416 or other reference such as a longitudinal axis 2402 of a bone. This orientation may be represented by a second angle (illustrated by angles C and D). The longitudinal axis 2402 may be a longitudinal axis of any of the bones of the adjacent joints (e.g., intermediate cuneiform 220, second metatarsal 240 or lateral cuneiform 222, third metatarsal 250). In the illustrated embodiment, in one example, the longitudinal axis 2402 may be long axis of an intermediate cuneiform 220. FIG. 24 illustrates that the angle C between the third slot 1438 and a reference axis 2404 may be about 79 degrees. FIG. 24 illustrates that the angle D between the first slot 1434 and the longitudinal axis 2302 may be 90 degrees. Advantageously, angles C and D and A and B can be defined based on the custom needs of the patient, surgeon desires, a surgical technique, or the like. The angles A, B, C, and D define in the patient-specific cutting guide 1400 where a surgeon will be able to make resections of one or more bones of the adjacent joints. A surgeon can define or accept a recommendation of the angles A, B, C, and D that will most help the surgeon in addressing or mitigating a condition and accomplishing a desired outcome.

In certain embodiments, it may be desirable to angle a resection of second metatarsal 240 or third metatarsal 250 (e.g., angle C) and make the angle for the resection of intermediate cuneiform 220 or lateral cuneiform 222 (e.g., angle D) straight (90 degrees). However, the present disclosure enables a surgeon to define the angles for A, B, C, or D such that any bone of the adjacent joints can be resected at an angle less than or equal to or greater than 90 degrees in relation to the longitudinal axis 2402.

In the illustrated example, a single longitudinal axis 2402 is used. However, a longitudinal axis for each of two or more bones of a joint can also be used to determine an angle for a guide feature that will guide resection of a bone. For example, the longitudinal axis 2402 may be long axis of an intermediate cuneiform 220 and may be used to determine angle D and another long axis, such as a long axis of a second metatarsal 240 may be used to determine angle C. Angles A and/or B can range from between about 20 degrees and about 90 degrees in either a proximal direction or a distal direction in various embodiments.

Referring now to FIGS. 23 and 24, a first angle (e.g., A and/or B) and/or a second angle (e.g., C and/or D) can be defined based on, or determined by, patient imaging data. Once defined, the one or more guide features 1432 defined within the patient-specific cutting guide 1400 at these angles can be used to enable a surgeon to make resections of bones of adjacent joints in a straightforward manner once the patient-specific cutting guide 1400 is secured dorsal to the adjacent joints. Advantageously, these angles (e.g., A, B, C, D) and/or the positioned and/or sizes of the one or more guide features 1432 can be used to correct anatomical defects or deformities of bones of a patient. Consequently, these angles (e.g., A, B, C, D) may also be referred to as correction angles. Once one or more resections are made using one or more guide features 1432 having these angles, the bones may be fixated to each other to perform a corrective osteotomy.

Figure 25:
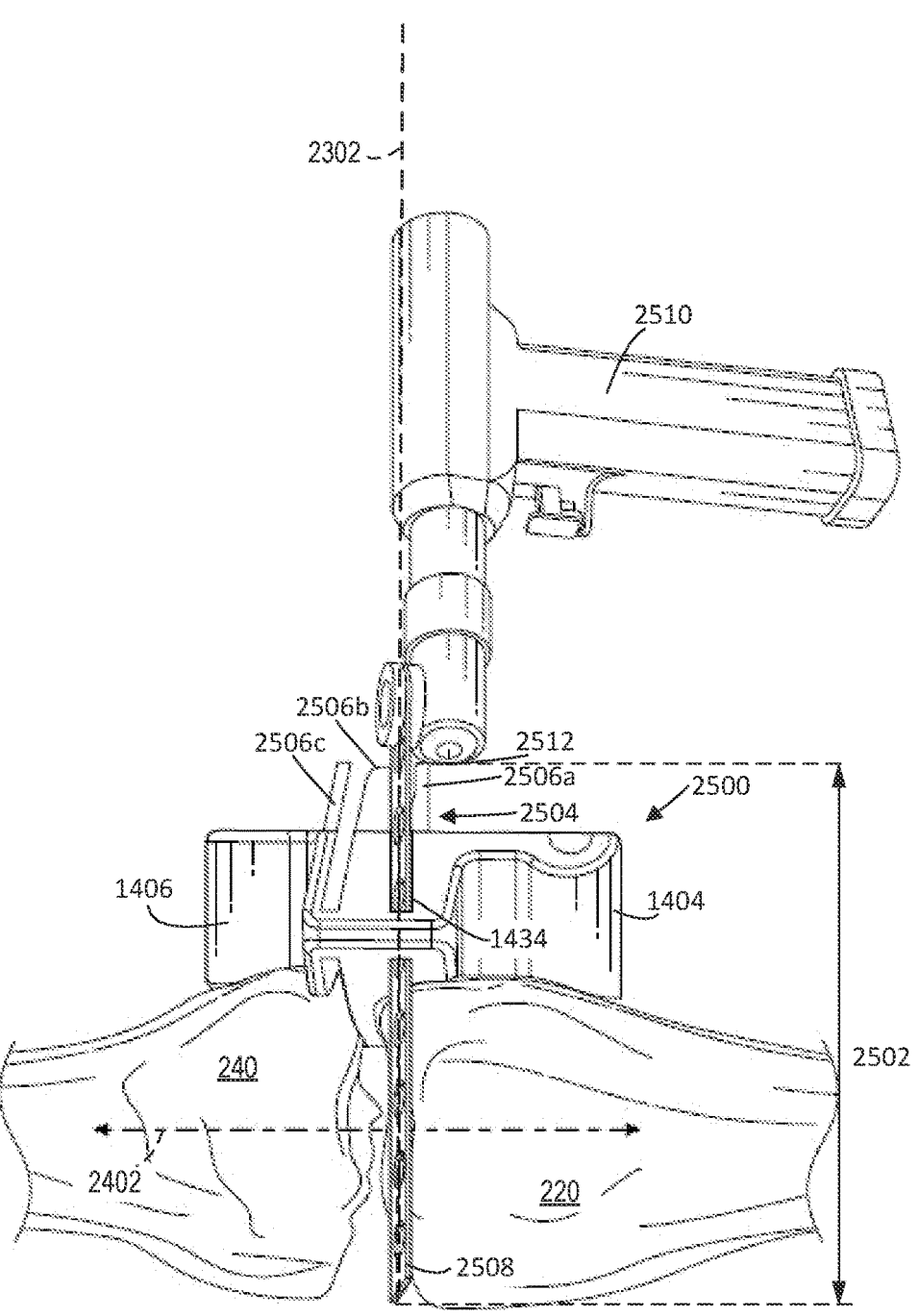
FIG. 25 illustrates a perspective side view of a patient-specific cutting guide positioned on adjacent joints of a second metatarsal and a third metatarsal of a foot according to one embodiment.

FIG. 25 illustrates a perspective view of a patient-specific cutting guide 2500 over a tarsometatarsal joint. Advantageously, embodiments of the present disclosure can be used to control a depth of resections of one or more bones of one or more adjacent joints. In certain embodiments, the depth of resection is controlled by defining a maximum depth 2502 of one or more of the one or more guide features 1432. Those of skill in the art appreciate that the maximum depth 2502 can be controlled in a variety of ways, each of which is within the scope of this disclosure. In one example embodiment, the patient-specific cutting guide may include a stop. As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

In one example, the maximum depth 2502 may be controlled by fabricating the patient-specific cutting guide with a predetermined distance between the superior side 1416 and the inferior side 1418. In this manner, the superior side 1416 may serve as the stop preventing a cutting tool from advancing a cutting blade or burr or other cutting implement into a guide feature, such as a first slot 1434, past the maximum depth.

FIG. 25 illustrates an alternative embodiment of a patient-specific cutting guide 2500 that is similar to the patient-specific cutting guide 1400 embodiment described herein. One difference is the patient-specific cutting guide 2500 includes a separate structure that serves as a stop 2504. The stop 2504 serves to mitigate resection of patient tissue within a guide feature outside of a predefined area. The stop 2504 is configured to interfere with insertion of a cutting implement of a cutting tool within the guide feature such that the cutting implement remains within the predefined area. In particular, a stop 2504 can be used to manage a depth of a resection within the guide feature. In certain embodiments, a stop 2504 includes a planar superior surface. Advantageously, the stop 2504 may also include a sloped or contoured surface such that the cutting implement can be inserted to a shallower depth or a deeper depth at different positions along an opening of a guide feature. Said another away a maximum depth can vary from one end of a guide feature (e.g., a lateral end to a medial end). Advantageously, the details of the shape and configuration of the stop 2504 can be predefined based on one or more of patient imaging data, anatomical structures of the patient, the osteotomy procedure being performed, preferences of the surgeon, a request of the surgeon, the nature of a patient's condition, and the like.

In certain embodiments, rather than using the superior side 1416 as a stop, the patient-specific cutting guide 2500 may include a stop 2504 that includes one or more projections 2506a-c that extend from a surface of the superior side 1416 near one or more of the one or more guide features 1432.

In one embodiment, not every guide feature may include projections 2506. In other embodiments, each one or more guide features 1432 may include one or more projections 2506. Advantageously, a height of one or more of the stops 2504 may be defined based on one or more of patient imaging data, anatomical structures of the patient, the osteotomy procedure being performed, preferences of the surgeon, a request of the surgeon, the nature of a patient's condition, and the like. Consequently, one guide feature may include a first maximum depth and another guide feature may include a second maximum depth.

By defining the patient-specific cutting guide 2500 to include one or more maximum depths for the one or more guide features 1432, the patient-specific cutting guide 2500 can assist a surgeon in performing an osteotomy in a way that mitigates a risk of the resections unintentionally damaging, or resecting, hard tissue or soft tissue other than what is intended for the surgical procedure. In one example, a surgeon may determine it is best to resect an articular surface of a bone of a joint, but to stop the resection before a final portion (a distal portion or inferior portion) of the bone is resected. This final portion may then be resected using a manual tool or may remain connected as part of the surgical procedure.

FIG. 25 illustrates an example embodiment of a patient-specific cutting guide 2500 that includes at least one of the one or more guide features and/or the body 1402 that includes a stop 2504. The stop 2504 includes a maximum depth 2502 defined using patient imaging data. The stop 2504 is configured to limit the cutting tool 2510 to the maximum depth 2502.

The stop 2504 in FIG. 25 is implemented using one or more projections 2506. At the stage of a procedure illustrated in FIG. 25 the patient-specific cutting guide 2500 is secured (fasteners such as fastener 2202 and/or fastener 2204 are omitted) dorsal to one or more TMT joints, specifically the second TMT joint 420 and the third TMT joint 430.

A surgeon has begun resecting tissue of the joint(s) by inserting a blade 2508 of the cutting tool 2510, such as a surgical oscillating saw into a guide feature, first slot 1434. The blade 2508 has been inserted to the maximum depth 2502 and is stopped from further insertion into the first slot 1434 by the stop 2504. Specifically, projection 2506a contacts a face 2512 of the cutting tool 2510 and prevents further insertion of the blade 2508. Advantageously, a length of the blade 2508 (and/or a distance from a distal end of a blade to the face 2512) may be predefined, known, predetermined, and/or prescribed in a preoperative plan or prescription used for the surgical procedure. Advantageously, the patient-specific cutting guide 2500 with a stop 2504 can help a surgeon in performing the surgical procedure. If a surgeon resects until the cutting tool 2510 engages the stop 2504, the surgeon can be assured that the resection extends to a desired depth (not too far and not too short).

FIG. 26 is a flow chart diagram of one example method for making a patient-specific cutting guide configured for an osteotomy procedure according to one embodiment. Prior to steps of the method 2600, a bone model (also referred to as CAD model above) or one or more bones of a patient is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve as, or be a part of, anatomic data for a patient.

A bone model or anatomic model of a patient's body or body part(s) may be generated by computing devices that analyze medical imaging images. Structures of a patient's body can be determined using a process called segmentation. In certain embodiments, the patient imaging data maybe gathered from the patient as the patient is not placing their weight on one or more feet. Alternatively, or in addition, in certain embodiments, the patient imaging data maybe gathered from the patient as the patient is placing their weight on one or more feet. Such imaging may be referred to as weight-bearing patient imaging data. For example in one embodiment, the bone model is derived from patient imaging data generated while the patient placed their weight on at least one joint involved in the osteotomy procedure.

Generally, an osteotomy procedure is not done while a patient places their weight on one or more feet involved in the procedure. Thus, a surgeon may not be able to intraoperatively determine how much correction of bone positioning and/or rotation may be desired to correct a condition. However, because the present disclosure can be used to generate patient-specific cutting guide from weight-bearing patient imaging data, the present disclosure can provide instruments such as cut guide, pin guide, bone engagement surface(s), or the like that account for positions and configurations of the patient's bones while bearing the weight of the patient. Advantageously, using weight-bearing patient imaging data can provide for more successful procedures and more long term and lasting correction of conditions for the patient.

In one embodiment, the method 2600 begins after a bone model of a patient's body or body part(s) is generated. In a first step 2610, a bone model of one or more bones of a patient based on the condition and/or the bone model is accessed. In certain embodiments, the bone model may be patient specific. In other embodiments, the bone model may not be patient specific. For example, in another embodiment, the bone model accessed may be a bone model for a particular type of patient or a particular patient with a particular condition or class of conditions, or a bone model specific to any other of one or more aspects of a particular patient, while not being specific to one particular patient. For example, the bone model may be selected from a set of bone models that are determined to be helpful in addressing a condition of a particular patient.

Next, the method 2600 defines 2620 one or more guide features of a preliminary cutting guide model for an osteotomy procedure, the preliminary cutting guide model comprising a superior surface and an inferior surface. As discussed above, the number, position, size, orientation and/or configuration of the one or more guide features can also be defined. Alternatively, or in addition, a distance between a superior side 1416 and an inferior side 1418 (e.g., to serve as a stop), a configuration, number, and position of projections 2506, and the like can also be defined for the preliminary cutting guide model.

In addition, defining one or more guide features of the preliminary cutting guide model may include defining a registration key of the inferior surface of the preliminary cutting guide model according to a topographical surface of two or more bones of adjacent joints of the bone model such that the registration key substantially matches a gap between two or more bones of the bone model. The gap may be between a second TMT joint 420 and a third TMT joint 430, between a third TMT joint 430 and a fourth TMT joint 440, between a second TMT joint 420 and a first TMT joint 410, or between two or more bones of any particular joint.

In addition, defining one or more guide features of the preliminary cutting guide model may include defining a first slot configured to guide formation of a first cut surface of a first bone of the patient corresponding to a first modeled bone, defining a second slot configured to guide formation of a second cut surface of a second bone of the patient corresponding to a second modeled bone; defining a third slot configured to guide formation of a third cut surface of a third bone of the patient corresponding to a third modeled bone; and defining a fourth slot configured to guide formation of a fourth cut surface of a fourth bone of the patient corresponding to a fourth modeled bone. The first slot, second slot, third slot, and fourth slot may be positioned such that fixing the first cut surface of the first bone to the second cut surface and the third cut surface of the third bone to the fourth cut surface of the fourth bone mitigates a condition of the patient.

Next, the method 2600 proceeds by defining 2630 at least a portion of the inferior surface of the preliminary cutting guide model according to a topographical surface of at least one bone of the bone model such that the inferior surface substantially matches a contour of the topographical surface. After step 2630, the preliminary cutting guide model is configured for fabrication of a patient-specific cutting guide corresponding to the preliminary cutting guide model. After step 2630, the method 2600 may end.

In one aspect, the preliminary cutting guide may be used, as-is, without any further changes, modifications, or adjustments and thus become a patient-specific cutting guide. In another aspect, the preliminary cutting guide may be modified, adjusted, or configured to more specifically address the goals, objectives, or needs of a patient or a surgeon and by way of the modifications become a patient-specific cutting guide.

The patient-specific cutting guide can be used by a user, such as a surgeon, to guide making one or more resections of a structure, such as a bone for a procedure. Accordingly, a preliminary cutting guide model can be used to generate a patient-specific cutting guide model. The patient-specific cutting guide model may be used in a surgical procedure to address, correct, or mitigate effects of the identified deformity and may be used to generate a patient-specific cutting guide that can be used in a surgical procedure for the patient.

Furthermore, fabricating a patient-specific cutting guide that is customized to a particular patient and a specific desired correction/adjustment enables correction of a variety of conditions and/or angular deformities (in all 3 planes) of the midfoot or hind foot and ankle where an osteotomy could be used. For example, embodiments of the procedures and devices herein disclosed can be used to address cavus, and mid foot dislocations, fracture malunion, metatarsal adductus, etc. They can also be used in preparation for joint resurfacing procedures of the foot and ankle to optimize placement of an arthroplasty implant.

Those of skill in the art will appreciate that method 2600 is one of many that may be used to address a condition of the patient using the apparatuses, devices, methods, features, and aspects of the present disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, FIG., or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

53

54

What is claimed is:

1. A method for correcting a condition present in a patient's foot, the method comprising:

obtaining a bone model of one or more bones of a patient's foot;

using the bone model to generate a patient-specific cutting guide comprising:

a body configured to seat transverse to a plurality of joints, the body comprising:

a proximal side, a distal side, a medial side, a lateral side and a superior side;

an inferior side comprising a plurality of bone engagement surfaces shaped to match two surfaces of a first surface of a first bone, a second surface of a second bone, a third surface of a third bone, and a fourth surface of a fourth bone, wherein the first bone, the second bone, the third bone, and the fourth bone are bones of the plurality of joints of the patient's foot; and one or more guide features positioned to guide resection of at least one of the first bone, the second bone, the third bone, and the fourth bone during an osteotomy;

an anchor feature coupled to the body and configured to receive one or more fasteners to anchor the body to at least one of the first bone, the second bone, the third bone, and the fourth bone;

using the patient-specific cutting guide in a surgical procedure to correct a condition present in the patient's foot.

2. The method of claim 1, wherein the patient-specific cutting guide comprises a plurality of anchor features, the plurality of anchor features comprising a proximal anchor feature extending proximally from the body and a distal anchor feature extending distally from the body.

3. The method of claim 2, wherein the proximal anchor feature anchors the body to the first bone and the distal anchor feature anchors the body to the fourth bone, the fourth bone diagonally adjacent to the first bone.

4. The method of claim 2, wherein the proximal anchor feature extends proximally from the body and dorsal to one of two bones on a proximal side of two adjacent joints and the distal anchor feature extends distally from the body and dorsal to one of two bones on a distal side of the two adjacent joints.

5. The method of claim 4, wherein the proximal anchor feature comprises a first hole that passes through the proximal anchor feature and the proximal anchor feature is configured to guide a fastener deployed through the first hole toward a longitudinal axis of one of two bones on a proximal side of the two adjacent joints, when the patient-specific cutting guide is in use.

6. The method of claim 5, wherein the distal anchor feature comprises a second hole that passes through the distal anchor feature and the distal anchor feature is configured to guide a fastener deployed through the second hole toward a longitudinal axis of one of two bones on a distal side of the two adjacent joints, when the patient-specific cutting guide is in use.

7. The method of claim 1, wherein the anchor feature comprises a guide for at least one of a K-wire and a pin into a bone and wherein the one or more guide features are configured to be patient-specific.

8. The method of claim 7, wherein the body comprises a longitudinal axis that extends from a medial side of the body to a lateral side of the body and wherein at least one the one or more guide features are positioned at a first angle relative to the longitudinal axis, the first angle within a transverse plane of a patient's foot and the first angle determined at least in part by the bone model.

9. The method of claim 8, wherein the patient-specific cutting guide comprises:

a first guide feature that extends between a medial side of the patient-specific cutting guide and a lateral side of the patient-specific cutting guide, the first guide feature being coincident with the longitudinal axis;

a second guide feature extends between the medial side and the lateral side and positioned between the first guide feature and a distal side of the patient-specific cutting guide; and wherein the second guide feature extends away from the first guide feature at the first angle on the superior side of the patient-specific cutting guide.

10. The method of claim 9, wherein:

the first guide feature extends from the superior side to the inferior side at a first orientation perpendicular to a longitudinal axis of one of one of the first bone, the second bone, the third bone, and the fourth bone; and the second guide feature extends from the superior side to the inferior side at a second orientation that intersects the longitudinal axis of the one of one of the first bone, the second bone, the third bone, and the fourth bone at a second angle defined based at least in part on patient imaging data.

* * * * *